US012745931B2

(12) United States Patent
Adler et al.

(10) Patent No.: US 12,745,931 B2
(45) Date of Patent: Sep. 29, 2026

(54) OCCLUSION DEVICE WITH SENSING FUNCTIONALITY

(71) Applicant: Canary Medical Switzerland AG, Baar (CH)

(72) Inventors: Mark A. Adler, Carlsbad, CA (US); Jeffrey M. Gross, Carlsbad, CA (US); Peter J. Schiller, San Marcos, CA (US)

(73) Assignee: Canary Medical Switzerland AG, Baar (CH)

( * ) Notice: Subject to any disclaimer, the term of this patent is extended or adjusted under 35 U.S.C. 154(b) by 753 days.

(21) Appl. No.: 17/410,956

(22) Filed: Aug. 24, 2021

(65) Prior Publication Data

US 2022/0061679 A1 Mar. 3, 2022

Related U.S. Application Data

(60) Provisional application No. 63/217,693, filed on Jul. 1, 2021, provisional application No. 63/069,935, filed on Aug. 25, 2020.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0031* (2013.01); *A61B 5/02014* (2013.01); *A61B 5/026* (2013.01); *A61B 5/14503* (2013.01); *A61B 5/6876* (2013.01); *A61B 5/6882* (2013.01); *A61B 90/39* (2016.02); *A61B 2090/392* (2016.02); *A61B 2560/0214* (2013.01); *A61B 2560/0481* (2013.01)

(58) Field of Classification Search
None
See application file for complete search history.

(56) References Cited

U.S. PATENT DOCUMENTS 4,411,266 A 10/1983 Cosman
5,609,628 A * 3/1997 Keranen .......... A61B 17/12022 623/1.36

(Continued)

FOREIGN PATENT DOCUMENTS

AU 2013224644 A1 9/2013
CN 1899222 A 1/2007

(Continued)

OTHER PUBLICATIONS

Zhu et al. "Frequency and predictors of endoleaks and long-term patency after covered stent placement for the treatment of intracranial aneurysms: a prospective, non-randomised multicentre experience." Eur Radiol. Jan. 2013;23(1):287-97. Epub Jul. 11, 2012. (Year: 2012).*

(Continued)

*Primary Examiner* — Meredith Weare

(57) ABSTRACT

Systems and methods for delivering an implantable sensor assembly into a vascular structure. The sensor assembly is capable of detecting one or more physiological parameters of a patient and generating sensor data. The one or more physiological parameters may be indicative of blood flow through the vascular structure. The sensor assembly may wirelessly transmit the sensor data to a receiver.

16 Claims, 30 Drawing Sheets

(51) Int. Cl.

| | |
|---|---|
| ***A61B 5/02*** | (2006.01) |
| ***A61B 5/026*** | (2006.01) |
| ***A61B 90/00*** | (2016.01) |

(56) References Cited

U.S. PATENT DOCUMENTS 5,672,954 A 9/1997 Watanabe
5,980,550 A * 11/1999 Eder ................ A61B 17/12145 606/191
6,139,581 A 10/2000 Engh et al.
6,416,474 B1 * 7/2002 Penner ............... A61B 5/02014 604/103.02
6,706,071 B1 3/2004 Wolter
6,840,956 B1 1/2005 Wolinsky et al.
6,855,115 B2 2/2005 Fonseca et al.
7,009,511 B2 3/2006 Mazar et al.
7,025,778 B2 4/2006 Hayashi et al.
7,127,300 B2 10/2006 Mazar et al.
7,130,695 B2 10/2006 Czygan et al.
7,384,403 B2 6/2008 Sherman
7,574,792 B2 8/2009 O'Brien et al.
7,699,059 B2 4/2010 Fonseca et al.
8,075,627 B2 12/2011 Caylor, III et al.
8,556,888 B2 10/2013 Nields et al.
8,668,742 B2 3/2014 Caylor, III et al.
9,019,098 B2 4/2015 Okano
9,445,930 B2 9/2016 Chen et al.
9,456,915 B2 10/2016 Chen et al.
9,946,962 B2 4/2018 Hunter
9,949,669 B2 4/2018 DiSilvestro et al.
10,070,973 B2 9/2018 Sherman et al.
10,219,699 B2 3/2019 Wilder et al.
10,285,637 B1 5/2019 Hnat et al.
10,499,855 B2 12/2019 Hunter
10,582,891 B2 3/2020 Wiedenhoefer et al.
10,898,106 B2 1/2021 Bodewes et al.
11,684,260 B2 6/2023 Wiedenhoefer et al.
11,786,126 B2 10/2023 Hunter et al.
2002/0024450 A1 2/2002 Townsend et al.
2002/0147416 A1 10/2002 Zogbi et al.
2002/0156529 A1 10/2002 Li et al.
2003/0069644 A1 4/2003 Kovacevic et al.
2003/0088242 A1 5/2003 Prakash et al.
2003/0204267 A1 10/2003 Hazebrouck et al.
2004/0011137 A1 1/2004 Hnat et al.
2004/0019382 A1 1/2004 Amirouche et al.
2004/0019384 A1 1/2004 Kirking et al.
2004/0199238 A1 * 10/2004 Brown ................ A61B 5/0031 623/1.1
2004/0204766 A1 10/2004 Siebel
2004/0211580 A1 10/2004 Wang et al.
2004/0249464 A1 12/2004 Bindseil et al.
2004/0249471 A1 12/2004 Bindseil et al.
2005/0165317 A1 7/2005 Turner et al.
2006/0009856 A1 1/2006 Sherman et al.
2006/0030771 A1 2/2006 Levine et al.
2006/0030945 A1 2/2006 Wright
2006/0047283 A1 3/2006 Evans, III et al.
2006/0052816 A1 3/2006 Bates et al.
2006/0111777 A1 5/2006 Chen
2006/0116744 A1 6/2006 Von Arx et al.
2006/0142670 A1 6/2006 Disilvestro et al.
2006/0189926 A1 * 8/2006 Hall ................ A61B 5/150213 600/316
2006/0200030 A1 * 9/2006 White ..................... A61B 5/03 600/486
2006/0200121 A1 9/2006 Mowery
2006/0200220 A1 9/2006 Brown et al.
2006/0224088 A1 10/2006 Roche
2006/0229730 A1 10/2006 Railey et al.
2006/0271199 A1 11/2006 Johnson
2007/0004994 A1 1/2007 Sherman
2007/0005141 A1 1/2007 Sherman
2007/0089518 A1 4/2007 Ericson et al.
2007/0233065 A1 10/2007 Donofrio et al.
2007/0234819 A1 10/2007 Amirouche
2007/0239282 A1 10/2007 Caylor, III et al.
2007/0265662 A1 11/2007 Ufford
2008/0027679 A1 1/2008 Shklarski
2008/0033527 A1 2/2008 Nunez et al.
2008/0065225 A1 3/2008 Wasielewski
2008/0076972 A1 3/2008 Dorogusker et al.
2008/0275350 A1 11/2008 Liao et al.
2008/0300597 A1 12/2008 Morgan et al.
2008/0300659 A1 12/2008 Matos
2008/0306325 A1 12/2008 Burnett et al.
2009/0005656 A1 1/2009 Najafi et al.
2009/0012372 A1 1/2009 Burnett et al.
2009/0048524 A1 2/2009 Wildau et al.
2009/0088756 A1 4/2009 Anderson
2009/0135886 A1 5/2009 Robertson et al.
2009/0157146 A1 6/2009 Linder et al.
2009/0192533 A1 7/2009 Dlugos, Jr. et al.
2009/0216109 A1 * 8/2009 Karmarkar ............. A61B 5/055 604/500
2009/0253587 A1 10/2009 Fernandez
2010/0057046 A1 3/2010 Stevens et al.
2010/0106240 A1 4/2010 Duggal et al.
2010/0191100 A1 7/2010 Anderson et al.
2010/0204551 A1 8/2010 Roche
2010/0204802 A1 8/2010 Wilson et al.
2010/0256708 A1 10/2010 Thornton et al.
2011/0004076 A1 1/2011 Janna et al.
2011/0019595 A1 1/2011 Magar et al.
2011/0045047 A1 2/2011 Bennett et al.
2011/0054272 A1 3/2011 Derchak
2011/0063094 A1 3/2011 Meiertoberens et al.
2011/0087306 A1 4/2011 Goossen
2011/0208283 A1 8/2011 Rust
2011/0213413 A1 * 9/2011 Brown ............... A61B 17/0057 606/213
2011/0288436 A1 11/2011 Stone
2011/0319755 A1 12/2011 Stein et al.
2012/0029598 A1 2/2012 Zhao
2012/0123498 A1 5/2012 Gross
2012/0226360 A1 9/2012 Stein et al.
2012/0271200 A1 10/2012 Martinson et al.
2013/0046152 A1 2/2013 Najafi et al.
2013/0079675 A1 3/2013 Stein et al.
2013/0079679 A1 3/2013 Roche et al.
2013/0085350 A1 * 4/2013 Schugt ................. A61B 5/0031 607/59
2013/0123660 A1 5/2013 Tauber
2013/0123684 A1 5/2013 Giuffrida et al.
2013/0144379 A1 6/2013 Najafi et al.
2013/0202721 A1 * 8/2013 Silver .................. A61B 5/1477 600/352
2013/0225949 A1 8/2013 Roche
2013/0252610 A1 9/2013 Kim
2014/0031063 A1 1/2014 Park et al.
2014/0085102 A1 3/2014 Mccormick
2014/0088391 A1 3/2014 Leach
2014/0135589 A1 5/2014 Osorio
2014/0256324 A1 9/2014 Mohanty
2014/0275849 A1 9/2014 Acquista
2014/0275861 A1 9/2014 Kroh et al.
2014/0296663 A1 10/2014 Boyden et al.
2014/0328253 A1 11/2014 Lee
2014/0336764 A1 11/2014 Masson et al.
2014/0379090 A1 12/2014 Diomidis et al.
2015/0238304 A1 8/2015 Lamraoui
2015/0287544 A1 10/2015 Irazoqui et al.
2015/0327867 A1 11/2015 Bachman et al.
2016/0101281 A1 4/2016 Chen
2016/0128573 A1 5/2016 Wilder et al.
2016/0310066 A1 10/2016 Wiedenhoefer et al.
2017/0035593 A1 2/2017 Chen et al.
2017/0065207 A1 3/2017 Landherr et al.
2017/0119566 A1 5/2017 Chen et al.
2017/0138986 A1 5/2017 Kern
2017/0326355 A1 * 11/2017 Koop ..................... A61B 5/686
2018/0228428 A1 8/2018 Anker et al.
2018/0317925 A1 * 11/2018 Pillai ...................... A61B 5/076
2019/0046212 A1 2/2019 Unser

(56) References Cited

U.S. PATENT DOCUMENTS

| | | | |
|---|---|---|---|
| 2019/0231513 A1 | 8/2019 | Leuthardt et al. | |
| 2019/0231555 A1 | 8/2019 | Neubardt | |
| 2019/0247197 A1 | 8/2019 | Jagannathan et al. | |
| 2019/0336053 A1* | 11/2019 | Halac | A61B 5/14503 |
| 2020/0054215 A1 | 2/2020 | Roche | |
| 2020/0129087 A1 | 4/2020 | Sweeney et al. | |
| 2020/0155327 A1 | 5/2020 | Suh et al. | |
| 2020/0253563 A1 | 8/2020 | Folk et al. | |
| 2021/0077241 A1 | 3/2021 | Hunter | |
| 2021/0401418 A1 | 12/2021 | Dang et al. | |
| 2022/0110710 A1 | 4/2022 | Rangwala et al. | |
| 2022/0387186 A1 | 12/2022 | Golemon, Jr. et al. | |
| 2023/0285167 A1 | 9/2023 | Alva et al. | |
| 2023/0301802 A1 | 9/2023 | Trousdale et al. | |
| 2024/0156396 A1 | 5/2024 | Amiot et al. | |
| 2025/0120654 A1* | 4/2025 | Salant | G16H 20/10 |

FOREIGN PATENT DOCUMENTS

| | | | |
|---|---|---|---|
| CN | 101257860 | A | 9/2008 |
| CN | 101495025 | A | 7/2009 |
| CN | 101773387 | A | 7/2010 |
| CN | 101856222 | A | 10/2010 |
| CN | 202036215 | U | 11/2011 |
| CN | 102740803 | A | 10/2012 |
| CN | 102885626 | A | 1/2013 |
| CN | 103313661 | A | 9/2013 |
| CN | 103458830 | A | 12/2013 |
| CN | 103735303 | A | 4/2014 |
| CN | 103957992 | A | 7/2014 |
| CN | 105433949 | B | 6/2020 |
| DE | 4322619 | C1 | 9/1994 |
| DE | 10342823 | A1 | 4/2005 |
| JP | 2013523391 | A | 6/2013 |
| JP | 2022128381 | A | 9/2022 |
| KR | 20090009940 | A | 1/2009 |
| WO | 03047419 | A2 | 6/2003 |
| WO | 2003103539 | | 12/2003 |
| WO | 2006108065 | A2 | 10/2006 |
| WO | 2008032316 | A2 | 3/2008 |
| WO | 2008055229 | A2 | 5/2008 |
| WO | 2008094760 | A2 | 8/2008 |
| WO | 2008098255 | A2 | 8/2008 |
| WO | 2012095784 | A1 | 7/2012 |
| WO | 2014150288 | | 9/2014 |
| WO | 2015021807 | A1 | 2/2015 |
| WO | 2015200720 | A2 | 12/2015 |
| WO | 2015200722 | A2 | 12/2015 |
| WO | 2018104472 | A1 | 6/2018 |
| WO | 2019136218 | A1 | 7/2019 |
| WO | 2020035852 | A2 | 2/2020 |

OTHER PUBLICATIONS

Extended European Search Report for European Application No. 15842678.3, mailed Feb. 5, 2019,13 Pages.

International Preliminary Report on Patentability for International Application No. PCT/US2015/050789, mailed Mar. 30, 2017, 07 Pages.

International Search Report and Written Opinion for International Application No. PCT/US2015/050789, mailed Feb. 1, 2016, 10 Pages.

International Search Report and Written Opinion for International Application No. PCT/US2022/041402, mailed Jan. 12, 2023, 12 pages.

Partial Supplementary European Search Report for European Application No. 15842678.3, mailed Oct. 16, 2018, 15 Pages.

Xiang X., et al., "A Review of the Implantable Electronic Devices in Biology and Medicine," China Academic Journal Electronic Publishing House, vol. 32 (3), Mar. 3, 2004, pp. 462-467.

Yiming L., et al., "Application of Wireless Sensor Networks in Healthcare," Chinese Journal of Medical Instrumentation, vol. 37, No. 5, Dec. 31, 2013, pp. 351-354 and Figure 1.

PCT International Search Report and Written Opinion dated Dec. 28, 2021, for PCT/US2021/047390.

Kilinc et al., "Design and optimization of inductive power transmission for implantable sensor system." 2010 Xith International workshop on symbolic and numerical methods, modeling and applications to circuit design (SM2ACD). IEEE, 2010. Oct. 4, 2010 (Oct. 4, 2010).

Supplementary European Search Report in European Patent Application No. 21862593.7, dated Sep. 4, 2024, 17 Pages.

Supplementary European Search Report in European Patent Application No. 22862043.1, dated Dec. 23, 2024, 7 Pages.

European Search Report for European Patent Application No. 24205658.8, dated Feb. 28, 2025, 9 Pages.

CardioMEMS: "CardioMEMS AAA Pressure Sensor System Instructions for Use", Jul. 1, 2004, 7 Pages, https://usermanual.wiki/CardioMEMS-orporatedA-000051.revised-manual-with-ID-label-418825.pdf.

* cited by examiner

OCCLUSION DEVICE WITH SENSING FUNCTIONALITY

INCORPORATION BY REFERENCE TO ANY PRIORITY APPLICATIONS

Any and all applications for which a foreign or domestic priority claim is identified in the Application Data Sheet as filed with the present application are hereby incorporated by reference.

FIELD

The present disclosure relates generally to medical devices with a sensor, systems including such devices, methods of using such devices and systems and the data generated therefrom, and devices and methods to address problems associated with an implanted medical device with a sensor

BACKGROUND

After treating an internal injury or other internal defects, it can be difficult to monitor the progress of the patient's recovery. For example, aneurysms occur when the patient's artery wall weakens, which causes the weakened area to balloon. Aneurysms can occur throughout the body (e.g., the aorta, the brain, or elsewhere). A patient with an aneurysm will often experience no symptoms until the aneurysm ruptures. A ruptured aneurysm can result in internal bleeding, a stroke, and, occasionally, it can be fatal.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

One method of treating an aneurysm is coil embolization. During this procedure, the physician implants a structure, such as a metal coil, into the aneurysm to close off the aneurysm and reduce the risk of bleeding. After the procedure, it is difficult to monitor the progress of the aneurysm, especially if the aneurysm is located in the brain. This results in multiple follow up visits with the doctor, which can increase the patient's medical care costs. Moreover, compactions can occur at the neck of the aneurysm (i.e., the transition between the parent artery and the aneurysm). Currently, there is no mechanism to reliably monitor the aneurysm after treatment.

Certain aspects of this disclosure are directed toward an implantable sensor system capable of being implanted in any vascular structure such as an aneurysm. The sensor system may include one or more sensors and/or antennas. The antenna may be in electrical communication with the sensor. The sensor may continuously or intermittently detect one or more physiological parameters of a patient and generate sensor data. The antenna may continuously or intermittently transmit sensor data related to the one or more physiological parameters of the patient to a receiver, which may be located within the patient's body or outside of the patient's body. The antenna may be capable of stabilizing a position of the sensor in the vascular structure.

The sensor system described above may include one or more following features. The antenna may be capable of being compressed about the sensor for loading into a delivery system and expanded when released from the delivery system. The antenna may at least partially or entirely surround the sensor. The antenna may extend across one or more surfaces of the sensor. For example, the antenna may form a single axis loop, a dual axis loop, or a spherical loop around the sensor. The antenna may transmit and/or receive RF signals. Signals received by the antenna may adjust operation of the sensor system, for example the frequency or type of physiological parameter(s) being monitored or power management of the sensor system. In some configurations, the sensor may only perform a function upon receipt of a command from outside the patient's body. The antenna may include platinum metal, platinum/iridium alloy, and/or nitinol. The antenna may include an implantable material with the ability the ability to function with radio frequency performance. The antenna may be coated in a parylene film, a gold material, and/or a platinum material.

The sensor may include a radiopaque marker to identify a location of the sensor in the patient. The sensor may be a blood flow sensor, a blood pressure sensor, a metabolic sensor, a glucose sensor, an oxygen sensor, or other sensor. The sensor may generate the sensor data based on analyte materials, analyte elements, byproducts caused by certain cellular interactions or exchanges or blood interactions or exchanges in blood, and/or kinetic information. For example, the sensor may be capable of detecting oxygen, carbon dioxide, potassium, iron, and/or glucose in the blood of the patient.

The sensor system may include a sealing layer to hermetically seal the sensor assembly or individual components of the sensor assembly. The sensor system may include a dissolving membrane layer that dissolves when in contact with blood of the patient. The dissolving membrane layer may release clot enhancers when the dissolving membrane layer dissolves.

The sensor system may include a power source, such as a battery or supercapacitor, provided in the sensor system. Alternatively, the sensor may be powered by power source outside the patient's body. In some configurations, the sensor may be an inductive sensor. The power source may be rechargeable. The sensor system may include a memory device for storing sensor data or computer-executable instructions to be executed by a processor of the sensor system. The processor may be onboard the sensor or separate from the sensor.

The sensor system may be capable of being implanted in an aneurysm. The sensor system may detect one or more physiological parameters indicative of blood flow into or out of the aneurysm and/or level of clotting within the aneurysm.

The sensor may be capable of providing a first output indicative of a first level of blood flow and a second output indicative of a second level of blood flow. The first output may indicate a lack of clotting in the vascular structure. In response to the first output, a clinician may choose to deliver an occlusion device or deliver coagulant promoting drugs. The second output may indicate clotting in the vascular structure. In some configurations, the sensor may be a conductive switch.

Certain aspects of the disclosure are directed toward an implantable sensor system including a sensor assembly having any of the features described herein. The implantable sensor system may include an anchor structure for maintaining a position of the sensor in a vascular structure. The sensor assembly may be disposed within an interior space defined by the anchor structure. The anchor structure may be a separate component from the sensor. When implanted, the antenna of the sensor assembly may contact the anchor structure. This contact may enhance sensor data transmission. In other configurations, the sensor assembly may be directly or indirectly coupled to the anchor structure. For example, the antenna and/or the sensor may be directly or indirectly coupled to the anchor structure.

The anchor structure may be capable of occluding the vascular structure. The anchor structure may include one or more coils. The anchor structure may include a mesh or woven structure. The anchor structure may include a basket structure, a tubular structure, a structure with no lumen, or other structure.

In some configurations, the anchor structure may act as an antenna alone or in combination with a separate antenna. The anchor structure may be made from a similar material as the antenna. In some configurations, the anchor structure may form part of the sensor assembly. For example, the anchor structure may be made from a material enabling it to be part of the stacked configuration of the sensor assembly.

The anchor structure may have composite chemistry added to the inner or outer surface for carrying and releasing promotion healing materials or to support the clotting and sealing of the aneurysm, or inhibitors to enable the biofouling of the sensing system in the aneurysm to maintain a duration of function to detect and respond on the clotting in the aneurysm.

The sensor assembly and/or the anchor structure may be capable of eluting a drug to facilitate occlusion. The drug may be eluted upon implantation or at a predetermined amount of time after implantation. The drug may be eluted in response to the data collected from the sensor.

Any of the sensor assemblies or systems described herein may carry a drug (e.g., a coagulant) capable of treating a vascular structure in a patient. The drug may be coated on or stored in a cavity in the sensor assembly or the anchor structure. The sensor system may include a memory device for storing a computer-executable instruction. The sensor system may include a processor in communication with the memory device. The computer-executable instruction, when executed by the processor causes the processor to cause release the drug from the sensor assembly or the anchor structure. The computer-executable instruction may activate a switch to release the drug carried by the implantable sensor system. The processor may include a wireless receiver as a part of or separate from the antenna. The processor may execute the computer-executable instruction upon receipt of a wireless transmission from outside the body. The processor may execute the computer-executable instruction after a pre-determined time following implantation of the implantable sensor system.

Any of the sensor or sensor assemblies described herein may be capable of wirelessly communicating with an electronic device (e.g., base station or other computing device) using Bluetooth™, WiFi, ZigBee, cellular telephony, medical implant communication service ("MICS"), the medical device radio communications service ("MedRadio"), or other protocols. The electronic device may include a memory device and a processor. The memory device may be configured to store an application. The processor may execute the application to perform any of the functions described herein. For example, the processor may wirelessly communicate with a sensor assembly implanted in the vascular structure. The processor may determine a value of the one or more physiological parameters indicative of blood flow. The processor may output for presentation on a display the value for presentation to a user. The value may provide a metric indicative of a degree to which the vascular structure is occluding. The processor may execute the application to communicate the value via a communication network to a computing system. The processor may execute the application to transmit a setting adjustment command to the sensor assembly to adjust a setting for monitoring the one or more physiological parameters, for example the timing of collecting data. Additionally or alternatively, the setting adjustment command may adjust a different operation of the sensor assembly, such as power management. In some configurations, the sensor assembly may only collect data in response to a command received from the processor.

Certain aspects of the disclosure are directed toward a kit including an implantable sensor assembly and/or anchor structure having any of the features described herein. The kit may also include a delivery system capable of releasing the implantable sensor assembly and/or the anchor structure in the vascular structure. The same or different delivery systems may be used to deliver the sensor assembly and the anchor structure. Optionally, the kit may include the electronic device described herein.

Certain aspects of the disclosure are directed toward a method of monitoring a vascular structure using any of the sensor assemblies described herein. The vascular structure may include a neurovascular or cardiovascular structure, including but not limited to an aneurysm of an artery in a posterior circulation of the patient, a basilar aneurysm, a bifurcation aneurysm, a sidewall aneurysm, a ductus arteriosus, a carotid artery, or a venous structure. The method may include continuously or intermittently detecting one or more physiological parameters in the vascular structure using the implantable sensor assembly. The method may include continuously or intermittently transmitting sensor data related to the one or more physiological parameters to a remote location within the patient's body or outside the patient's body.

The method described above may include one or more following steps. The method may include occluding the vascular structure with an anchor structure. The sensor assembly may include a blood flow sensor, a blood pressure sensor, a metabolic sensor, a glucose sensor, an oxygen sensor, or other sensor. The method may include generating sensor data based on analyte materials, analyte elements, byproducts caused by certain cellular interactions or exchanges or blood interactions or exchanges in blood, and/or kinetic information. The sensor assembly may detect one or more physiological parameters, including but not limited to, oxygen, carbon dioxide, potassium, iron, and/or glucose in the blood of the patient. The method may include recharging the sensor assembly. The method may include recharging the sensor assembly.

Certain aspects of this disclosure are directed toward a method of implanting any of the sensor assemblies into a vascular structure of a patient. The method may include percutaneously advancing a delivery system carrying a sensor system to a vascular structure and releasing the sensor assembly into the vascular structure. The method may include advancing the delivery system over a guidewire or through a guide catheter. The delivery system may include a pusher to push the sensor assembly out of the delivery system. The method may also include simultaneously or separately releasing an anchor structure into the vascular structure. Releasing the anchor structure may include positioning the anchor structure around the sensor assembly. In other methods, the sensor assembly may be released in an interior space within the anchor structure. The anchor structure may occlude the vascular structure.

Certain aspects of this disclosure are directed toward a delivery system for delivering any of the sensor assemblies and/or systems described herein to a vascular structure. The delivery system can include a handle, a distal tip, and a shaft therebetween. The distal tip may be actively or passively deflected. In embodiments with active deflection, the distal tip may steered using mechanical and/or electronic controls. The distal tip may include a loading chamber for carrying the sensor assembly. The handle may include one or more user-actuatable mechanisms to release the sensor assembly and/or sensor system, control the distal tip, and/or stabilize the delivery system. The shaft may include one or more lumens, for example a guidewire lumen, a fluid delivery lumen, steering lumen, and/or a lumen for carrying a pusher. In some configurations, the delivery system includes a delivery sleeve positioned over the shaft. The delivery sleeve may directly or indirectly cause deflection of the distal tip.

Certain aspects of the disclosure toward an implantable sensor system that can be implanted in an aneurysm or other vascular structure. The sensor system may include a sensor assembly capable of being implanted within an aneurysm and measuring a physiological parameter. The sensor assembly may include one or more sensors including, but not limited to, a blood flow sensor, a blood pressure sensor, a metabolic sensor, a glucose sensor, an oxygen sensor, a conductivity switch, or a kinematic sensor. The sensor assembly may include a processor for at least partially processing data collected by the one or more sensors. The processor may be hermetically sealed to protect the processor from bodily fluids. The sensor assembly may include a memory device for storing sensor data. An outer surface of the sensor assembly may be shaped, treated, or otherwise modified to reduce endothelialization. For example, the outer surface of the sensor assembly may include peaks and valleys. The sensor system may include a battery or supercapacitor to power the sensor assembly. The sensor system may include an antenna in electrical communication with the sensor assembly. The sensor assembly may be positioned between the antenna and an anchor structure.

The sensor system may include an anchor structure for maintaining a position of the sensor assembly in the aneurysm. The anchor structure may be joined to or separate from the sensor assembly. In some configurations, the anchor structure may be joined and positioned between the sensor assembly and the battery or supercapacitor. The anchor structure may extend radially outward from a profile of the sensor assembly. The anchor structure may extend outward to contact a wall of the aneurysm. The anchor structure may include a plurality of anchor portions, which may be loop-shaped, coiled, or otherwise extending outward from the profile of the sensor assembly. The plurality of anchor portions may be circumferentially spaced apart. Each of the plurality of anchor portions may include an atraumatic end portion to contact a wall of the aneurysm. In some embodiments, the anchor structure may be drug-coated.

Certain aspects of the disclosure are directed toward a delivery system for deploying any of the sensor systems described herein. The delivery system may include a handle portion. The delivery system may include a delivery sheath or catheter through which an inner shaft may extend. The delivery system may include a retaining wire extending through the inner shaft. The retaining wire may retain a sensor system in a space between an outer wall of the inner shaft and an inner wall of the delivery sheath or within the inner shaft. The distal portion of the inner shaft may be deflectable or steerable.

In some embodiments, the inner shaft may include a plurality of openings in the shaft wall. The plurality of openings may be axially spaced apart along the shaft wall. In some configurations, the plurality of openings may be rotationally aligned. In other configurations, at least one of the plurality of openings may be rotationally offset from another one of the plurality of openings. The retaining wire may form one or more loop portions to retain the sensor system against the outer wall or inner wall of the inner shaft. For example, the retaining wire may extend out of a first opening in the shaft wall and into the space between the inner shaft and the delivery sheath, and then back through a second opening in the shaft wall and into the lumen of the inner shaft to form one of the one or more loop portions. As another example, the retaining wire may extend out of a first opening in the shaft wall and into the space between the inner shaft and the delivery sheath, and then back through the first opening in the shaft wall and into the lumen of the inner shaft to form one of the one or more loop portions.

Certain aspects of the disclosure are directed toward a method of deploying a sensor system in an aneurysm. The method may include advancing a delivery system carrying a sensor system to a parent artery. The sensor system may be carried by an inner shaft of the delivery system. The method may include unsheathing the sensor system and deploying the sensor system in the aneurysm. The method may include steering a distal tip of the inner shaft into the aneurysm prior to deploying the sensor system in the aneurysm, or positioning the sensor system against a neck of the aneurysm prior to deploying the sensor system in the aneurysm.

To deploy the sensor system, the method may include withdrawing a retaining wire to release the sensor system in the aneurysm. Withdrawing the retaining wire releases the retaining wire from an anchor structure of the sensor system. Deploying the sensor system may cause an anchor structure of the sensor system to expand and stabilize a position of the sensor system in the aneurysm. When deployed, a sensor of the sensor system is positioned away from a wall of the aneurysm. After deploying the sensor system in the aneurysm, a treatment device may be deployed in the aneurysm, for example around the sensor. Deploying the sensor system may include releasing communication circuitry of the sensor system in the aneurysm prior to releasing an anchor structure of the sensor system.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

Figure 1:
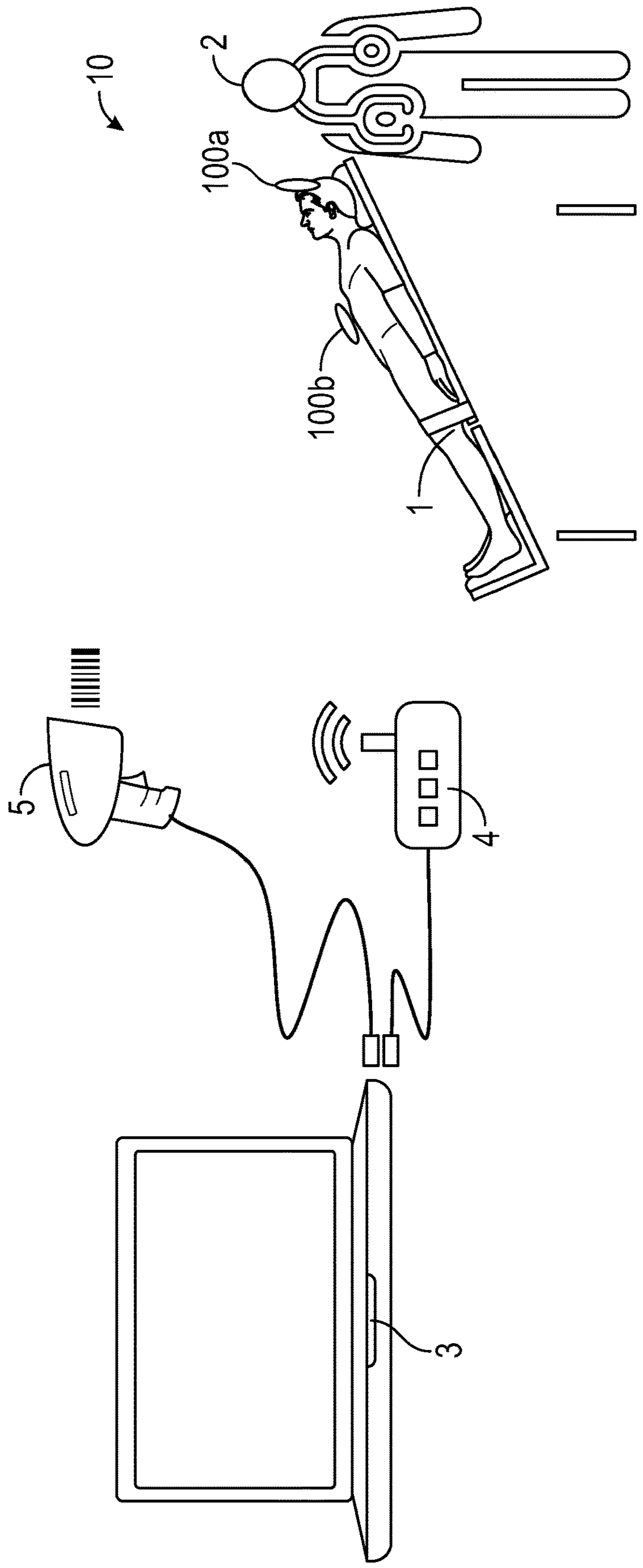
FIG. 1 illustrates an example sensor environment, according to certain aspects of the present disclosure.

The present disclosure may be understood more readily by reference to the following detailed description of example configurations of "a sensor assembly" or "a sensor system" included herein. The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, entirely firmware embodiments, or embodiments combining or subcombining software, firmware, and hardware aspects.

Prior to setting forth this disclosure in more detail, it may be helpful to an understanding thereof to provide definitions of certain terms to be used herein. Additional definitions are set forth throughout this disclosure. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" or "processor" means any device, system, or part thereof that controls at least one operation, such a device may be implemented in hardware (e.g., electronic circuitry), firmware, or software, or some combination of at least two of the same. The functionality associated with any particular controller may be centralized or distributed, whether locally or remotely. Other definitions of certain words and phrases may be provided within this patent document. Those of ordinary skill in the art will understand that in many, if not most instances, such definitions apply to prior as well as future uses of such defined words and phrases.

An “intelligent medical device” as used in the present disclosure, is an implantable or implanted medical device that desirably replaces or functionally supplements a subject’s natural body part. The intelligent medical device can include one of the disclosed sensor assemblies and/or an anchoring structure (e.g., a metal coil or basket). The sensor assembly will comprise or be associated with a controller or processor, also referred to as an implantable reporting processor (“IRP”). In one configuration, the intelligent medical device is an implanted or implantable medical device having a sensor assembly with the IRP arranged to perform the functions as described herein. The sensor assembly may perform one or more of the following exemplary actions in order to characterize the post-implantation status of the intelligent medical device: identifying the intelligent medical device or a portion of the intelligent medical device (e.g., the sensor assembly or by recognizing one or more unique identification codes for the intelligent medical device or a portion of the intelligent medical device); detecting, sensing and/or measuring parameters, which may collectively be referred to as monitoring parameters, in order to collect operational, physiological, kinematic or other data about the intelligent medical device or a portion of the intelligent prosthesis (e.g., the sensor assembly) and such data may optionally be collected as a function of time; storing the collected data within the intelligent medical device or a portion of the intelligent medical device (e.g., the sensor assembly); and communicating the collected data and/or the stored data by a wireless means from the intelligent medical device or a portion of the intelligent medical device (e.g., the sensor assembly) to an external computing device. The external computing device may have or otherwise have access to at least one data storage location such as found on a personal computer, a base station, a computer network, a cloud-based storage system, or another computing device that has access to such storage. Non-limiting and non-exhaustive list of configurations of intelligent medical devices include a metal coil configured to be implanted in an aneurysm.

“Monitoring data,” as used herein, individually or collectively includes some or all data associated with a particular implantable sensor assembly, and available for communication outside of the particular implantable sensor system. For example, monitoring data may include raw data from one or more sensors of the sensor assembly. The one or more sensors can be configured to detect analyte materials in the blood (e.g., glucose), analyte elements in the blood (e.g., oxygen or carbon dioxide), and the like that produce data associated with one or more physiological parameters of a patient. For example, the one or more physiological parameters of the patient can be associated with the patient’s aneurysm, after it has been treated via coil embolization or the like. Monitoring data may also include processed data from one or more sensors, status data, operational data, control data, fault data, time data, scheduled data, event data, log data, and the like associated with the particular sensor assembly. In some cases, high resolution monitoring data includes monitoring data from one, many, or all of the sensors of the sensor assembly that is collected in higher quantities, resolution, from more sensors, more frequently, or the like.

“Sensor” refers to a device that can be utilized to do one or more of detect, measure and/or monitor one or more different aspects of a body tissue (e.g., anatomy, physiology, metabolism, and/or function) and/or one or more aspects of the smart medical device or the sensor system. Representative examples of sensors suitable for use within the present invention include, for example, oxygen sensors, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain configurations the sensor can be a wireless sensor, or, within other configurations, a sensor connected to a wireless microprocessor. Within further configuration one or more (including all) of the sensors can have a Unique Sensor Identification number (“USI”) which specifically identifies the sensor.

“Sensor assembly” may refer to one or more components. For example, the “sensor assembly” may be a single component sensor with processing and wireless transmission on board the sensor. In other examples, the “sensor assembly” may be multiple components with a sensor and other components for performing one or more functions described herein.

In order to further understand the various aspects of the invention provided herein, the following sections are provided below: I. Overview; II. Sensor Assembly; A. Antenna (s); B. Sensor; C. Processor/Controller; D. Power Source; E. Sensor Assembly Configuration; III. Methods of Use of the Sensor System; IV. Kit; V. Delivery System; VI. Additional Embodiments and Terminology; and VII. Example Embodiments.

I. Overview

The apparatuses, systems, and methods disclosed in the present disclosure can be used in treating a vascular structure in a patient’s vascular system. Example vascular structures include neurovascular or cardiovascular structures, including but not limited to: an aneurysm, a carotid artery, a venous structure, a ductus arteriosus, or other vascular structure. Example aneurysms include: an aneurysm of an artery in a posterior circulation of the patient, a basilar aneurysm, a bifurcation aneurysm, an intracranial aneurysm, and a sidewall aneurysm. It can be difficult to monitor a treatment of an aneurysm, especially an intracranial aneurysm. Thus, it would be useful to implant an intelligent medical device and/or a sensor system with the implant (e.g., metal coil) in the aneurysm to monitor treatment.

FIG. 1 illustrates an example sensor environment 10. In the environment 10, one or more sensor assemblies **100*a*, 100*b* can be implanted by a medical practitioner 2 in the body of a patient 1. The sensor assembly 100*a*, 100*b* can include an associated implantable reporting processor (“IPR”) that can be arranged and configured to collect data including for example, medical and health data related to the patient 1 which the sensor assembly 100*a*, 100*b* is associated, and operational data of the sensor assembly 100*a*, 100*b* itself. The sensor assembly 100*a*, 100*b* can communicate with one or more base stations 4 or one or more computing devices 3 during different stages of monitoring the patient 1. While implanted in the patient’s body 1, the sensor assembly 100*a*, 100*b* can also communicate with a barcode scanner 5 such that the barcode scanner 5 can identify the particular assembly 100*a*, 100*b* implanted in the patient 1. The barcode scanner 5 and/or the base station 4 can communicate with the one or more computing devices 3**.

For example, in association with a medical procedure, the sensor assembly **100*a*, 100*b* can be implanted in the patient's body 1. The sensor assembly 100***a*, 100*b* can communicate with an operating room base station 4. While the patient 1 is at home and after sufficient recovery from the medical procedure, the sensor assembly 100*a*, 100*b* can be arranged to communicate with a home base station (not shown) and/or a doctor office base station (not shown). The sensor assembly 100*a*, 100*b* can communicate with each base station via a short range network protocol, such as the medical implant communication service ("MICS"), the medical device radio communications service ("MedRadio"), or some other wireless communication protocol suitable for use with the sensor assembly 100*a*, 100*b*.

The sensor assembly 100*a*, 100*b* may be a standalone medical device or it may be a component in a larger system, including an anchor structure such as a metal coil or basket that can desirably collect and provide in situ—patient medical data, device operational data, or other useful data.

The sensor assembly 100*a*, 100*b* can include one or more measurement units, for example a sensor, that can collect information and data, including medical and health data related to a patient 1 which the sensor assembly 100*a*, 100*b* is associated, and operational data of the assembly 100*a*, 100*b* itself.

The sensor assembly 100*a*, 100*b* can collect data at various different times and at various different rates during a monitoring process of the patient 1. In some configurations, the sensor assembly 100*a*, 100*b* may operate in a plurality of different phases over the course of monitoring the patient. For example, the sensor assembly 100*a*, 100*b* can collect more data soon after the sensor assembly 100*a*, 100*b* is implanted into the patient 1 and less data as the patient 1 heals and thereafter.

The amount and type of data collected by a sensor assembly 100*a*, 100*b* may be different from patient to patient, and the amount and type of data collected may change for a single patient. For example, a medical practitioner studying data collected by the sensor assembly 100*a*, 100*b* of a particular patient may adjust or otherwise control how the sensor assembly 100*a*, 100*b* collects future data.

The amount and type of data collected by a sensor assembly 100*a*, 100*b* may be different for different body parts, for different types of patient conditions, for different patient demographics, or for other differences. Alternatively, or in addition, the amount and type of data collected may change overtime based on other factors, such as how the patient is healing or feeling, how long the monitoring process is projected to last, how much battery power remains and should be conserved, the type of movement being monitored, the body part being monitored, and the like. In some cases, the collected data can be supplemented with personally descriptive information provided by the patient such as subjective pain data, quality of life metric data, co-morbidities, perceptions or expectations that the patient associates with the sensor assembly 100*a*, 100*b*, or the like.

Implantation of the sensor assembly 100*a*, 100*b* into the patient 1 may occur in an operating room, as shown in FIG. 2. As used herein, operating room includes any office, room, building, or facility where the sensor assembly 100*a*, 100*b* can be implanted into the patient. For example, the operating room may be a typical operating room in a hospital, an operating room in a surgical clinic or a doctor's office, or any other operating theater, interventional suite, intensive care ward, emergency room or the like where the sensor assembly 100*a*, 100*b* is implanted into the patient.

The operating room base station 4 can be utilized to configure and initialize the sensor assembly 100*a*, 100*b* when the sensor assembly 100*a*, 100*b* is being implanted into the patient 1. A communicative relationship can be formed between the sensor assembly 100*a*, 100*b* and the operating room base station 4, for example, based on a polling signal transmitted by the operating room base station 4 and a response signal transmitted by the sensor assembly 100*a*, 100*b*.

Upon forming a communicative relationship, which can often occur prior to implantation of the sensor assembly 100*a*, 100*b*, the operating room base station 4 can transmit initial configuration information to the sensor assembly 100*a*, 100*b*. The initial configuration information may include, but is not limited to, a time stamp, a day stamp, an identification of the type and placement of the sensor assembly 100*a*, 100*b*, information on other implants associated with the sensor assembly 100*a*, 100*b*, surgeon information, patient identification, operating room information, and the like.

In some configurations, the initial configuration information can be passed unidirectionally. In some embodiments, the initial configuration information can be passed bidirectionally. The initial configuration information may define at least one parameter associated with the collection of data by the sensor assembly 100*a*, 100*b*. For example, the initial configuration information may identify settings for one or more sensors of the sensor assembly 100*a*, 100*b* for each of one or more modes of operation. The initial configuration information may also include other control information, such as an initial mode of operation of the sensor assembly 100*a*, 100*b*, a particular event that triggers a change in the mode of operation, radio settings, data collection information (e.g., how often the sensor assembly 100*a*, 100*b* wakes up to collected data, how long it collects data, how much data to collect), home base station (not shown), computing device 3, and a connected personal assistant identification information, and other control information associated with the implantation or operation of the sensor assembly 100*a*, 100*b*. Examples of a connected personal assistant, which also can be called a smart speaker, include Amazon Echo®, Amazon Dot®, Google Home®, Philips® patient monitor, Comcast's health-tracking speaker, and Apple HomePod®.

In some configurations, the initial configuration information may be pre-stored on the operating room base station 4 or an associated computing device 3. In other configurations, a surgeon, surgical technician, or some other medical practitioner 2 may input the control information and other parameters to the operating room base station 4 for transmission to the sensor assembly 100*a*, 100*b*. In at least one such configuration, the operating room base station 4 may communicate with an operating room configuration computing device 3. The operating room configuration computing device 3 can include an application with a graphical user interface that enables the medical practitioner to input configuration information for the sensor assembly 100*a*, 100*b*. In various configurations, the application executing on the operating room configuration computing device 3 may have some of the configuration information predefined, which may or may not be adjustable by the medical practitioner 2. The operating room configuration computing device 3 can communicate the configuration information to the operating room base station 4 via a wired, as shown in FIG. 1, or wireless network connection (e.g., via a USB connection, Bluetooth connection, Bluetooth Low Energy ("BTLE") connection, or Wi-Fi connection), which can communicate it to the sensor assembly 100*a*, 100*b*.

The operating room configuration computing device 3 may also display information regarding the sensor assembly 100*a*, 100*b* or the operating room base station 4 to the surgeon, surgical technician, or other medical practitioner 2. For example, the operating room configuration computing device 3 may display error information if the sensor assembly 100*a*, 100*b* is unable to store or access the configuration information, if the sensor assembly 100*a*, 100*b* is unresponsive, if the sensor assembly 100*a*, 100*b* identifies an issue with one of the sensors or radio during an initial self-test, if the operating room base station 4 is unresponsive or malfunctions, or for other reasons.

Although the operating room base station 4 and the operating room configuration computing device 3 are described as separate devices, embodiments are not so limited; rather, the functionality of the operating room configuration computing device 3 and the operating room base station 4 may be included in a single computing device or in separate devices as illustrated. In this way, the medical practitioner 1 may be enabled in one embodiment to input the configuration information directly into the operating room base station 4.

Returning to FIG. 1, once the sensor assembly 100*a*, 100*b* is implanted into the patient and the patient returns home, the home base station, the computing or smart device (e.g., the patient's smart phone), the connected personal assistant, or two or more of the home base station, and the computing or smart device, and the connected personal assistant can communicate with the sensor assembly 100*a*, 100*b*. The sensor assembly 100*a*, 100*b* can collect data at determined rates and times, variable rates and times, or otherwise controllable rates and times. Data collection can start when the sensor assembly 100*a*, 100*b* is initialized in the operating room, when directed by a medical practitioner 1, or at some later point in time. At least some data collected by the sensor assembly 100*a*, 100*b* may be transmitted to the home base station directly, to the smart device directly, to the connected personal assistant directly, to the base station via one or both of the smart device and the connected personal assistant, to the smart device via one or both of the base station and the connected personal assistant, or to the connected personal assistant via one or both of the smart device and the base station. Here, "one or both" means via an item alone, and via both items serially or in parallel. For example, data collected by the sensor assembly 100*a*, 100*b* may be transmitted to the home base station via the smart device alone, via the connected personal assistant alone, serially via the smart device and the connected personal assistant, serially via the connected personal assistant and the smart device, and directly, and possibly contemporaneously, via both the smart device and the connected personal assistant. Similarly, data collected by the sensor assembly 100*a*, 100*b* may be transmitted to the smart device via the home base station alone, via the connected personal assistant alone, serially via the home base station and the connected personal assistant, serially via the connected personal assistant and the home base station, and directly, and possibly contemporaneously, via both the home base station and the connected personal assistant. Further in example, data collected by the sensor assembly 100*a*, 100*b* may be transmitted to the connected personal assistant via the smart device alone, via the home base station alone, serially via the smart device and the home base station, serially via the home base station and the smart device, and directly, and possibly contemporaneously, via both the smart device and the home base station.

In various configurations, one or more of the home base station, the smart device, and the connected personal assistant can ping the sensor assembly 100*a*, 100*b* at periodic, predetermined, or other times to determine if the sensor assembly 100*a*, 100*b* is within communication range of one or more of the home base station, the smart device, and the connected personal assistant. Based on a response from the sensor assembly 100*a*, 100*b*, one or more of the home base station, the smart device, and the connected personal assistant determines that the sensor assembly 100*a*, 100*b* is within communication range, and the sensor assembly 100*a*, 100*b* can be requested, commanded, or otherwise directed to transmit the data it has collected to one or more of the home base station, the smart device, and the connected personal assistant.

Each of one or more of the home base station, the smart device, and the connected personal assistant may, in some cases, be arranged with a respective optional user interface. The user interface may be formed as a multimedia interface that unidirectionally or bi-directionally passes one or more types of multimedia information (e.g., video, audio, tactile, etc.). Via the respective user interface of one or more of the home base station, the smart device, and the connected personal assistant, the patient 1 or an associate (not shown in FIG. 1) of the patient 1 may enter other data to supplement the data collected by the sensor assembly 100*a*, 100*b*. A user, for example, may enter personally descriptive information (e.g., age change, weight change), changes in medical condition, co-morbidities, pain levels, quality of life, or other subjective metric data, personal messages for a medical practitioner, and the like. In these configurations, the personally descriptive information may be entered with a keyboard, mouse, touch-screen, microphone, wired or wireless computing interface, or some other input means. In cases where the personally descriptive information is collected, the personally descriptive information may include, or otherwise be associated with, one or more identifiers that associate the information with unique identifier of the sensor assembly 100*a*, 100*b*, the patient, an associated medical practitioner, an associated medical facility, or the like.

In some of these cases, a respective optional user interface of each of one or more of the home base station, the smart device, and the connected personal device may also be arranged to deliver information associated with the sensor assembly 100*a*, 100*b* to the user from, for example, a medical practitioner 2. In these cases, the information delivered to the user may be delivered via a video screen, an audio output device, a tactile transducer, a wired or wireless computing interface, or some other like means.

In configurations where one or more of the home base station, the smart device, and the connected personal assistant are arranged with a user interface, which may be formed with an internal user interface arranged for communicative coupling to a patient portal device. The patient portal device may be smartphone, a tablet, a body-worn device, a weight or other health measurement device (e.g., thermometer, bathroom scale, etc.), or some other computing device capable of wired or wireless communication. In these cases, the user is able to enter the personally descriptive information, and the user also may be able to receive information associated with the sensor assembly 100*a*, 100*b*.

The home base station can utilize a home network of the patient to transmit the collected data to cloud. The home network, which may be a local area network, provides access from the home of the patient to a wide area network, such as the internet. In some configurations, the home base station may utilize a Wi-Fi connection to connect to the home network and access the internet. In other embodiments, the home base station may be connected to a home computer (not shown) of the patient, such as via a USB connection, which itself is connected to the home network.

The smart device can communicate with the sensor assembly 100*a*, 100*b* directly via, for example, Bluetooth® compatible signals, and can utilize the home network of the patient to transmit the collected data to cloud, or can communicate directly with the cloud, for example, via a cellular network. Alternatively, the smart device can be configured to communicate directly with one or both of the base station and the connected personal assistant via, for example, Bluetooth® compatible signals, and is not configured to communicate directly with the sensor assembly 100*a*, 100*b*.

Furthermore, the connected personal assistant can communicate with the sensor assembly 100*a*, 100*b* directly via, for example, Bluetooth® compatible signals, and can utilize the home network of the patient to transmit the collected data to cloud, or can communicate directly with the cloud, for example, via a modem/internet connection or a cellular network. Alternatively, the connected personal assistant can be configured to communicate directly with one or both of the base station and the smart device via, for example, Bluetooth® compatible signals, and not configured to communicate directly with the sensor assembly 100*a*, 100*b*.

Along with transmitting collected data to the cloud, one or more of the home base station, the smart device, and the connected personal assistant may also obtain data, commands, or other information from the cloud directly or via the home network. One or more of the home base station, the smart device, and the connected personal assistant may provide some or all of the received data, commands, or other information to the sensor assembly 100*a*, 100*b*. Examples of such information include, but are not limited to, updated configuration information, diagnostic requests to determine if the sensor assembly 100*a*, 100*b* is functioning properly, data collection requests, and other information.

The cloud may include one or more server computers or databases to aggregate data collected from the sensor assembly 100*a*, 100*b*, and in some cases personally descriptive information collected from a patient, with data collected from other intelligent implantable devices, and in some cases personally descriptive information collected from other patients. In this way, the cloud can create a variety of different metrics regarding collected data from each of a plurality of intelligent implantable devices that are implanted into separate patients. This information can be helpful in determining if the intelligent implantable devices are functioning properly. The collected information may also be helpful for other purposes, such as determining which specific devices may not be functioning properly, determining if a procedure or condition associated with the intelligent implantable device is helping the patient (e.g., if a sensor system, which includes a sensor assembly 100*a*, 100*b*, is operating properly), and determining other medical information.

At various times throughout the monitoring process, the patient may be requested to visit a medical practitioner for follow up appointments. This medical practitioner may be the surgeon who implanted the sensor assembly 100*a*, 100*b* in the patient or a different medical practitioner that supervises the monitoring process, physical therapy, and recovery of the patient. For a variety of different reasons, the medical practitioner may want to collect real-time data from the sensor assembly 100*a*, 100*b* in a controlled environment. In some cases, the request to visit the medical practitioner may be delivered through a respective optional bidirectional user interface of each of one or more of the home base station, the smart device, and the connected personal assistant.

A medical practitioner can utilize the doctor office base station, which communicates with the sensor assembly 100*a*, 100*b*, to pass additional data between the doctor office base station and the sensor assembly 100*a*, 100*b*. Alternatively, or in addition, the medical practitioner can utilize the doctor office base station to pass commands to the sensor assembly 100*a*, 100*b*. In some configurations, the doctor office base station can instruct the sensor assembly 100*a*, 100*b* to enter a high-resolution mode to temporarily increase the rate or type of data that is collected for a short time. The high-resolution mode directs the sensor assembly 100*a*, 100*b* to collect different (e.g., large) amounts of data during an activity where the medical practitioner is also monitoring the patient.

In some configurations, the doctor office base station can enable the medical practitioner to input event markers, which can be synchronized with the high-resolution data collected by the sensor assembly 100*a*, 100*b*. For example, assume the sensor assembly 100*a*, 100*b* is a component in a sensor system adapted to be implanted into an intracranial aneurysm. During a follow up visit, the medical practitioner can put the sensor assembly 100*a*, 100*b* in the high-resolution mode. The medical practitioner can review the sensor data from the sensor assembly 100*a*, 100*b* and determine whether the aneurysm is clotting. If the sensor data indicates that the aneurysm is not clotting the medical practitioner can administer medication to the patient. The medical practitioner could administer beta blockers and/or calcium channel blockers to lower the patient's blood pressure and relax their blood vessels. Alternatively, the medical practitioner may administer antifibrinolytic drugs (e.g., aprotinin, tranexamic acid, epsilon-aminocaproic acid) that promote blood clotting. After the medical practitioner administers the medication to the patient, the medical practitioner can click an event marker button on the doctor office base station to mark the administration of the medication. The doctor office base station records the marker and the time at which the marker was input. When the timing of this marker is synchronized with the timing of the collected high-resolution data, the medical practitioner can analyze the data to try and determine the effects of the medication.

In other configurations, the doctor office base station may provide updated configuration information to the sensor assembly 100*a*, 100*b*. The sensor assembly 100*a*, 100*b* can store this updated configuration information, which can be used to adjust the parameters associated with the collection of the data. For example, if the patient is doing well, the medical practitioner can direct a reduction in the frequency at which the sensor assembly 100*a*, 100*b* collects data. On the contrary, if the defect or injury is not healing (e.g., the aneurysm is not clotting), the medical practitioner may direct the sensor assembly 100*a*, 100*b* to collect additional data for a determined period of time (e.g., a few days). The medical practitioner may use the additional data to diagnose and treat a particular problem. In some cases, the additional data may include personally descriptive information provided by the patient after the patient has left presence of the medical practitioner and is no longer in range of the doctor office base station. In these cases, the personally descriptive information may be collected and delivered from via one or more of the home base station, the smart device, and the connected personal assistant. Firmware within the sensor assembly 100*a*, 100*b* and/or the base station can provide safeguards limiting the duration of such enhanced monitoring to insure the battery retains sufficient power to last for the implant's lifecycle. Additionally, or alternatively, the sensor assembly 100*a*, 100*b* can include a conductive switch, which is further described below, that assists in limiting the monitoring of the sensor assembly 100*a*, 100*b*.

In various configurations, the doctor office base station may communicate with a doctor office configuration computing device. The doctor office configuration computing device can include an application with a graphical user interface that enables the medical practitioner to input commands and data. Some or all of the commands, data, and other information may be later transmitted to the sensor assembly 100*a*, 100*b* via the doctor office base station. For example, in some configurations, the medical practitioner can use the graphical user interface to instruct the sensor assembly 100*a*, 100*b* to enter its high-resolution mode. In other configurations, the medical practitioner can use graphical user interface to input or modify the configuration information for the sensor assembly 100*a*, 100*b*. The doctor office configuration computing device can transmit the information (e.g., commands, data, or other information) to the doctor office base station via a wired or wireless network connection (e.g., via a USB connection, Bluetooth® connection, or Wi-Fi connection), which in turn can transmits some or all of the information to the sensor assembly 100*a*, 100*b*.

The doctor office configuration computing device may also display, to the medical practitioner, other information regarding the sensor assembly 100*a*, 100*b*, regarding the patient (e.g., personally descriptive information), or the doctor office base station. For example, the doctor office configuration computing device may display the high-resolution data that is collected by the sensor assembly 100*a*, 100*b* and transmitted to the doctor office base station. The doctor office configuration computing device may also display error information if the sensor assembly 100*a*, 100*b* is unable to store or access the configuration information, if the sensor assembly 100*a*, 100*b* is unresponsive, if the sensor assembly 100*a*, 100*b* identifies an issue with one of the sensors or radio, if the doctor office base station is unresponsive or malfunctions, or for other reasons.

In some configurations, doctor office configuration computing device may have access to the cloud. In at least one embodiment, the medical practitioner can utilize the doctor office configuration computing device to access data stored in the cloud, which was previously collected by the sensor assembly 100*a*, 100*b* and transmitted to the cloud via one or both of the home base station and the smart device. Similarly, the doctor office configuration computing device can transmit the high-resolution data obtain from the sensor assembly 100*a*, 100*b* via the doctor office base station to the cloud. In some configurations, the doctor office base station may have internet access and may be enabled to transmit the high-resolution data directly to the cloud without the use of the doctor office configuration computing device.

In various configurations, the medical practitioner may update the configuration information of the sensor assembly 100*a*, 100*b* when the patient is not in the medical practitioner's office. In these cases, the medical practitioner can utilize the doctor office configuration computing device to transmit updated configuration information to the sensor assembly 100*a*, 100*b* via the cloud. One or more of the home base station, the smart device, and the connected personal assistant can obtain updated configuration information from the cloud and pass updated configuration information to the cloud. This can allow the medical practitioner to remotely adjust the operation of the sensor assembly 100*a*, 100*b* without needing the patient to come to the medical practitioner's office. This may also permit the medical practitioner to send messages to the patient in response, for example, to personally descriptive information that was provided by the patient and passed through one or more of the home base station, the smart device, and the connected personal assistant to the doctor office base station.

Although the doctor office base station and the doctor office configuration computing device are described as separate devices, configurations are not so limited; rather, the functionality of the doctor office configuration computing device and the doctor office base station may be included in a single computing device or in separate devices (as illustrated). In this way, the medical practitioner may be enabled in one configuration to input the configuration information or markers directly into the doctor office base station and view the high-resolution data (and synchronized marker information) from a display on the doctor office base station.

Still referring to FIG. 1, alternate configurations are contemplated. For example, each of the base station, the smart device, and the connected personal assistant may be configured to communicate with one or both of the sensor assembly 100*a*, 100*b* and the cloud via another one or two of the base station, the smart device, and the connected personal assistant. Moreover, the smart device can be temporarily contracted as an interface to the sensor assembly 100*a*, 100*b*, and can be any suitable device other than a smart phone, such as a smart watch, a smart patch, and any IoT device, such as a coffee pot, capable of acting as an interface to the sensor assembly 100*a*, 100*b*. In addition, one or more of the base station, smart device, and connected personal assistant can act as a communication hub for multiple sensor assemblies 100*a*, 100*b* implanted in one or more patients. Furthermore, one or more of the base station, smart device, and connected personal assistant can automatically order or reorder prescriptions or medical supplies (e.g., a calcium channel blocker) in response to patient input or sensor assembly 100*a*, 100*b* input (e.g., pain level, level of clotting) if a medical professional and insurance company have preauthorized such an order or reorder; alternatively, one or more of the base station, smart device, and connected personal assistant can be configured to request, from a medical professional or an insurance company, authorization to place the order or reorder. Moreover, one or more of the base station, smart device, and connected personal assistant can be configured with a personal assistant such as Alexa® or Siri®.

II. Sensor Assembly

Figure 2A:
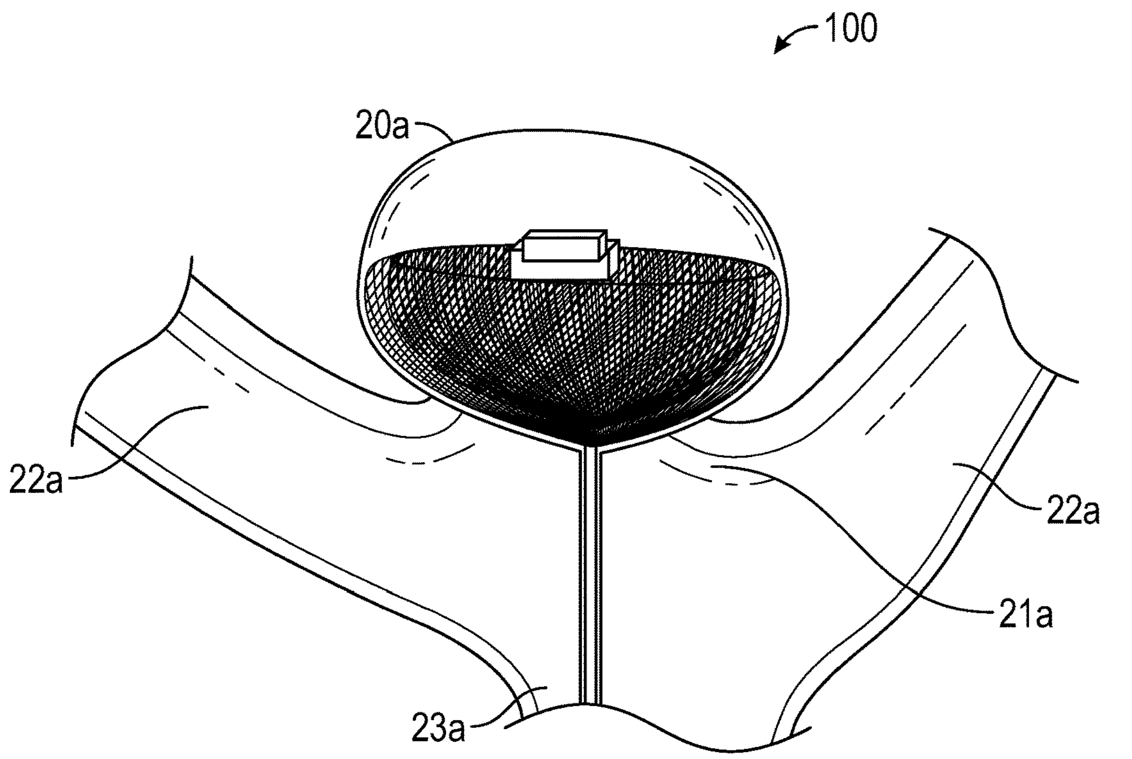
FIGS. 2A and 2B illustrates example sensor assemblies implanted in an aneurysm, according to certain aspects of the present disclosure.
Figure 2B:
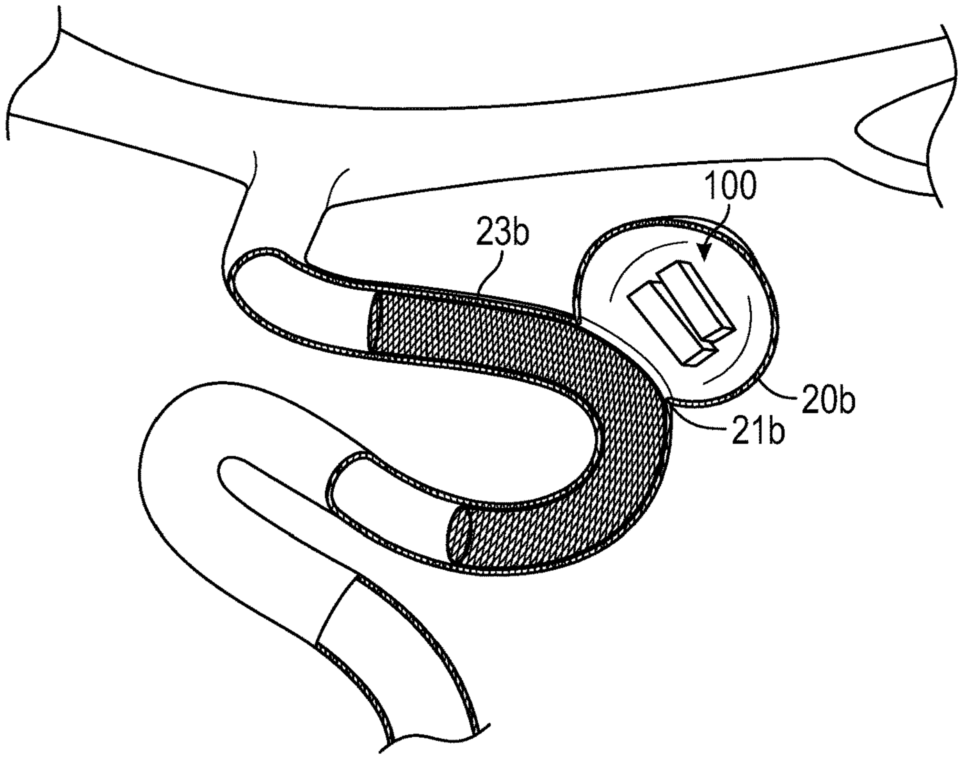

FIGS. 2A and 2B illustrate different types of aneurysms. FIG. 2A illustrates a bifurcation aneurysm 20A. The neck 21A of the bifurcation aneurysm 20A is positioned at the bifurcation between a parent artery 23A and two daughter branches 22A. Bifurcation aneurysms 20A can be particularly dangerous because the bifurcation creates greater pressure on the aneurysm. FIG. 2B illustrates a sidewall aneurysm 20B. The sidewall aneurysm 20B includes a neck 21B at or near the transition between the parent artery 23B and the sidewall aneurysm 20B.

The sensor assemblies 100 described herein are capable of being implanted within any vascular structure, including the types of aneurysms shown in FIGS. 2A and 2B.

Figure 3A:
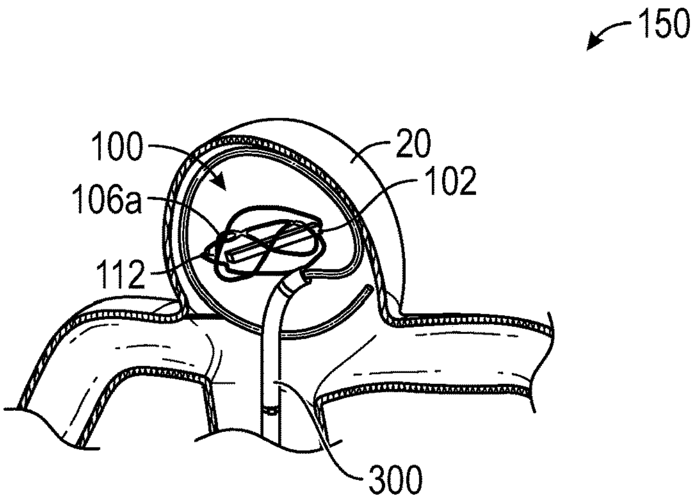
FIGS. 3A, 3B, and 3C illustrate different example sensor systems implanted in an aneurysm, according to certain aspects of the present disclosure.
Figure 3B:
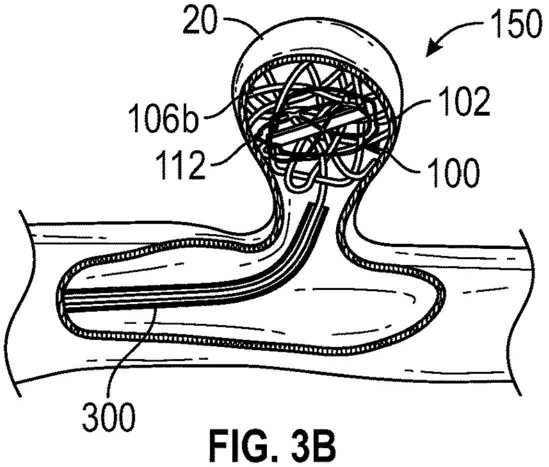
Figure 3C:
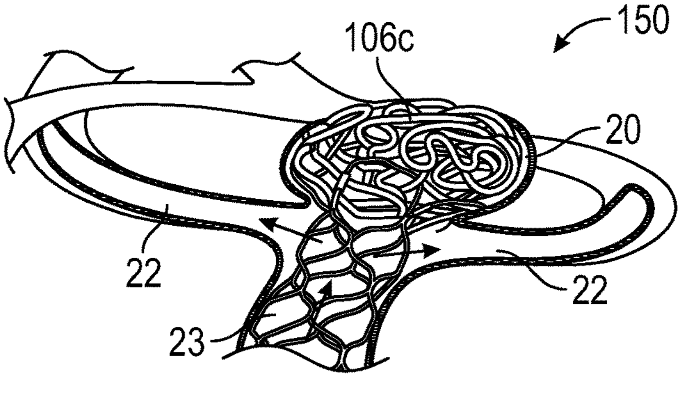

As shown in FIGS. 3A-3C, the sensor assembly 100 can include one or more sensors 102 and/or one or more antennas 112. The one or more sensors 102 can monitor one or more physiological parameters. The one or more physiological parameters may be indicative of blood flow through a vascular system of a patient or other conditions of the patient. For example, the one or more sensor 102 can monitor the one or more physiological parameters continuously, intermittently at a regular time interval, or upon command. The one or more antennas 112 can transmit the sensor data to a receiver outside the patient's body. For example, the one or more antennas 112 can transmit sensor data continuously, intermittently at a regular time interval, or upon command.

The sensor assembly 100 can monitor one or more physiological parameters indicative of blood flow through a vascular structure, such as an aneurysm 20 as shown in FIGS. 3A-3C. The sensor assembly 100 may include one or more sensors to monitor other conditions of the patient, such as movement. For example, the sensor assembly 100 may include an accelerometer to monitor whether the patient is standing or laying down.

The sensor assembly 100 may be included in a sensor system 150, which can also include an anchoring structure 106. For example, FIG. 3A illustrates a sensor system 150 being implanted into an aneurysm 20 by a delivery system 300. Anchor structure 106A may be positioned between the sensor assembly 100 and a wall of the aneurysm 20. The anchor structure 106A may take the form of one or more framing coils or other structures to maintain an entrance of the aneurysm and/or stabilize the aneurysm. For example, the anchor structure 106A may at least partially surround sensor assembly 100 and contact the wall of the aneurysm 20. Viewed another way, the sensor assembly 100 may be disposed within an interior space defined by the anchor structure 106A. The anchor structure 106A may directly or indirectly contact the sensor assembly 100. For example, the anchor structure 106A may contact the antenna 112 and/or the sensor 102. In some configurations, the anchor structure 106A may be directly or indirectly coupled to the sensor assembly 100. In other configurations, the anchor structure 106A may not contact the sensor assembly 100 at all.

The anchor structure may take on different configurations. For example, FIG. 3B shows a sensor system 150 being implanted into an aneurysm 20. The anchor structure 106B may take the form of a mesh or woven structure such as a basket. The anchor structure 106B may take the form of multiple loops that extend from the sensor system, e.g., two loops or three loops or four loops or more than four loops. Optionally, the multiple loops lie within a single plane. Optionally, the multiple loops are each of the same size. The anchor structure 106B may contact the wall of the aneurysm 20. FIG. 3C illustrates a sensor system 150 after it has been implanted in a bifurcation aneurysm 20 with an anchor structure 106C. The anchor structure 106C may include one or more coils to promote occlusion. After the sensor system 150 is implanted in the aneurysm 20, the blood can flow from a parent vessel 23 into associated daughter vessels 22 (as indicated by the arrows). The sensor system 150 can block blood from flowing into the aneurysm 20, which reduces the likelihood that the aneurysm 20 will grow.

Figure 4:
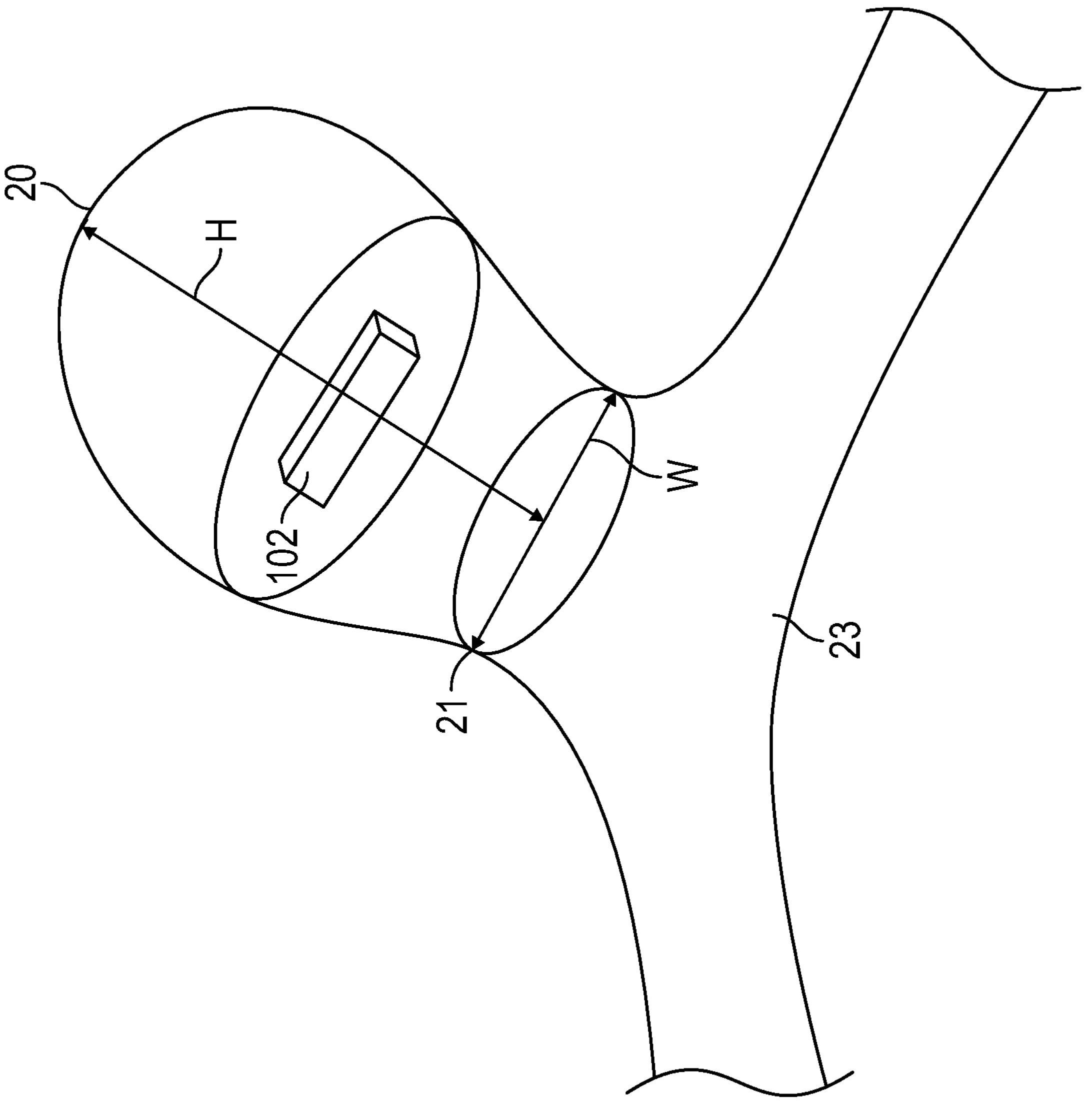
FIG. 4 illustrates an example sensor implanted in an aneurysm, according to certain aspects of the present disclosure.

FIG. 4 illustrates possible positioning of the sensor 102 or sensor assembly 100 within an aneurysm 20. As shown in FIG. 4, the aneurysm 20 may have a neck 21, which can be located adjacent a parent artery 23. The aneurysm 20 may have a height H and the neck 21 may have a width W. The sensor 102 can be positioned at or near a middle of the height H of the aneurysm 20 and a middle of the width W of the neck 21. The positioning of the one or more sensors 102 or the sensor assembly 100 is important. For example, if the sensor 102 is positioned too far from the parent vessel 23, the sensor 102 may not be able to sense the blood flow. If the sensor 102 is positioned too close to the neck 21, the sensor 102 may cause unwanted blockages and other problems in treatment. Moreover, the sensor 102 may inadvertently flow out of the aneurysm 20 by, for example, the blood flow in the parent vessel 23.

A. Antenna(s)

As previously described, the sensor assembly 100 can include one or more antennas 112. The antenna 112 may be in electrical communication with the one or more other components of the sensor assembly 100, for example the sensor 102. The antenna 112 can transmit sensor data or other data related to the sensor assembly 100 to a receiver (e.g., a hub within the body and/or a base station or other computing device outside the body). For example, the antenna 112 can continuously transmit sensor data or intermittently transmit sensor data at predetermined time intervals or upon receipt of a command. The antenna 112 can be adapted to receive data from an external transmitter (e.g., a hub within the body and/or a base station or other computing device outside the body). The antenna 112 may include or act as a RF transceiver, which can be a conventional transceiver that is configured to allow the sensor assembly 100 to communicate with a base station (not shown in FIGS. 5A-5C) configured for use with the sensor assembly 100. For example, the antenna 112 can be any suitable type of transceiver (e.g., Bluetooth®, Bluetooth® Low Energy (BTLE), and WiFi®), can be configured for operation according to any suitable protocol (e.g., MICS, ISM, Bluetooth®, Bluetooth® Low Energy (BTLE), Zigbee, and WiFi®), and can be configured for operation in a frequency band that is within a range of 1 MHz-5.4 GHz, or that is within any other suitable range.

The antenna 112 can include a filter (not shown). The filter can be any suitable bandpass filter, such as a surface acoustic wave ("SAW") filter or a bulk acoustic wave ("BAW") filter. The antenna 112 can be suitable for the frequency band in which the RF transceiver and/or the antenna 112 generates signals for transmission by the antenna 112, and for the frequency band in which a base station generates signals for reception by the antenna 112.

The antenna 112 may be constructed from one or more materials (e.g., pure or alloy material). For example, the antenna 112 can be constructed from one or more of the following: platinum iridium, platinum, or a coated shape memory wire. The coated shape memory wire can include an inner nitinol wire coated and/or plated with an electrically/RF signal conductive material that can work in frequencies from 2 MHz-500 Mhz. The one or more materials can have a conductivity between $1.0\text{-}6.0\times10^{6}$ S/M. The one or more materials can be adapted to interact with or be neutral to the sensor 102, as the sensor 102 interacts with a treatment zone.

The antenna 112 can be sufficiently flexible, pliable, and/or conformable such that the sensor assembly 100 can transition between a compressed configuration and an expanded configuration. For example, the antenna 112 can include a flex parylene antenna. The one or more antennas 112 can be compressed into the compressed configuration and loaded into a delivery system. Moreover, once the antenna 112 are implanted into the patient, the antenna 112 may expand into the expanded configuration and temporarily anchor the sensor assembly 100 within the patient (e.g., in or near a treatment zone). In the expanded configuration, the antenna 112 can be sized and adapted to conform to the inner surface of or near the treatment zone (e.g., the inner surface of an aneurysm).

The antenna 112 can form the anchoring structure for the sensor system 150. The antenna 112 can include a single axis loop, a dual axis loop, or a spherical loop to enhance the capability of contact with the vascular structure or other anchoring structure. The antenna can locate the sensor assembly 100 in the patient (e.g., a position about the aneurysm neck entrance). When the sensor assembly 100 is implanted in a patient, the antenna 112 can, for example, interact with an aneurysm wall and act as an anchor contact with the aneurysm to maintain a position of the sensor assembly 100 for adequate monitoring of the fluid exchange between the aneurysm and the associated parent artery. For example, the antenna 112 may include one or more prongs and/or prong extensions that can interact with the inner wall of the aneurysm. The one or more prongs and/or prong extensions can rounded ends such that the prongs and/or prong extensions are atraumatic. Alternatively, a separate anchoring structure 106 can be added to support the sensor assembly 100 in the patient. In those configurations, the separate anchoring structure 106 can directly or indirectly contact or couple to the antenna 112. The antenna 112 can be deployed such that the antenna does not obstruct the implantation of the separate anchoring structure 106. The separate anchoring structure 106 can conform to the inner surface of or near the treatment zone.

The antenna 112 or other component of the sensor assembly 100 may be manufactured to carry a material that complements or inhibits the interaction desired by the treatment method, as further described below with respect to the one or more sensor(s). For example, the antenna 112 can be coated with the degradable material on the outside or inside of the antenna(s) 112, which can release some of the material or other byproducts of the material's degradation into the treatment site. For example, the materials or other byproducts may be released based on a conductivity switch, which is further described below in relation to the Sensor System. The antenna(s) 112 can act as a coil implant for the sensor 102 and work in conjunction with the coils or spherical implants to fill and obstruct flow into and about the aneurysm zone.

FIGS. 5A to 5D show different configurations of the sensor assembly 100. The antenna 112 may be in electrical communication with the sensor 102. The antenna 112 may be on the same chip or a different chip as the sensor 102. As mentioned above, the sensor assembly 100 may be capable of transitioning between a compressed configuration and an expanded configuration. For example, the one or more antenna 112 may be compressed about the sensor 102 and/or carrier 104 for loading into a delivery system and expanded upon release from the delivery system. In the expanded configuration, the antenna 112 may provide stabilizing or anchoring functionality.

Figure 5A:
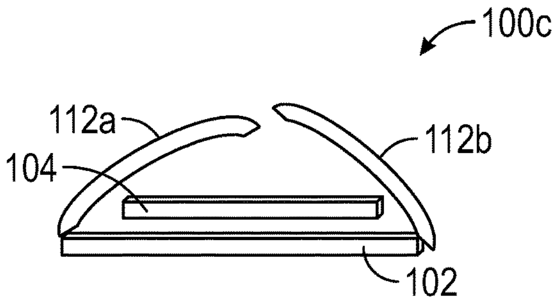
FIGS. 5A, 5B, 5C, and 5D illustrates schematic representations of example sensor assemblies, according to certain aspects of the present disclosure.

As shown in FIG. 5A, the sensor assembly 100*c* can include one or more sensors 102, a carrier 104, and/or one or more antennas 112*a*, 112*b*. The one or more antennas 112*a*, 112*b* can be flexible such that the antennas 112*a*, 112*b* can be compressed about the sensor 102 and/or carrier 104. The one or more antennas 112*a*, 112*b* can at least partially surround the one or more sensors 102 and/or the carrier 104. As illustrated, the sensor 102 may be disposed on a first side of the carrier 104, and the antenna 112*a*, 112*b* disposed on an opposite side of the carrier 104. Together, the sensor 102 and the antenna 112*a*, 112*b* substantially surround the carrier 104.

Figure 5B:
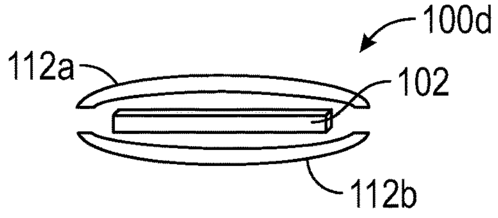

As shown in FIG. 5B, the sensor assembly 100*d* can include one or more antennas 112*a*, 112*b* at least partially surrounding the sensor 102. For example, the sensor 102 can be positioned between the first and second antennas 112*a*, 112*b*. The first antenna 112*a* may be disposed on a first side of the sensor 102 and the second antenna 112*b* may be disposed on an opposite side of the sensor 102.

Figure 5C:
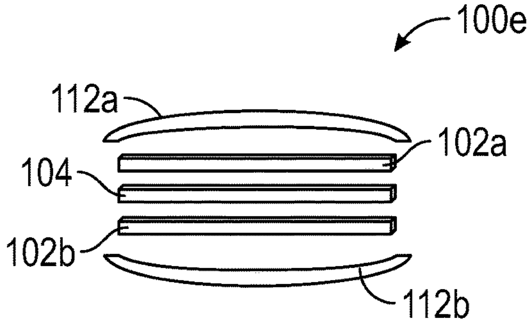

As shown in FIG. 5C, the sensor assembly 100*e* can includes one or more sensors 102*a*, 102*b* supported by a carrier 104. For example, the carrier 104 may be positioned between the sensors 102*a*, 102*b*. A first sensor 102*a* may be disposed on a first side of the carrier 104. A second sensor 102*b* may be disposed on an opposite side of the carrier 104. The one or more antennas 112*a*, 112*b* may at least partially surround the one or more sensors 102*a*, 102*b* and/or the carrier 104. A first antenna 112*a* may be disposed on a first side of the carrier 104. A second antenna 112*b* may be disposed on an opposite side of the carrier 104. Each sensor 102*a*, 102*b* may be positioned between the carrier 104 and an antenna 112*a*, 112*b*.

Figure 5D:
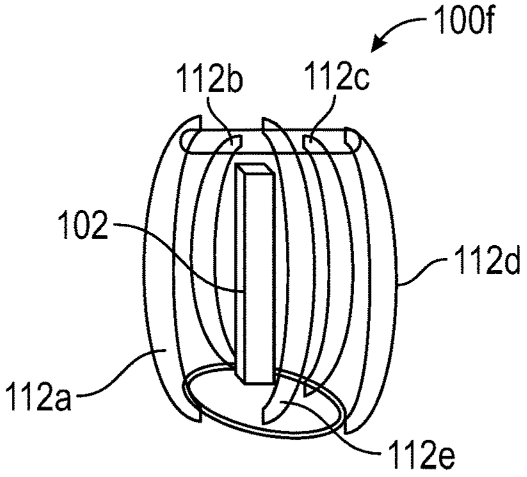

As shown in FIG. 5D, the sensor assembly 100*f* can include one or more antennas 112*a*-112*e* forming a spherical structure that at least partially encloses the one or more sensors 102. The antenna(s) 112*a*-122*e* can be wrapped around the one or more sensors 102. The one or more antennas 112*a*-112*e* may be connected at either end.

Figure 10A:
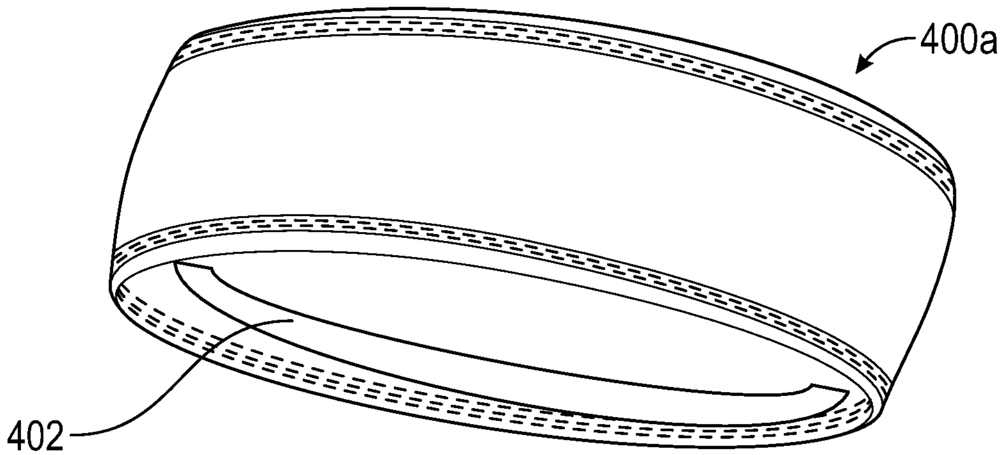
FIGS. 10A and 10B illustrate different wearables that can interact with the sensor assemblies disclosed.
Figure 10B:
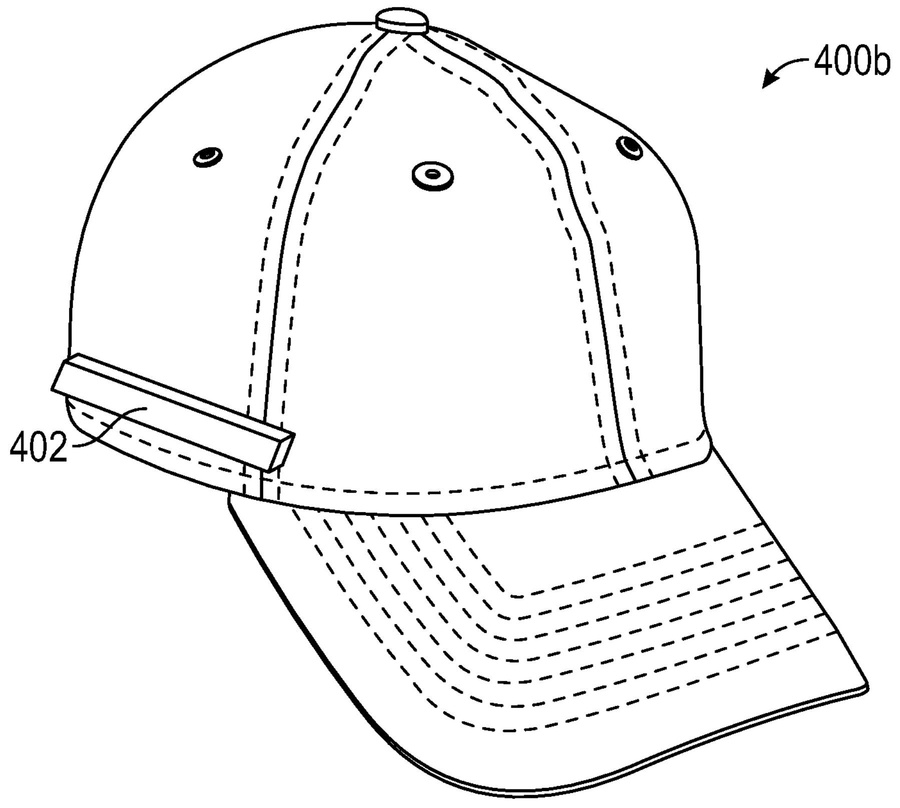

In some configurations, the size of the antenna 112 may limit the transmission distance. The sensor system 150 may include an additional transceiver within the patient's body or external the patient's body to extend transmission. For example, the transceiver may be integrated into a wearable device or clothing. As shown in FIGS. 10A and 10B, the sensor assembly 100 can be adapted to communicate with an external transceiver 402. The external transceiver 402 can be attached to a user interface of a continuous positive airway pressure ("CPAP") machine, a headband 400*a*, a hat 400*b*, or other wearables. The external transceiver 402 can be adapted to receive one or more signals (e.g., RF signals) from the sensor assembly 100. The external transceiver 402 can include a self-contained battery or battery and capacitor. The external transceiver 402 can be adapted to communicate with a receiving platform, such as a base station or other computing device. For example, the external transceiver 402 can be indirectly or directly connected to the base station for downloading and transferring the generated information to the cloud.

B. Sensor

Still referring to FIGS. 5A, 5B, 5C and 5D and as previously described, the sensor assembly 100 can include one or more sensors 102. "Sensor" refers to a device that can be utilized to do one or more of detect, measure and/or monitor: one or more different aspects of a body tissue (e.g., anatomy, physiology, metabolism, and function); one or more aspects of body or body segment condition or function (e.g., clotting in an aneurysm); and/or one or more aspects of the sensor assembly 100.

Representative examples of sensors suitable for use within the sensor assembly 100 include, for example, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), impedance sensors, electrodes, accelerometers, gyroscopes, mechanical stress sensors and temperature sensors. Within certain configurations, at least one sensor of the one or more sensors 102 can be a wireless sensor, or, within other configurations, connected to a wireless microprocessor. Within some configurations, at least one sensor of the one or more sensors 102 can have a Unique Sensor Identification number ("USI"), which specifically identifies the sensor.

The one or more sensors 102 may be configured to detect, measure and/or monitor information relevant to the state of the sensor assembly 100 after implantation. The state of the sensor assembly 100 may include the integrity of the sensor assembly 100, the movement of the sensor assembly 100, the forces exerted on the sensor assembly 100 and other information relevant to the implanted sensor assembly 100.

The one or more sensors 102 may be configured to detect, measure and/or monitor information relevant body tissue (e.g., one or more physiological parameters of a patient) after implantation of the sensor assembly 100. Body tissue monitoring may include blood pressure, pH level, oxygen, carbon dioxide, potassium, iron, and/or glucose in the blood of the patient. The one or more sensors 102 can include fluid pressure sensors, fluid volume sensors, pulse pressure sensors, blood volume sensors, blood flow sensors, chemistry sensors (e.g., for blood and/or other fluids), metabolic sensors (e.g., for blood and/or other fluids).

A radiopaque marker, or other type of marker, can be integrated with the one or more sensors 102. The radiopaque marker can track a location of the one or more sensors 102 within the vasculature with standard fluoroscopy techniques.

Figure 6:
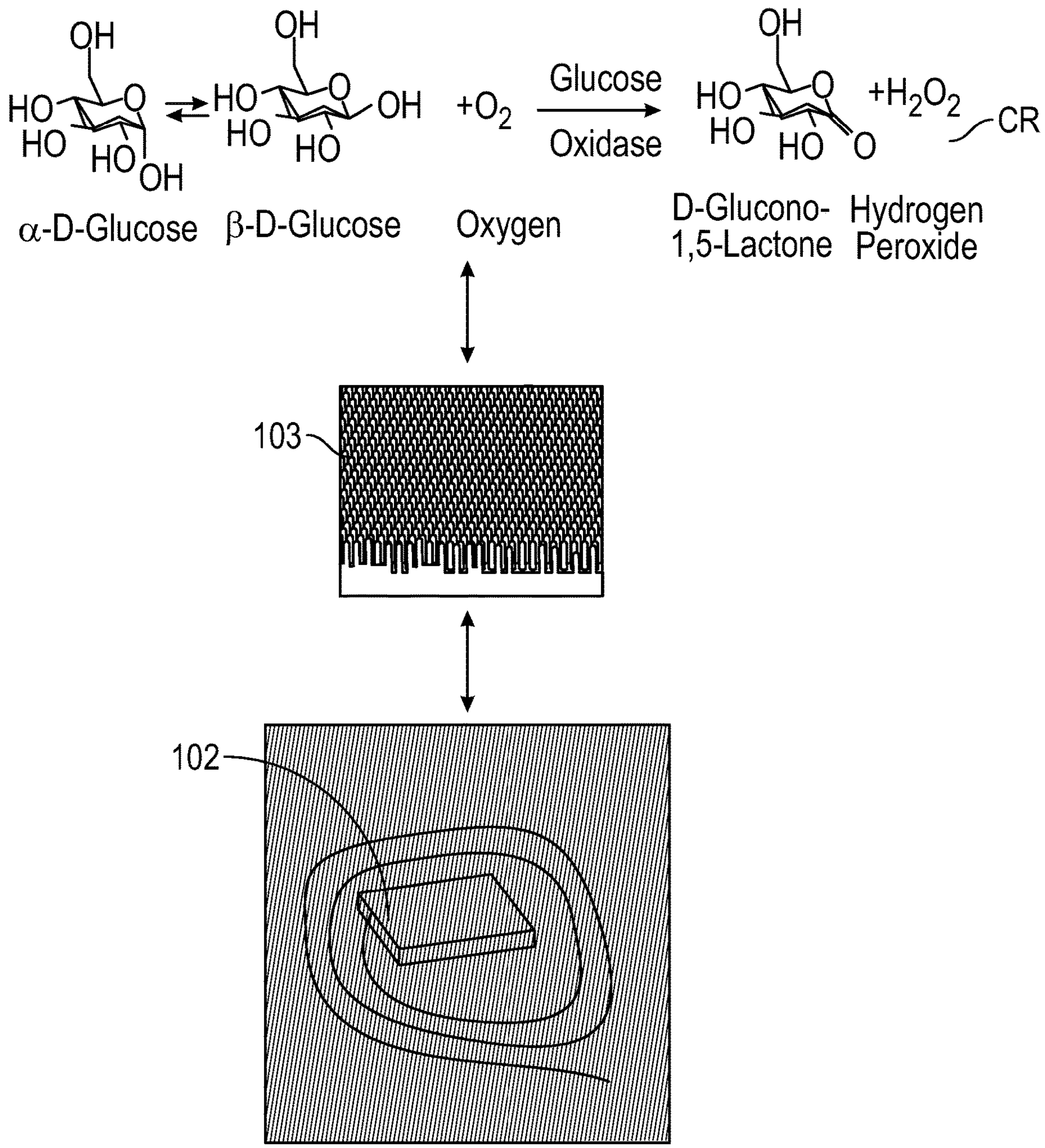
FIG. 6 illustrates details of a surface of an example sensor, according to certain aspects of the present disclosure.

As shown in FIG. 6, at least one of the one or more sensors 102 can include a sensing mechanism based on a chemical reaction CR. For example, the sensor(s) 102 can include an outer membrane 103 including a specific stoichiometry and analyte perfusion rate sufficient to manage the chemical reaction CR on the sensor(s) 102 and the resultant output interaction on a platinum surface, such as th e antenna(s) 112, that generates a signal for transmission and monitoring of the zone. The antenna(s) 112 may extend from the sensor(s) 102. The signal can determine the chemical reaction CR is in a mode of action of decreasing action or increasing action of the biological transmission of blood from the parent artery to the aneurysm, a void, through a broken containment method for used on addressing an aneurysm closing treatment, cancer, an embolic treatment, an embolic vessel closing treatment (artery or vein), or the like.

The duration of the chemical reaction CR can be greater than or equal to one day and/or less than or equal to 360 days. For example, the duration can be greater than or equal to one day and/or less than or equal to 180 days. The duration can be greater than or equal to one day and/or less than or equal to about 90 days. The duration can be greater than or equal to one day and/or less than or equal to about 30 days. The duration can be greater than or equal to one day and/or less than or equal to about 10 days. The data output variability of the chemical reaction CR can range from a small deviation of 1% to a significant deviation or greater than 99% based on a measurement indication of whether there is a chemical reaction CR or no chemical reaction CR. For example, a conductivity switch or sensor can be used, which is further described below. Based on the chemical interaction, the sensor(s) 102 can detect the resulting biological reaction, which can be used to determine a measurement of biological flow reduction/restriction, biological flow impaction and/or biologic seal. The degradation and/or non-degradation of the signal can be a determination of a function of a treatment in the area/zone in which the sensor assembly 100 and/or the sensor system 150 is placed.

C. Processor/Controller

The sensor assembly 100 may include a processor in electrical communication with the one or more sensors 102 and/or the antenna(s) 112. The one or more sensors 102 and the processor can be located on a printed circuit board. Alternatively, some or all of the one or more sensors 102 may be located in or on another structure of the sensor assembly 100 separate from the printed circuit board. The processor, which can be any suitable microcontroller or microprocessor, can be configured to control the configuration and operation of one or more of the other components of the sensor assembly 100. For example, the processor can be configured to control the one or more sensors 102 to sense relevant measurement data or physiological parameters, to store the measurement data generated by the one or more sensors in a memory, to generate messages, include the stored data as a payload, to packetize the messages, to provide the message packets to the antenna(s) 112 for transmission to a receiver (e.g., hub in the patient's body or a base station or other computing device outside the patient's body). The processor can be configured to execute commands received from a base station or other computing device via the antenna(s) 112. For example, the processor can be configured to receive configuration data from the base station, and to provide the configuration data to the component of the sensor assembly 100 to which the base station directed the configuration data. If the base station directed the configuration data to the processor, then the processor can configure itself in response to the configuration data.

The processor can cause the one or more sensors 102 to measure, to detect, to determine if a measurement is a qualified or valid measurement, to store the data representative of a valid measurement, and to cause the antenna(s) 112 to transmit the stored data to a base station or other source external to the sensor assembly 100. In response to being polled by a base station or by another device external to the sensor assembly 100, the processor can generate conventional messages having payloads and headers. The payload scan include the stored samples of the signals that the one or more sensors 102 generated. The headers can include the sample partitions in the payload, a time stamp indicating the time at which the sensor 102 acquired the samples, an identifier (e.g., serial number) of the sensor assembly 100, and/or a patient identifier (e.g., a number or name).

The processor can generate data packets that include the messages according to a conventional data-packetizing protocol. Each packet can also include a packet header that includes, for example, a sequence number of the packet so that the receiving device can order the packets properly even if the packets are transmitted or received out of order. The processor can encrypt some or all parts of each of the data packets, for example, according to a conventional encryption algorithm, and error encodes the encrypted data packets. For example, the processor can encrypt at least the sensor assembly 100 and patient identifiers to render the data packets compliant with the Health Insurance Portability and Accountability Act ("HIPAA"). The processor can provide the encrypted and error-encoded data packets to the antenna(s) 112, which, via the filter, transmits the data packets to a destination, such as the base station 4 (shown in FIG. 1) or a receiver external to the sensor system 150. The antenna(s) 112 can transmit the data packets according to any suitable data-packet-transmission protocol.

Alternate configurations of the sensor assembly 100 and/or the sensor system 150 are contemplated. For example, the antenna(s) 112 can perform encryption or error encoding instead of, or complementary to, the processor. Furthermore, the sensor assembly 100 and the sensor system 150 can include components other than those described herein and can omit one or more of the components described herein.

The sensor assembly 100 may include a memory circuit (not shown) that can be any suitable nonvolatile memory circuit, such as EEPROM or FLASH memory. The memory can be in electrical communication with the processor, the antenna(s) 112, and/or the one or more sensors 102. The memory can be configured to store data written, for example, by the processor or the antenna(s) 112, and to provide data in response to a read command from the processor.

D. Power Source

The sensor assembly 100 can include one or more power sources. For example, the sensor assembly can include one or more batteries and/or supercapacitors. The power source may be sized to fit within the vascular structure with the remainder of the sensor assembly 100. In other configurations, the sensor assembly 100 may be powered by a power source at a remote location from the vascular structure, either in the patient's body or outside the patient's body.

The power source can be any suitable battery, such as a Lithium Carbon Monofluoride (LiCFx) battery or solid state battery, or other storage cell capable of storing energy (e.g., a supercapacitor) for powering the processor for an expected lifetime of the sensor assembly 100 (e.g., at least one month or at least six months). The power source may receive sufficient energy from the sensor reaction by-product to maintain a minimal power capacity for sustaining micro-controller memories, real time clocks and/or SRAMs sleep modes.

Replacing a power source implanted in a patient is often desirable at least because it involves an invasive procedure that can be relatively expensive and that can have adverse side effects, such as infection and soreness. Thus, the power source may be rechargeable. For example, the power source may be recharged using integrated circuitry on an ASIC chip. As another example, the battery may be charged inductively. The wearable clothing shown in FIGS. 10A and 10B or other wearable medical devices (e.g., CPAP devices) may be adapted to facilitate inductive charging.

E. Sensor Assembly Configuration

FIGS. 7A, 7B, 7C, 7D, 8A, 8B, 8C, 9A and 9B illustrate different configurations of the sensor assembly that can be used in any of the systems and methods described herein. Although the examples below may be described with specific types of sensors, the sensor configurations described below may be used with other chemical interactions or types of sensors.

Figure 7A:
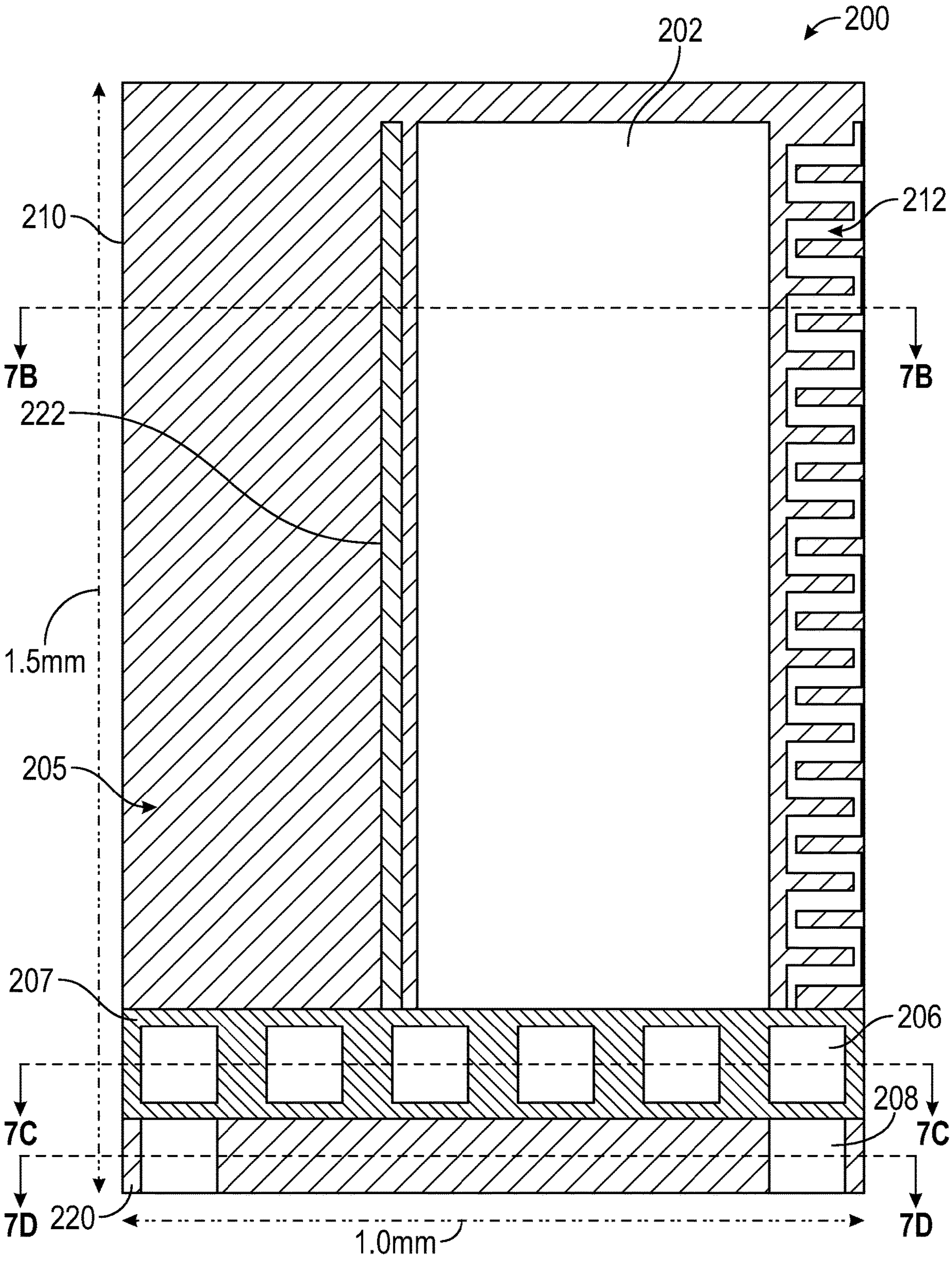
FIG. 7A illustrates a top down schematic view of certain components of an example sensor assembly, according to certain aspects of the present disclosure.
Figure 7B:
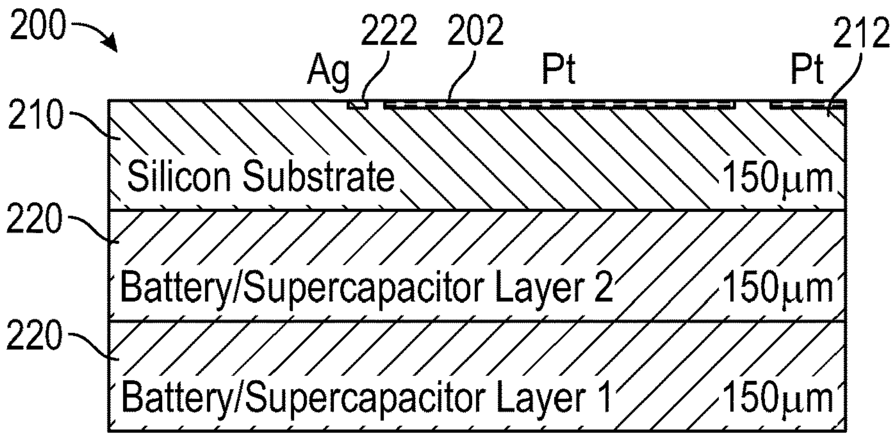
FIGS. 7B, 7C, and 7D illustrate cross-sections of the sensor assembly shown in FIG. 7A.
Figure 7C:
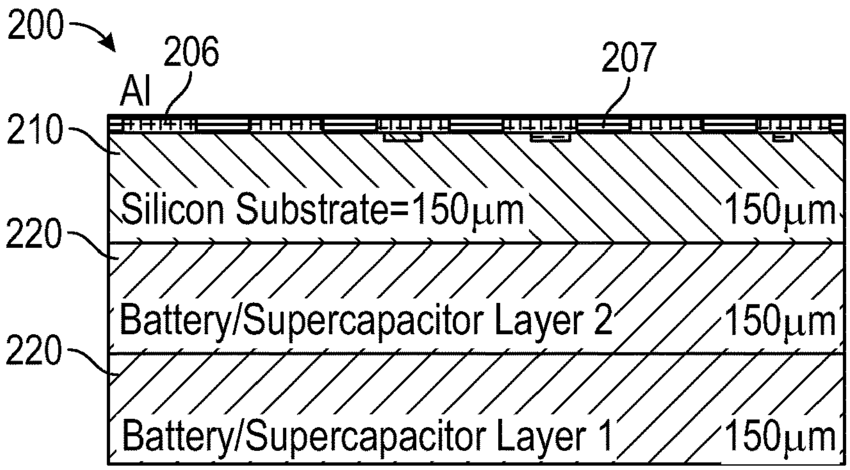
Figure 7D:
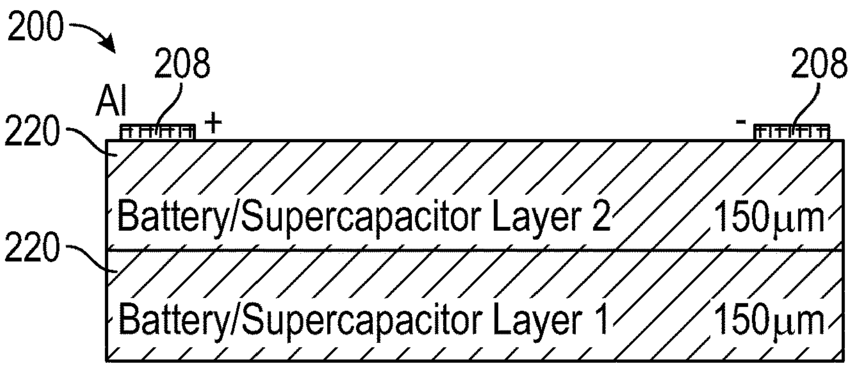

FIG. 7A illustrates a top-down schematic view of the sensor assembly 200. FIGS. 7B, 7C and 7D illustrate schematic, cross-sectional views of the sensor assembly 200 depicted in FIG. 7A. The cross-sections are taken along the lines shown in FIG. 7A. The sensor assembly 200 can have a length and/or width that is less than or equal to about 1.5 mm or less than or equal to about 1.0 mm. A thickness of the sensor assembly 200 may be less than or equal to 500 microns or less than or equal to 300 microns.

The sensor assembly 200 can include a substrate layer 210, for example a silicon substrate, for attaching components. The substrate layer 210 can be stacked on the power source 220 (see FIGS. 7B and 7C).

The sensor assembly 200 can include one or more antennas 212 and one or more sensors 202 (e.g., a glucose sensor, oxygen sensor, metabolic sensor, motion sensors, or other sensor described herein). As illustrated, the sensor 202 and/or the antenna 212 may include platinum, a platinum alloy, gold, silver, or other suitable materials (see FIG. 7B). Optionally, the sensor assembly 200 can include a reference electrode or balancer 222 to clean the signal. The reference electrode 222 can include a precious metal such as silver or silver oxide. A region 205 of the substrate layer 210 may be kept clear for die attachment of additional devices.

The sensor assembly 200 can include one or more contact pads 206 for component linking. The contact pads 206 may be carried by an insulation layer 207 (see FIG. 7C). The sensor assembly 200 can include one or more ground pads 208 for circuit conduit and switch interaction. The ground pads 208 may be carried by the power source 220 (see FIG. 7D). As illustrated, the contact pads 206 may be positioned between the ground pads 208 and the sensor 102.

As shown in FIGS. 7B, 7C and 7D, the sensor assembly 200 may include a power source 220. For example, the power source 220 may include one or more batteries and/or supercapacitors. Each battery or supercapacitor may have a thickness of less than or equal to about 150 μm.

Figure 8A:
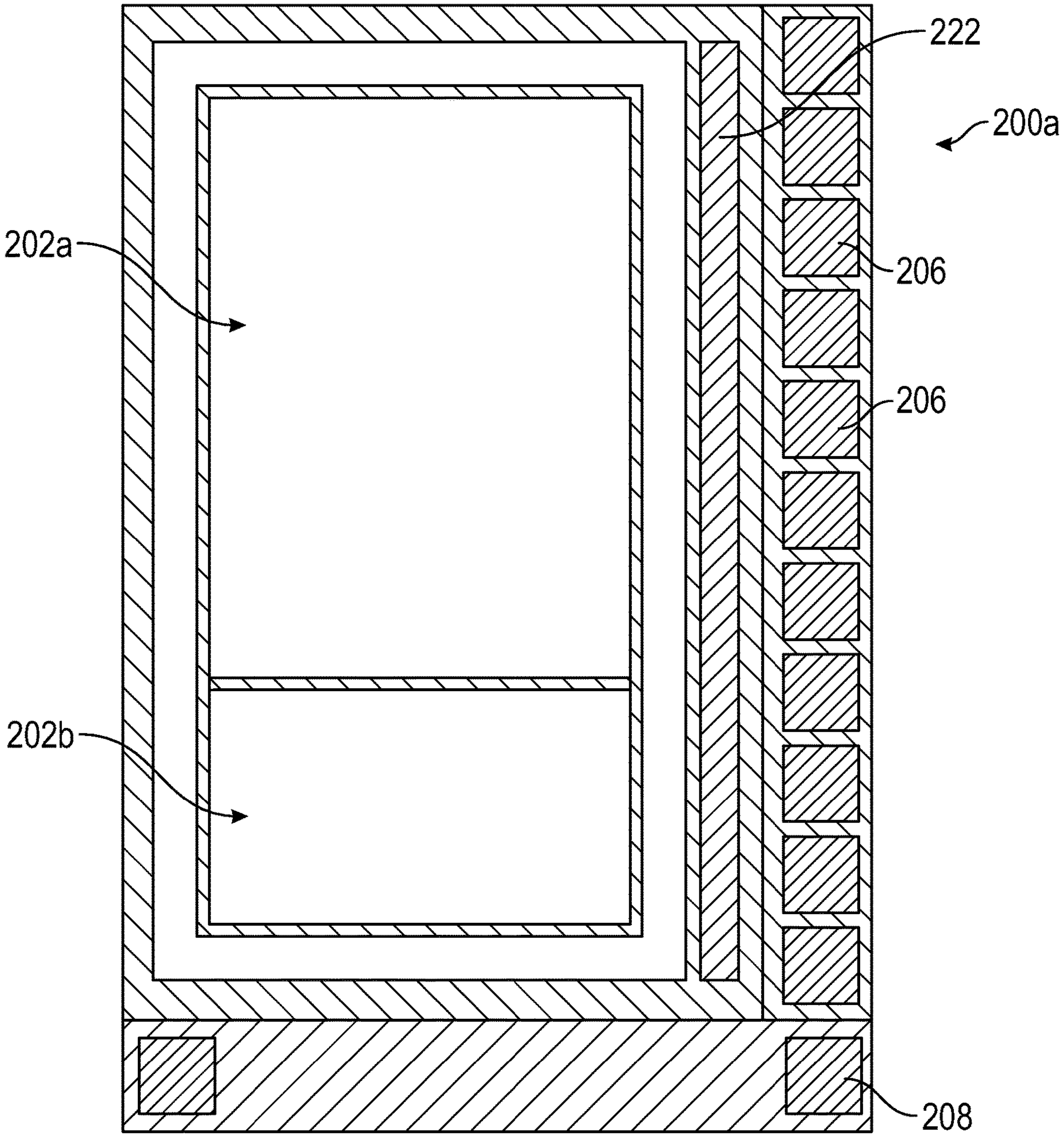
FIG. 8A illustrates a top down schematic view of certain components of an example sensor assembly, according to certain aspects of the present disclosure.
Figure 8B:
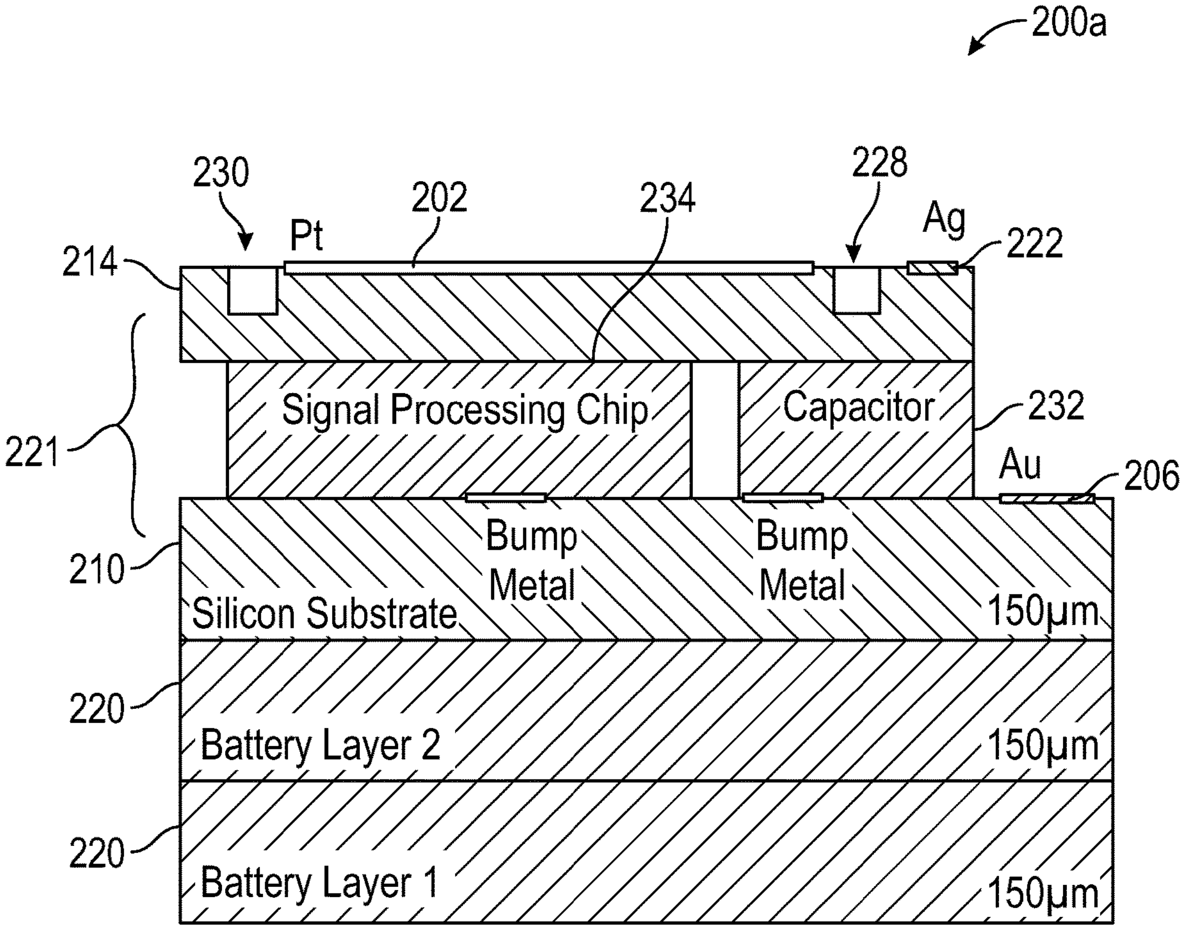
FIG. 8B illustrates a cross-section of the sensor assembly shown in FIG. 8A.

FIG. 8A illustrates a top-down schematic view of the sensor assembly 200*a*. FIG. 8B illustrates a cross-section of the sensor assembly 200*a*. The sensor assembly 200*a* can include any of the features described above with respect to the sensor assembly 200.

The sensor assembly 200*a* can include two sensors 202*a*, 202*b*. For example, a first sensor 202*a* can be a glucose sensor and a second sensor 202*b* can be an oxygen sensor. The glucose sensor 202*a* can include a platinum or platinum alloy pad. The glucose sensor 202*a* can have a surface area of 0.5 $mm^2$ or greater. The oxygen sensor 202*b* can include a pad with oxygen base oxidase. The glucose sensor pad 202*a* can have a greater surface area than the oxygen sensor pad 202*b*. For example, the surface area of the glucose sensor pad 202*a* can be at least two times or at least three times greater than the surface area of the oxygen sensor pad 202*b*. The surface area of the glucose sensor pad 202*a* can be at least five times or at least ten times greater than the surface area of the reference electrode 222.

The sensor assembly 200*a* can include one or more contact pads 206 and/or one or more ground pads 208. Unlike sensor assembly 200, the one or more contact pads 206 can be positioned along one dimension of the sensor assembly 200*a* and the one or more ground pads 208 can be positioned along another dimension of the sensor assembly 200*a*. For example, the reference electrode 222 can be positioned between the sensors 202*a*, 202*b* and the one or more contact pads 206.

Figure 8C:
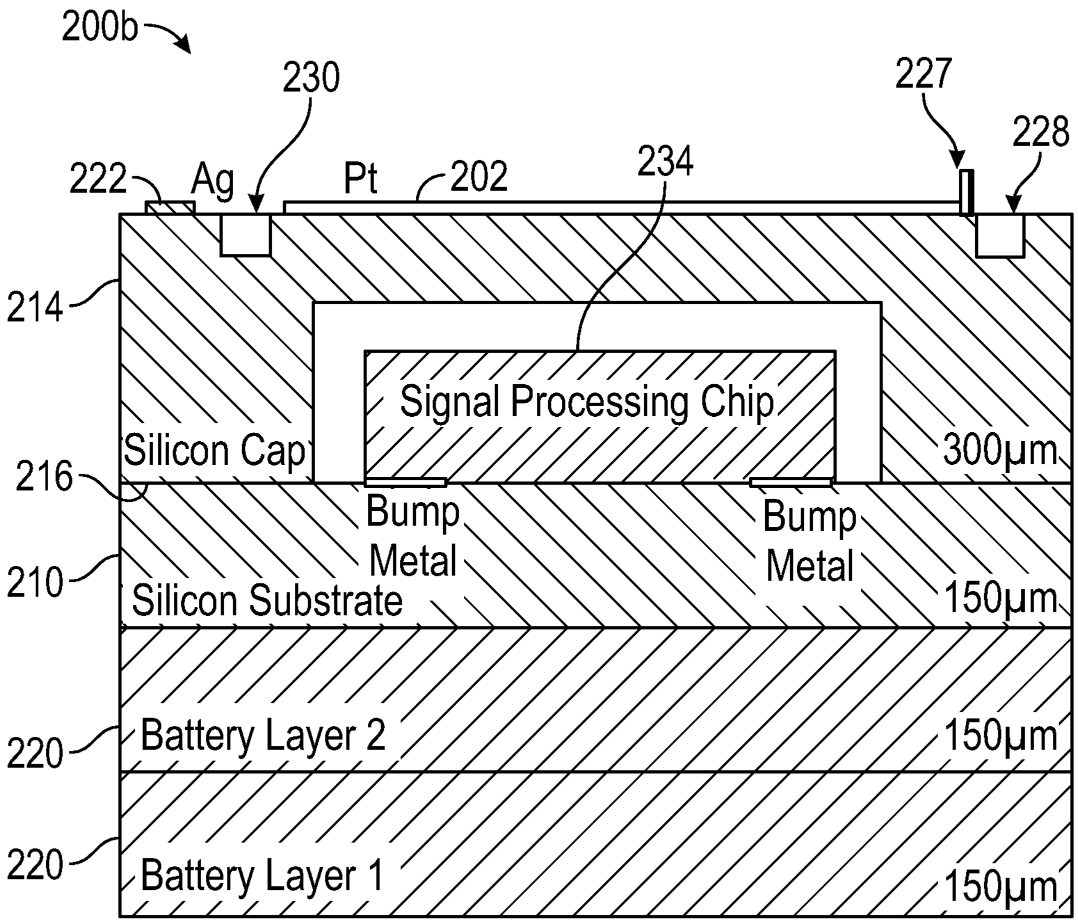
FIG. 8C illustrates an alternative configuration of the cross-section shown in FIG. 8B.

FIGS. 8B and 8C illustrate schematic cross-sectional views of the sensor assembly 200*a*. As shown in FIG. 8B, the sensor assembly 200*b* can include a configuration platform 221 stacked on at least one power source 220. The configuration platform 221 can include a stacked configuration connected by metal fusing. For example, the configuration platform 221 can include a substrate layer 210, a second substrate layer 214, and a signal processing chip 234 and/or a capacitor 232 therebetween. The substrate layer 210 can carry the one or more contact pads 206. The second substrate layer 214 can carry the sensor 202 and/or the reference electrode 222. The second substrate layer 214 can include at least one channel 228, 230, for example an etched channel. For example, the second substrate layer 214 can include at least one channel 228, 230 on either side of the sensor 202. At least one channel 228 may be disposed between the sensor 202 and the reference electrode 222. The channels 228, 230 can receive or engage a polymer membrane to form a seal about the sensor 202.

The sensor assembly 200*b* shown in FIG. 8C can include all of the features of the sensor assembly 200*a* except as described below. As shown in FIG. 8C, the second substrate layer 214 forms a cap about the signal processing chip 234. The second substrate layer 214 can be bonded to the substrate layer 210 to provide a hermetic seal. For example, the second substrate layer 214 can be bonded to the substrate layer 210 using a metallized bond zone 216 for eutectic attachment. Additionally or alternatively to the one or more channels 228, 230, the sensor assembly 200*b* may include one or more raised edges 227 extending from a surface of the sensor assembly 200*b* to engage the polymer membrane and form a seal about the sensor 202.

Additionally or alternatively to the antenna(s) 112 described herein, the inside of the channel(s) 228, 230 can include one or more antenna(s) (not shown). For example, the channel(s) 228, 230 can include an Antenna in a Package ("AIP") antenna in a platform configuration for complementing external communication or receiving communication for the processing system. Positioning the antenna in the channel(s) 228, 230 increases the surface area available for the sensor 202. A length of the antenna in the channel(s) 228, 230 can be less than or equal to 10 mm or less than or equal to 7 mm. A thickness of the antenna in the channel(s) 228, 230 can be less than or equal to 5 microns or less than or equal to 3 microns.

The stacked configuration shown in FIGS. 8B and 8C increases the surface area available for an active sensing area. The stacked configuration hermetically seals certain processing components of the sensor assembly (e.g., the signal processing chip 234 and the capacitor 232) without external polymeric packaging strategies. Advantageously, the stacked configuration can reduce the volume of component in the final assembly of the sensor assembly. Although the sensor assemblies shown in FIGS. 8B and 8C are shown to be in a stacked configuration, the sensor assemblies can be in any appropriate configuration.

Figure 9A:
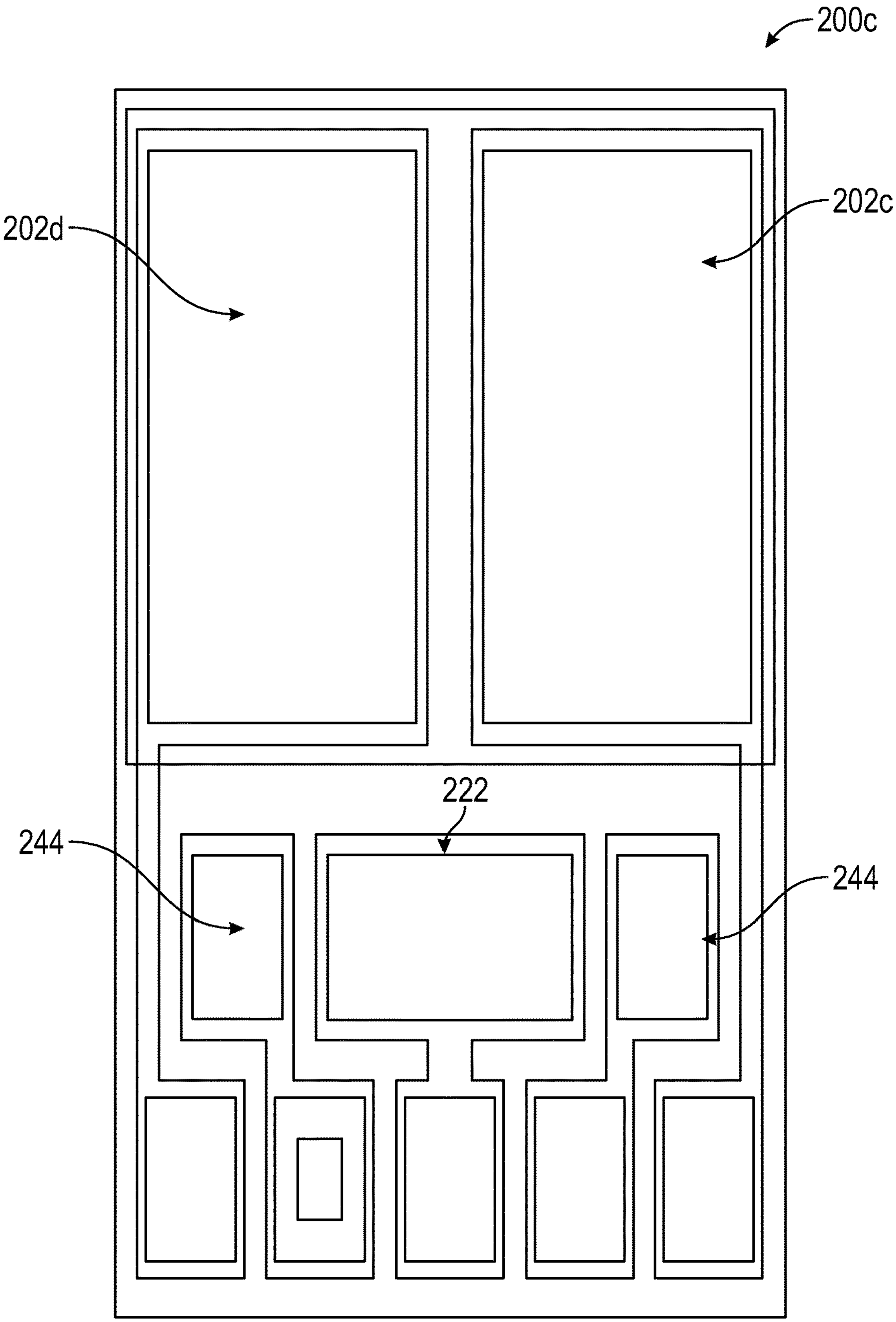
FIG. 9A illustrates a schematic view of certain components of an example sensor assembly, according to certain aspects of the present disclosure.

FIG. 9A illustrates a top-down schematic view of a sensor assembly 200*c*. The sensor assembly 200*c* can include any of the features of the sensor assemblies described above.

The sensor assembly 200*c* can include one or more sensors 202*c*, 202*d*. For example, the sensor assembly 200*c* can include a working sensor or electrode 202*c*, such as a glucose sensor, and a counter sensor or electrode 202*d*, such as an oxygen sensor. The glucose sensor can include a platinum or platinum alloy base. The glucose sensor can include a top permeable membrane to generate a chemical reaction by the chemistry reaction (e.g., oxidase base to blood fluid element extraction of glucose and oxygen). The oxygen sensor can support detection of fluid exchange and generate signal by chemical reaction. Optionally, the sensor assembly 200*c* can include a reference electrode 222 as described above. The reference electrode 222 can be a complement balancer and eliminate noise in the CPU signal. The ratio between the surface area of the working electrode 202*c* and the counter electrode 202*d* can be between be between 1:1 to 1:10. The ratio between the surface area of the working electrode 202*c* and the combination of the counter and reference electrode 202*d*, 222 can be between 1:10 and 1:15, for example 1:11 or 1:13. With larger counter electrodes, the reference electrodes 222 may be smaller, or vice versa to meet the overall ratio.

The sensor assembly 200*c* can include a connectivity switch. For example, the connectivity switch can include one or more pads 244 such as a ground contact conduit pad and a balance conduit pad. As the fluid in the fluid-rich environment increases to a threshold amount, the signal between the two pads 244 increases. As fluid decreases, signal decreases to a negligible level. The conductivity switch can identify fluid transmission from the parent artery through the aneurysm neck and into the aneurysm. The conductivity switch can be the sole identifier of fluid flow in the sensor assembly, or the conductivity switch can be used in combination with another sensor described herein. If the clinician continues to observe a signal over an extended period of time, this can be an indicator that the aneurysm is not clotting. Based on this information, the clinician may choose to deliver a drug or additional medical device to promote embolization.

Figure 9B:
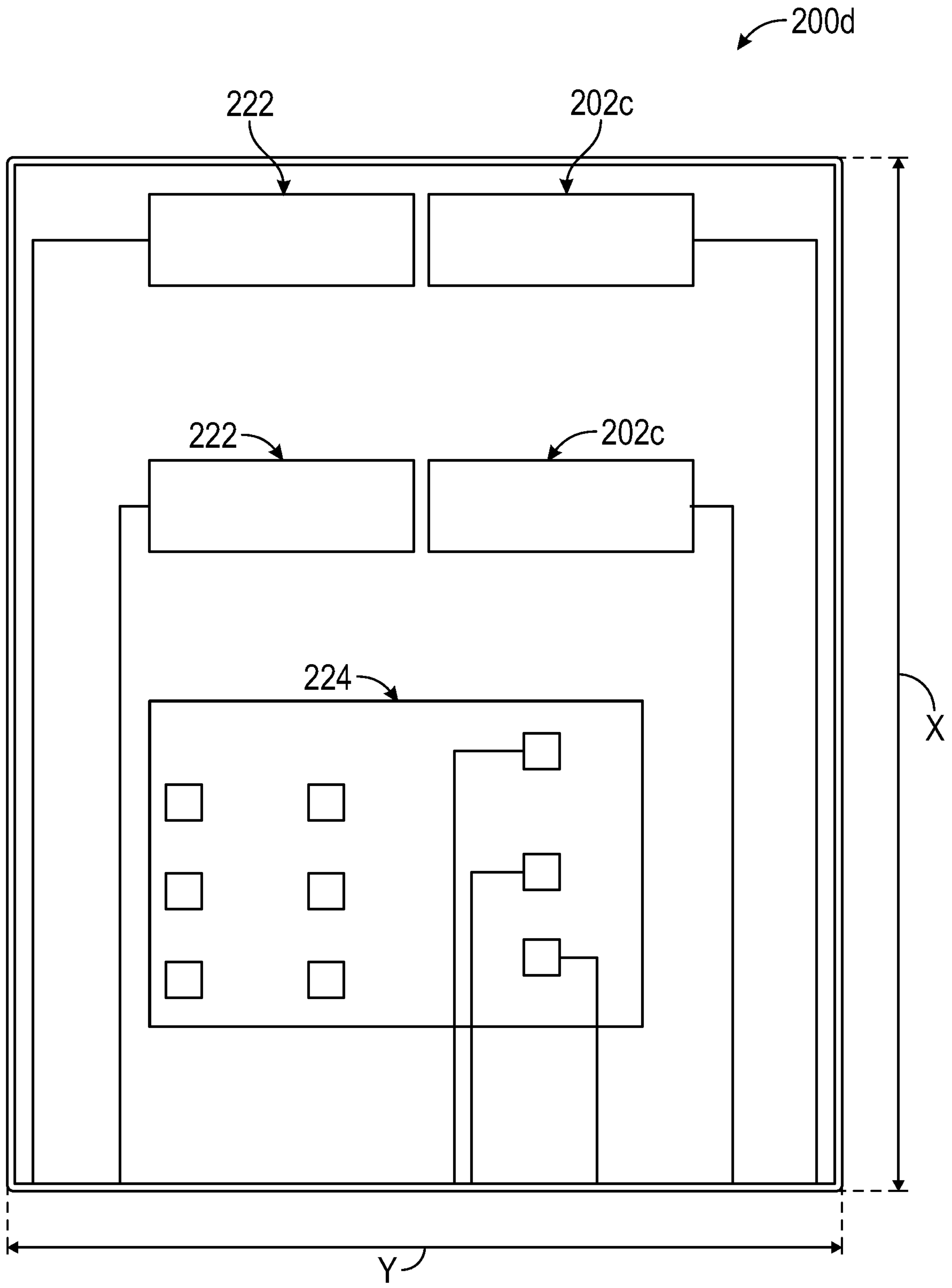
FIG. 9B illustrates a schematic view of certain components of another example sensor assembly.

In some configurations, the sensor assembly 200*c* may only perform certain functions when the conductivity switch is in contact with fluid. For example, the sensor(s) 202*c*, 202*d* can be adapted to operate only when the signal is above the threshold amount. As another example, the sensor assembly 200*c* may cause a drug to be released when the signal is above the threshold amount. Depending on the ratio between the working electrode and the reference electrode, it may be possible to eliminate the counter electrode. In these sensor configurations, the voltage levels may be sufficiently low that there may be no need for a counter electrode to eliminate noise. Removing the counter electrode enables the development of a smaller sensor assembly. For example, FIG. 9B shows a sensor assembly 200*d* having reference electrodes 222 and working electrodes 202*c*, which may be glucose sensors, but no counter electrodes. The sensor assembly 200*d* may include one or more electrical pads 244 for connectivity to other circuit components of the sensor assembly 200*d*.

Without the counter electrodes, the X or Y dimensions of the sensor assembly 200*d* may be less than or equal to about 1.5 mm or less than or equal to about 1.0 mm. The ratio of surface area of the working electrode(s) 202*c* and the reference electrode(s) 222 may be 1:1.

Figure 15A:
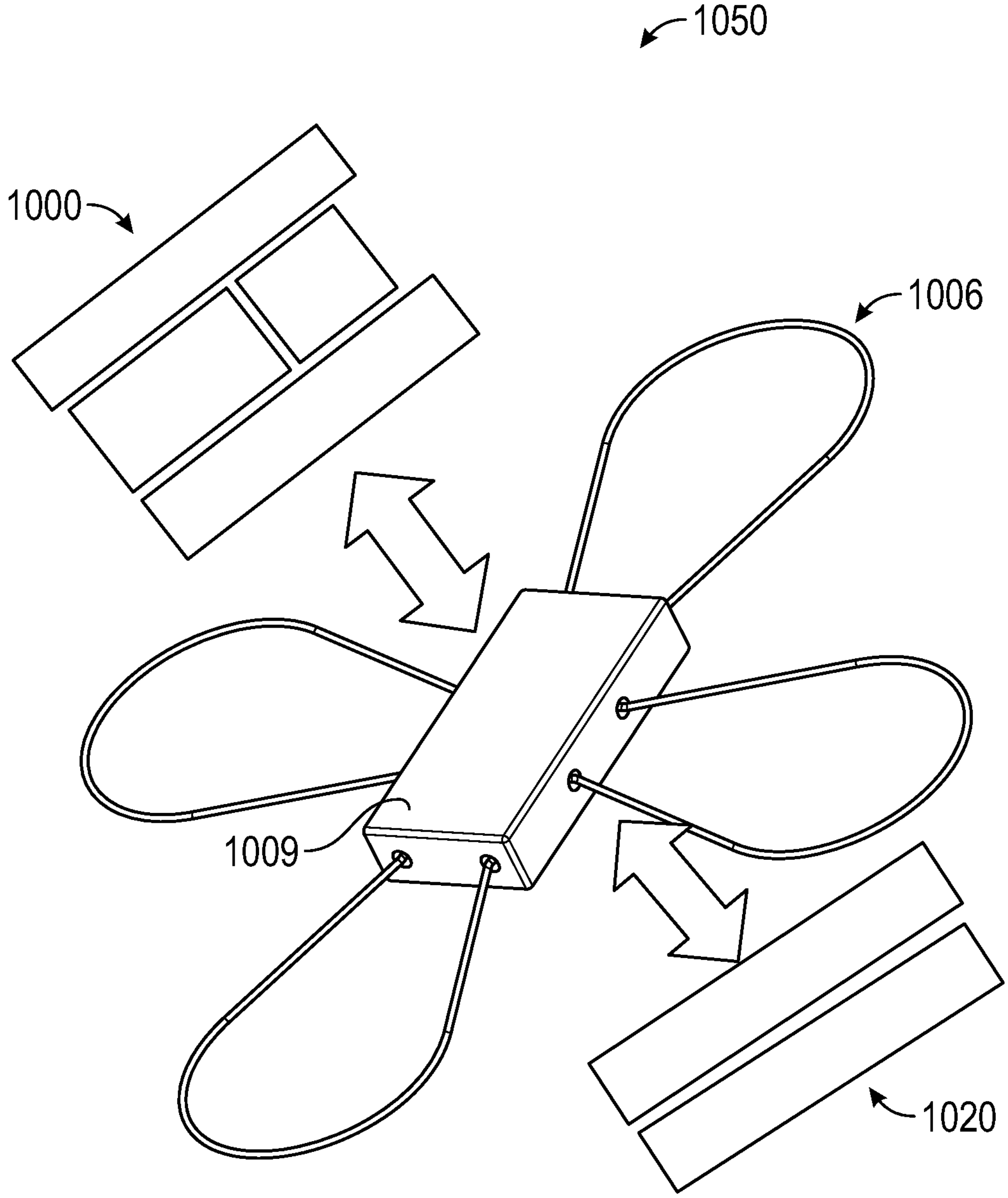
FIG. 15A illustrates a sensor system.

With reference to FIG. 15A, another illustrative embodiment of a sensor system 1050 is shown. The sensor system 1050 resembles the sensor system 150 discussed above in many respects. Accordingly, numerals used to identify features of the sensor system 150 are incremented by a factor of a thousand (1000) to identify like features of the sensor system 1050.

One or more sensor systems 1050 may be deployed in an aneurysm to measure one or more physiological parameters. In some configurations, a single sensor system 1050 may include one or more sensors to measure one or more physiological parameters. In other configurations, multiple sensor systems 1050 may be deployed within the aneurysm with each sensor system 1050 measuring a different physiological parameter.

Figure 15C:
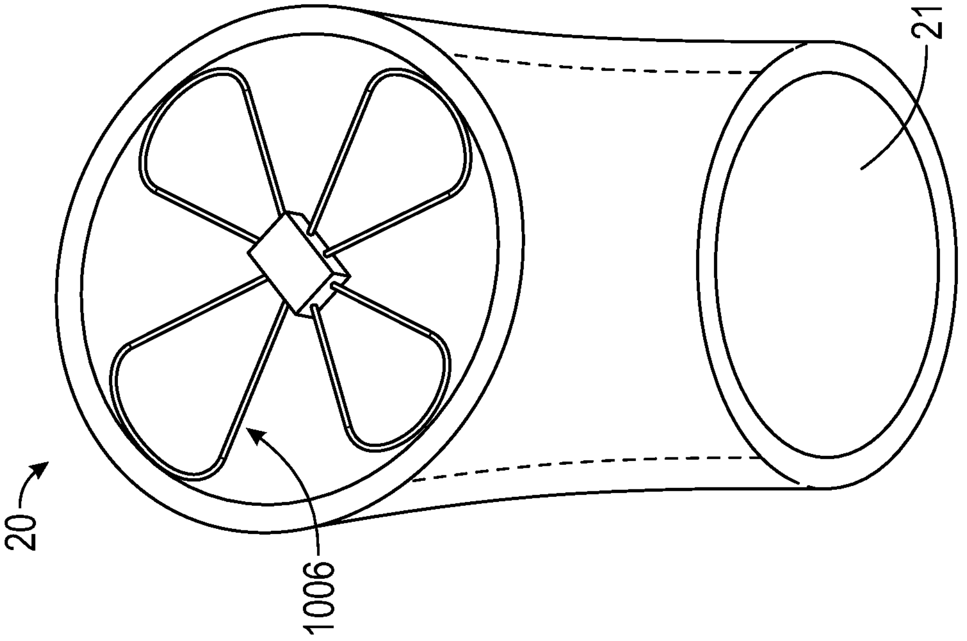
FIGS. 15B and 15C illustrate components of the sensor system in the aneurysm.

As shown in FIG. 15A, the sensor system 1050 may include a sensor assembly 1000 having one or more sensors, for example any one the sensors 102, 202 described above. The sensor assembly 1000 may include any of the features of sensor assembly 100, 200, 200*a-d* described above. The sensor assembly 1000 may collect data continuously, intermittently, and/or on demand. The sensor system 1050 may include an anchoring structure 1006 configured to stabilize a position of the sensor assembly 1000 within an interior space of the aneurysm. The sensor system 1050 may include a power source 1020, for example one or more batteries or supercapacitors. The anchoring structure 1006 may be positioned between the sensor assembly 1000 and the power source 1020, but other configurations are possible where these the anchoring structure 1006, sensor assembly 1000, and the power source 1020 are joined together, for example where the sensor assembly 1000 is positioned between the anchoring structure 1006 and the power source 1020. The sensor assembly 1000 and/or the power source 1020 may include a stacked configuration similar to the sensor assembly 200*a* shown in FIG. 8C or other layouts described herein. Unlike the above-described layouts, there may be a space between the sensor assembly 1000 and the power source 1020 for the anchoring structure 1006 as shown in FIG. 15E. The combination of the sensor assembly 1000 and its power source 1020 may have a height of less than or equal to about 1 mm or less than or equal to about 0.75 mm.

The sensor system 1050 may include communications circuitry to wirelessly communicating with a remote electronic device. The communications circuitry may include one or more antennas 1012, which may have any of the features of antenna 112. The antenna may include an implantable material with the ability to function with radio frequency performance. The antenna 1012 may transmit sensor data collected by the one or more sensors 1002 to another location within the body or a location outside the body. The sensor data may be raw sensor data, data partially processed (e.g., signal filtering or conditioning) or fully processed into a parameter by a processor in the sensor assembly 1000. The one or more antennas 1012 may be separate components from or fixed to the sensor assembly 1000 or anchoring structure 1006. When the sensor system 1050 is a single component, the entire sensor system 1050 can be deployed with a single delivery system.

Figure 15B:
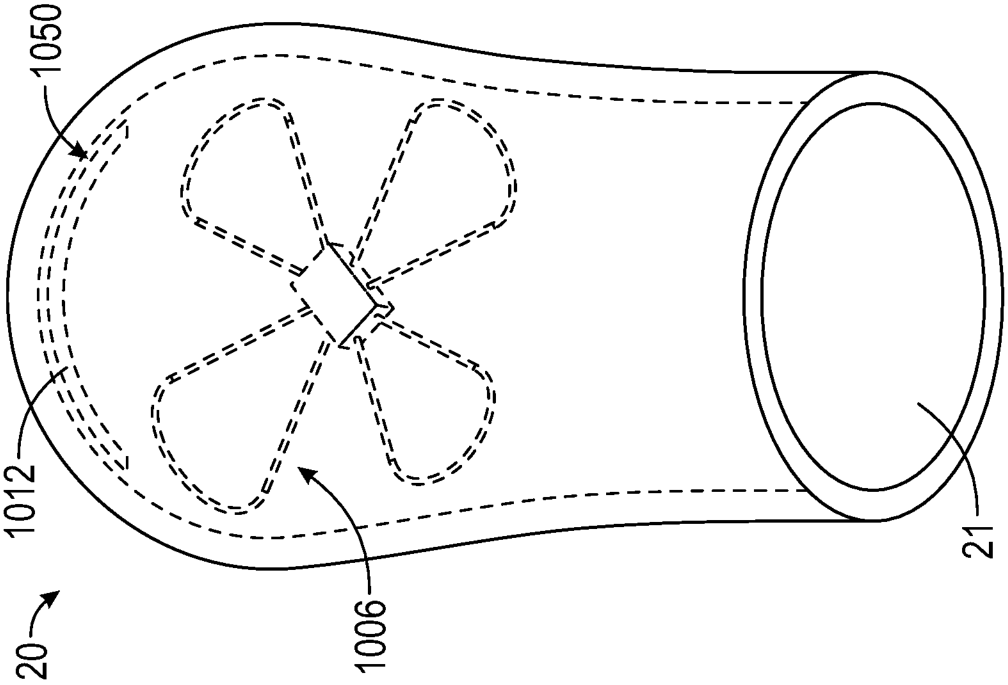

As shown in FIG. 15B, an antenna 1012 may be positioned against a top or innermost wall of the aneurysm 20. The antenna 1012 may be positioned between the sensor assembly 1000 and the top or innermost wall of the aneurysm 20. Alternatively or additionally, an antenna 1012 may be positioned at a neck 21 of the aneurysm 20 to provide a secondary function as an occluder or to maintain the sensor assembly 1000 within the aneurysm. Optionally, one or more treatment devices, such as coils, may be positioned in the space between the antenna 1012 and the sensor assembly 1000 or between the sensor assembly 1000 and the aneurysm wall (see for example FIG. 3C). Although schematically illustrated as a separate component, the antenna 1012 may be fixed to the sensor assembly 1000 and/or the anchor structure 1006.

The anchoring structure 1006 may be joined to the sensor assembly 1000. The anchoring structure 1006 may be chemically and/or mechanically joined to the sensor assembly 1000. For example, the anchoring structure 1006 may include a body portion 1009 to join the anchoring structure 1006 to the sensor assembly 1000. The body portion 1009 may be fused or mechanically clipped to the sensor assembly 1000. In one example, the body portion 1009 may be a sacrificial wafer including the same material as a substrate in the sensor assembly 1000 for fusing the anchoring structure 1006 to the sensor assembly 1000.

The anchoring structure 1006 may be a resilient structure capable of collapsing or bending to a configuration that may be loaded into a delivery catheter. Upon release, the anchoring structure 1006 may transition to an expanded configuration. When deployed, the anchoring structure 1006 may provide opposing forces within the aneurysm 20 and stabilize the sensor system 1050 at least until treatment device(s) can be deployed in the aneurysm 20. As shown in FIGS. 15B and 15C, the anchoring structure 1006 maintains a position of the sensor assembly 1000 (not shown) within an interior space and away from the aneurysm walls so as to not interfere with the placement of treatment device(s). The anchoring structure 1006 may be atraumatic to avoid puncturing or tearing a wall of the aneurysm 20. The anchoring structure 1006 may stabilize a position of the one or more sensors 1002 within the aneurysm 20 without fixing the sensor system 1050 in the aneurysm wall.

Figure 15D:
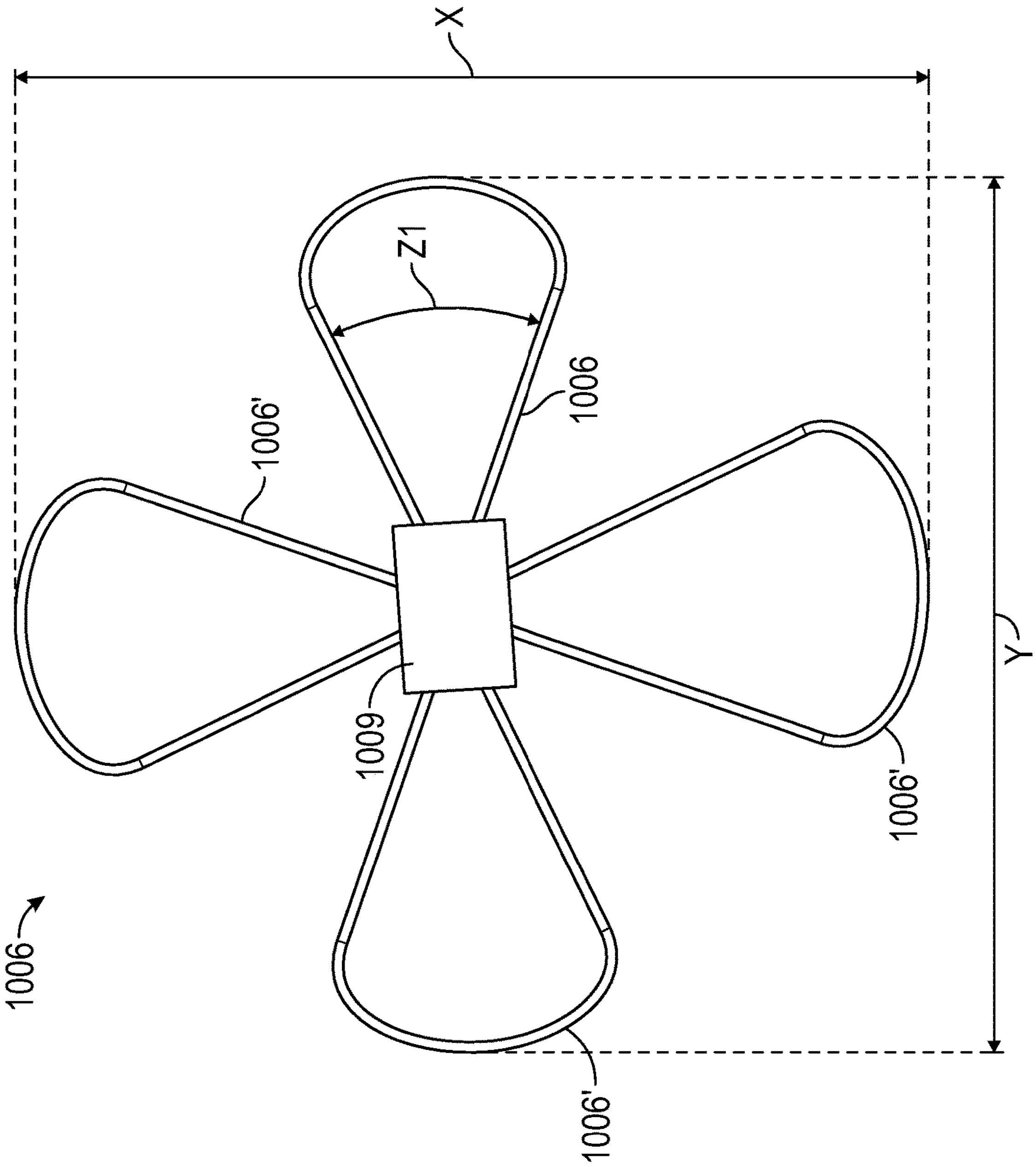
FIG. 15D illustrates an anchoring structure of the sensor system shown in FIG. 15A.
Figure 15E:
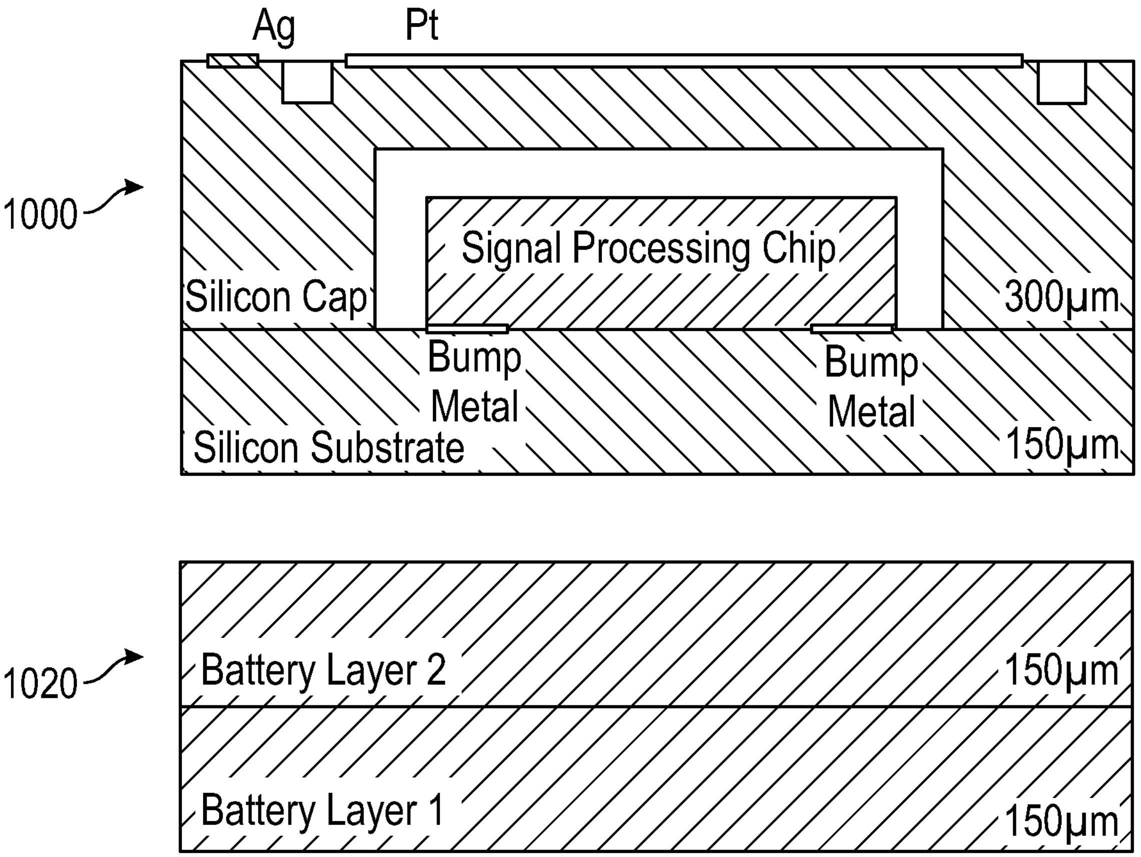
FIG. 15E illustrates a schematic representation of a portion of the sensor system shown in FIG. 15A.

As shown in FIG. 15D, the anchoring structure 1006 may include one or more anchor portions 1006'. There may be at least two anchor portions 1006' and/or less than or equal to ten anchor portions 1006', for example three, four, five, or six anchor portions 1006'. The one or more anchor portions 1006' may be circumferentially spaced apart such that the one or more anchor portions 1006' contact the aneurysm wall at one or more positions around the aneurysm 20.

The anchor portions 1006' can be arms extending from a remainder of the sensor system 1050. As illustrated, the anchor portions 1006' can take on a wire loop shape defining an open space within each anchor portion 1006', but in other configurations, the anchor portions 1006' may be coils, prongs, extensions, or other anchor shapes. The anchor portions 1006' may be integrally formed with or joined to the body portion 1009. The loop configurations allows one or more treatment devices to extend through the open spaces of the anchor portions 1006'. Each anchor portion 1006' may have a rounded edge to provide atraumatic contact with the aneurysm wall. Each anchor portion 1006' may have substantially the same shape, but may be different in size. As shown in FIG. 15D, two anchor portions 1006' along the X-axis are larger than the two anchor portions 1006' along the Y-axis. The anchor portions 1006' may be shape set to the desired configuration. For example, the anchor portions 1006' may include nitinol, platinum, iridium, or any material that can be shape set to the desired configuration.

As illustrated, the body portion 1009 may be centrally positioned within the anchoring structure 1006. But in other embodiments, the body portion 1009 may be off-center relative to the overall anchoring structure 1006. The anchor structure 1006 may extend across a single plane, for example the plane containing the X and Y axes illustrated in FIG. 15D. In other configurations, at least one anchor portion 1006' may be positioned in a different plane than one or more other anchor portions 1006'. For example different anchor portions 1006' may be in different but parallel planes. As another example, at least anchor portion 1006' may extend in a direction perpendicular to one or more other anchor portions 1006', e.g., out of the page as drawn in FIG. 15D.

The anchoring structure 1006 may be symmetrical about the x-axis and/or the y-axis drawn in FIG. 15D. For example, the anchor portions 1006' may be equally spaced apart around a circumference of the sensor assembly 1000. A length of the anchoring structure 1006 along the X-axis may be the same as a length of the anchoring structure 1006 along the Y-axis, but depending on the dimensions of the body portion 1009, the lengths of the individual anchor portions 1006' may be the same or different. The length of the sensor assembly 1000 along the X-axis and/or the Y-axis may be at least about 4 mm and/or less than or equal to about 10 mm, for example about 8 mm. Depending on the dimensions of the aneurysm, the length of the anchoring structure 1006 along the Y-axis may be different from the length along the X-axis.

Each anchor portion 1006' may have a smaller width at a location near the body portion 1009 compared to a location spaced further from the body portion 1009. Each anchor portion 1006' may span an angle greater than 0 degree angle and/or less than or equal to about 90 degrees, for example between about 15 degrees and 75 degrees or between 30 degrees and 60 degrees, for example about 45 degrees. When the anchor portions 1006' are in the same plane, the angle between a central axis of a first anchor portion 1006' and a circumferentially adjacent second anchor portion 1006' can be less than or equal to about 90 degrees and/or greater than or equal to about 45 degrees, for example between about 45 degrees and about 60 degrees, between about 60 degrees and about 75 degrees, or between about 75 degrees and about 90 degrees. If the anchor portions 1006' are in different planes, the angle between a central axis of a first anchor portion 1006' and a circumferentially adjacent second anchor portion 1006' may be less than or equal to about 60 degrees or 45 degrees and/or greater than or equal to about 0 degrees, for example between about 0 degrees and about 15 degrees, between about 15 degrees and about 30 degrees, and between about 30 degrees and about 45 degrees.

For loading into the delivery catheter, individual anchor portions 1006' may bend or fold inward to form a more elongate shape. The anchor portions 1006' may also bend toward each other into a more elongate configuration for loading into the delivery catheter. For example, the two anchor portions 1006' along the X-axis may bend or fold toward the anchor portions 1006' along the Y-axis to create a more elongate profile, or circumferentially adjacent anchor portions 1006' may bend or fold closer together to create the more elongate profile.

Figure 15F:
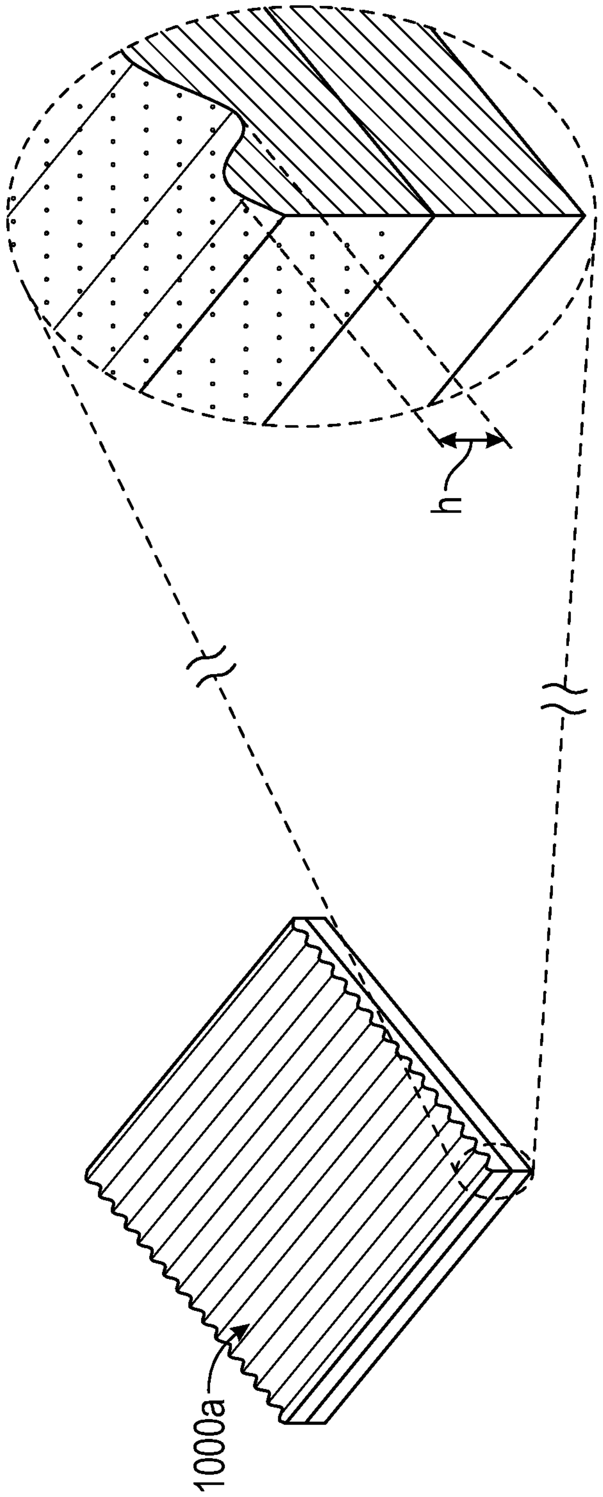
FIG. 15F illustrates a surface profile of the sensor assembly.

FIG. 15F illustrates the profile of an outer surface 1000*a* of the sensor assembly 1000. The outer surface 1000*a* can be shaped or modified to inhibit cell endothelialization. Endothelialization impedes or blocks interaction of the sensor assembly 1000 and the surrounding fluid. The surface profile shown in FIG. 15F lengthens the functional life of the sensor assembly 1000.

As illustrated, the outer surface 1000*a* can include a series of peaks and valleys. The peaks and valleys inhibit cell endothelialization. The wave height h may be greater than or equal to about 20 μm and/or less than or equal to about 500 μm, for example less than or equal to about 100 μm, or less than or equal to about 40 μm. The peak to peak distance may be greater than or equal to about 20 μm and/or less than or equal to about 500 μm, for example less than or equal to about 100 μm, or less than or equal to about 40 μm.

During the chip manufacturing process, the initially deposited substrate may have a profile having peaks and valleys. The peaks and valleys in the substrate may be created by etching, roughening, or otherwise modifying a surface of the substrate. Each layer deposited on top of substrate level and eventually the outer layer 1000*a* of the sensor assembly will have a similar a surface profile with peaks and valleys.

In other embodiments, the sensor assembly 1000 may be drug-coated to inhibit cell endothelialization. Although described with respect to sensor assembly 1000, this surface profile may be provided on any of the above-described sensor assemblies 100, 200, 200*a*-200*d*.

III. Methods of Use of the Sensor System

Any of the implantable sensor assemblies 100 and/or the implantable sensor systems 150 described herein can be implanted into a patient to monitor any anatomical structure of the patient. For example, the sensor assemblies 100 and/or the implantable sensor systems 150 can be implanted into an aneurysm for monitoring blood flow into the aneurysm. Less blood flow can indicate that the aneurysm is clotting, while more blood flow can indicate that the aneurysm is not clotting. Although the description below is described with respect to the sensor assembly 100 and sensor system 150, the methods may be applied to any of the sensor assemblies described herein, including sensor assemblies 200, 200*a-d*, 1000, and sensor system 1050.

Figure 11:
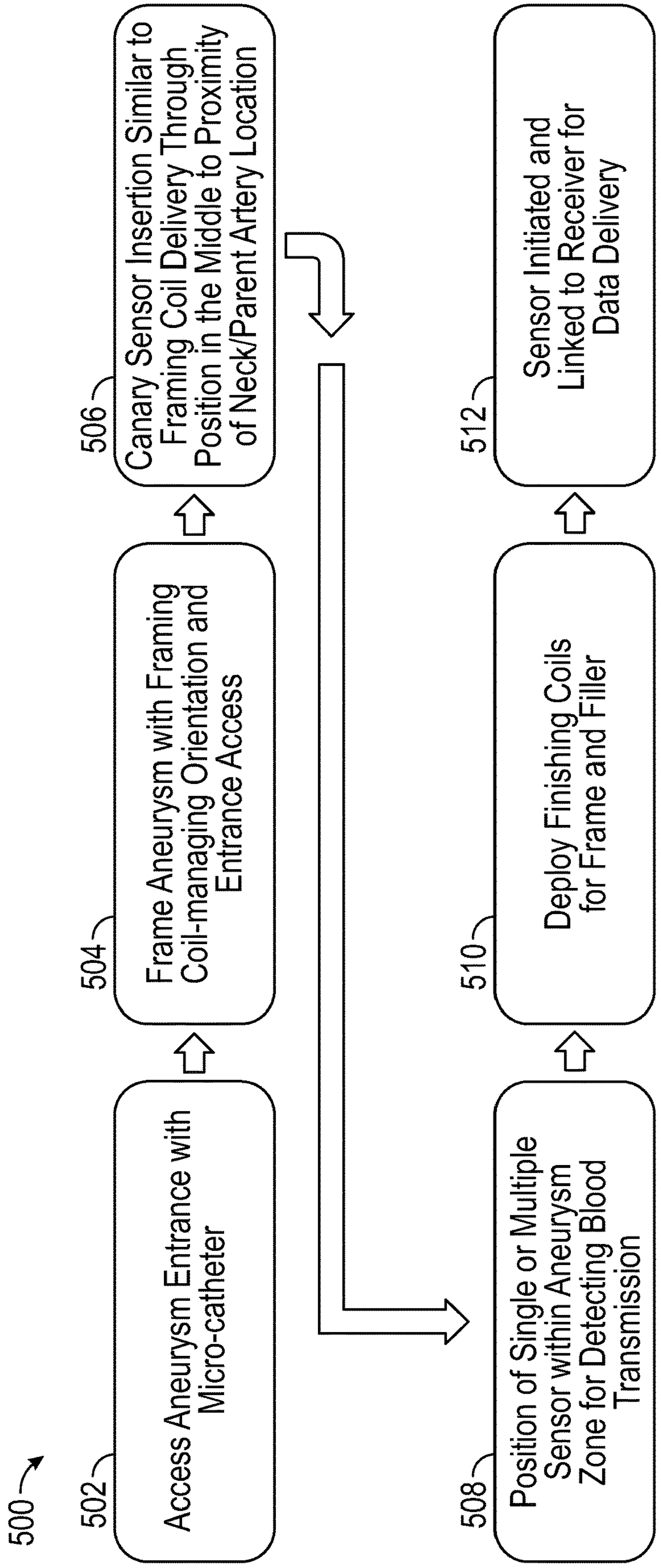
FIGS. 11 and 12 illustrate flowcharts of example methods of implanting an example sensor system into a patient, according to certain aspects of the present disclosure.

The implantable sensor assembly 100 and/or the implantable sensor system 150 can be implanted into the patient via a delivery system. FIG. 11 illustrates an example method 500 of delivering the sensor assembly 100 and/or the sensor system 150 into the anatomical structure of interest (e.g., an aneurysm). Although the method 500 is described with respect to an aneurysm, the method may be used to deliver the sensor assembly 100 to other vascular structures. Using imaging techniques, the clinician can identify the anatomical structure of interest in the patient's body. At block 502, the clinician can advance a guide structure, such as a guidewire or guide catheter, to the target site. Optionally, at block 504, the clinician can frame the aneurysm with one or more framing coils for managing the orientation and aneurysm access. At block 506, the clinician can position a distal end of the delivery system through the aneurysm neck. For example, the clinician can position the distal end of the delivery system through approximately the middle of the neck. At block 508, the clinician can position a sensor assembly 100 within the aneurysm, for example at or near the middle of the aneurysm or away from the aneurysm walls and neck, such that the sensor assembly 100 can detect blood flow into the aneurysm. At block 510, the clinician can deploy an anchoring structure 106 (e.g., a metal coil or basket) around the sensor assembly 100 or between the sensor assembly 100 and a wall of the vascular structure. At block 512, once the sensor system 150 is implanted in the aneurysm, the clinician can initiate the sensor system 150 and link it to a receiver to receive sensor data from the sensor system 150.

Figure 12:
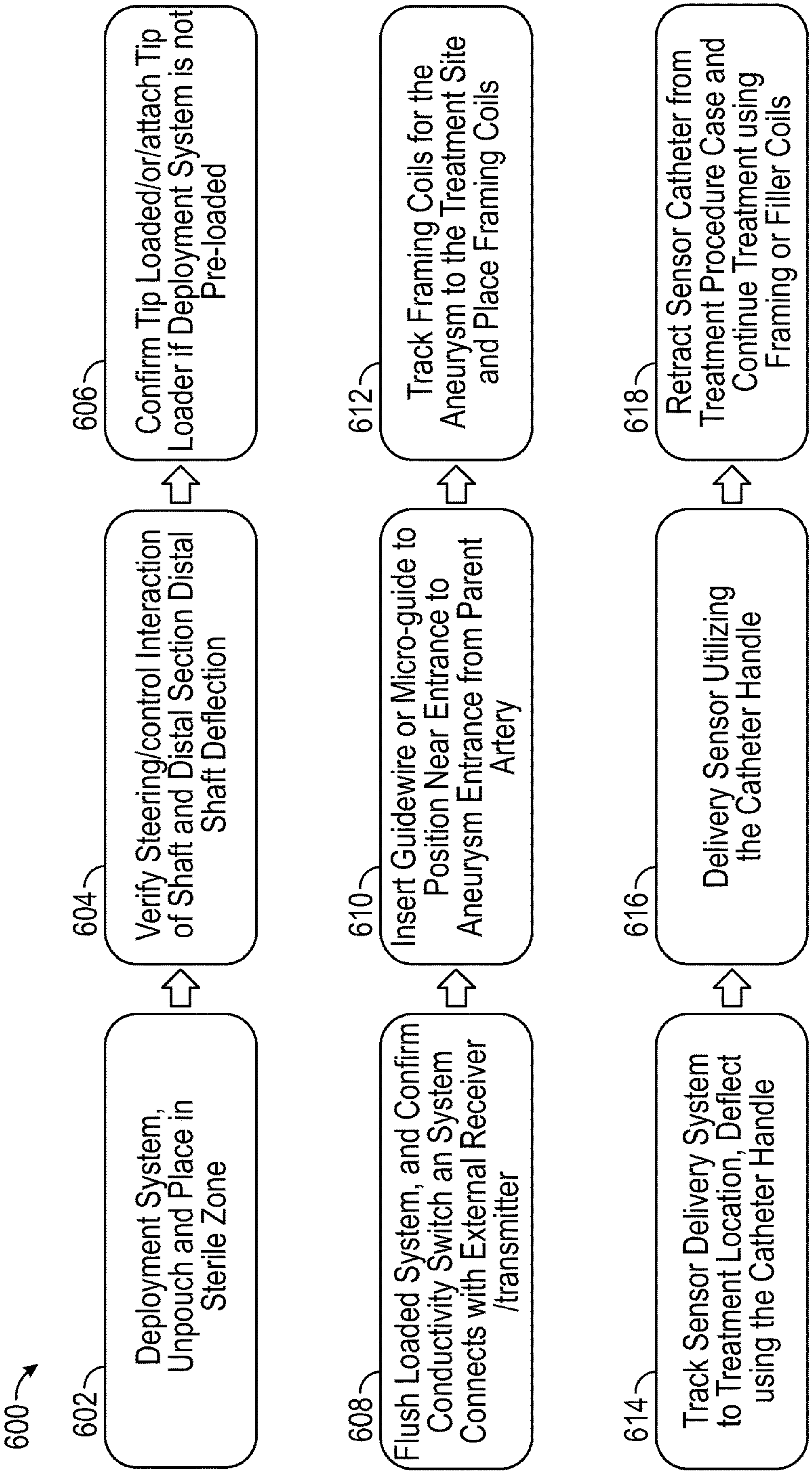

FIG. 12 illustrates another example method 600 for delivering the sensor assembly 100 and/or sensor system 150 to a patient's anatomical structure of interest, for example an aneurysm. Although the method 600 is described with respect to an aneurysm, the method may be used to deliver the sensor assembly 100 to other vascular structures. At block 602, the delivery or deployment system can be unpacked and placed in a sterile location. At block 604, the clinician can verify the steering and control of the shaft of the delivery system, and the deflection of the distal section of the shaft. At block 606, the clinician can confirm the distal tip of the delivery system is loaded with the sensor assembly 100. If the delivery system is not pre-loaded with the sensor assembly 100, the clinician can load the distal tip with the sensor assembly 100. At block 608, the medical practitioner can flush the loaded delivery system and confirm that the conductivity switch of the sensor assembly 100, if present, is functioning and that the sensor assembly 100 is capable of connecting with an external transceiver. At block 610, the medical practitioner can insert a guidewire or guide catheter to a position near the entrance or neck of the aneurysm. Optionally, at block 612, the clinician can deliver one or more framing coils to the aneurysm. At block 614, the clinician can deliver the delivery system to the aneurysm by using the catheter handle to deflect the distal section of the shaft as needed. At block 616, the medical practitioner can deliver the sensor assembly 100 into the aneurysm. Once the sensor assembly 100 is implanted in the aneurysm, at block 618, the clinician can retract the catheter from the patient and implant an anchoring structure 106, such as framing or filler coils, around the sensor assembly 100 or between the sensor assembly 100 and a wall of the vascular structure. Once the sensor system 150 is implanted in the aneurysm, the clinician can initiate the sensor assembly 150 and link it to a receiver to receive sensor data from the sensor system 150.

Once the sensor system 150 is implanted into the patient and initially configured, the sensor system 150 can begin generating continuously or intermittently sensor data related to one or more physiological parameters of the patient. For example, when a conductivity sensor switch of the sensor system 150 is exposed to the patient's blood, the sensor system 150 can switch on begin detecting one or more physiological parameters of the patient. The sensor system 150 can transmit the sensor data to a receiver continuously, intermittently at a regular or irregular time interval, or upon command. The receiver can be, for example, a base station, a smart device, a computing device or an external transceiver 402.

IV. Kit

Any of the implantable sensor assemblies and/or anchor structures described herein may be provided in a kit with one or more delivery systems. The same delivery system may be used to deliver the sensor assembly and the anchor structure. Alternatively, the kit may include separate delivery systems for the sensor assembly and the anchor structure.

The delivery system may be pre-loaded with the sensor assembly prior to packaging or provided in the kit separate from the sensor assembly. When separately provided, the delivery system may be loaded with the sensor assembly by the clinician.

The delivery system may include a loading chamber for carrying the sensor assembly. For example, the loading chamber may be provided in a lumen of the delivery system. The lumen may carry a release mechanism, such as a pusher, to release the sensor system from the delivery system. The loading chamber may be positioned in the same lumen or a different lumen as the guidewire. The loading chamber may be separate and distinct from the guidewire lumen and/or fluid delivery lumen.

The delivery system may include a deflectable distal tip. The deflectable tip may include a radiopaque marker to track a location of the delivery system within the vasculature with standard fluoroscopy techniques. The deflectable distal tip may be actively and/or passively deflected to steer the sensor assembly to the target site. In delivery systems with active deflection, the delivery system may include a handle capable of mechanically and/or electrically steering the deflectable distal tip. For example, the handle may directly cause deflection of the deflectable distal tip through one or more cables, wires, or other connection between the handle and the deflectable distal tip. As another example, the handle may indirectly cause deflection of the deflectable distal tip by deflecting an outer sleeve, which forces deflection of the deflectable distal tip.

The delivery system may be provided with an adaptor for connection to a robotic surgical system. The clinician may use the robotic surgical system to actively steer the delivery system to the target site. Robotic surgical systems, teleoperated surgical systems, and the like, which may be used or adapted to connect with a delivery system of the present disclosure so as to deliver and implant an implantable sensing assembly of the present disclosure into a patient, have been commercialized by several companies. One example of such a teleoperated, computer-assisted surgical system (e.g., a robotic system that provides telepresence) with which embodiments of the present disclosure may be used, are the da Vinci Surgical Systems manufactured by Intuitive Surgical, Inc. of Sunnyvale, Calif, USA. See, e.g., U.S. Pat. Nos. 9,358,074; 9,295,524; and 8,852,208; U.S. Patent Publication Nos. 20140128886; 20200253678; 20190192132; 20190254763; 20180318020; 20170312047; 20170172671; 20170172674; 20170000575; 20170172670; 20130204271; and 20120209305; and PCT Publication No. WO2020150165, each of which is incorporated by reference. Another example is Medtronic, Inc. (Minneapolis, MN, USA; and related companies, e.g., Covidien LP, Mansfield MA USA and Medtronic Navigation, Inc., Louisville CO USA) including their Digital Surgery Division and Surgical Robotics Division, which has commercialized various robotic-assisted surgery (RAS) solutions. See, e.g., U.S. Patent Publication Nos. 20200222127; 20190365477; 20190214126; 20190069964; and 20130289439, each of which is incorporated by reference. Yet another example is Auris Health (Redwood City, CA USA; Auris Health, Inc., is part of Johnson & Johnson Medical Devices Companies. Auris Health, Inc. was formerly known as Auris Surgical Robotics, Inc.) which has commercialized their Monarch platform. See, e.g., U.S. Patent Publication Nos. 20200198147; 20200100845; 20200100853; 20200100855; 20200093554; 20200060516; 20200046434; 20200000537; 20190365209; and 20190365486, each of which is incorporated by reference. In addition, Stryker Corp. (Kalamazoo MI USA) discloses robotic surgical systems in, e.g., U.S. Patent Publication Nos. 20160374770 and 20140276949, both of which are incorporated by reference. See also, e.g., U.S. Patent Publication Nos. 20200046978; 20200001053; 20200197111; 20190262084; 20190231447; and 20190090957 and PCT Publication Nos. WO2019195841 and WO2019082224, where each of the identified publications is incorporated by reference. In one embodiment, the handle of the delivery system of the present disclosure is configured to dock with an arm of a robotic surgical system. In one embodiment, the delivery system of the present disclosure integrates with a robotic surgical system to provide robot-assisted delivery and implantation of the implantable sensing assembly of the present disclosure into a patient. In one embodiment, the present disclosure provides a method for advancing any of the implantable sensor assemblies and/or systems described herein through the vasculature of a patient, using robotic assistance.

V. Delivery System

Figure 13:
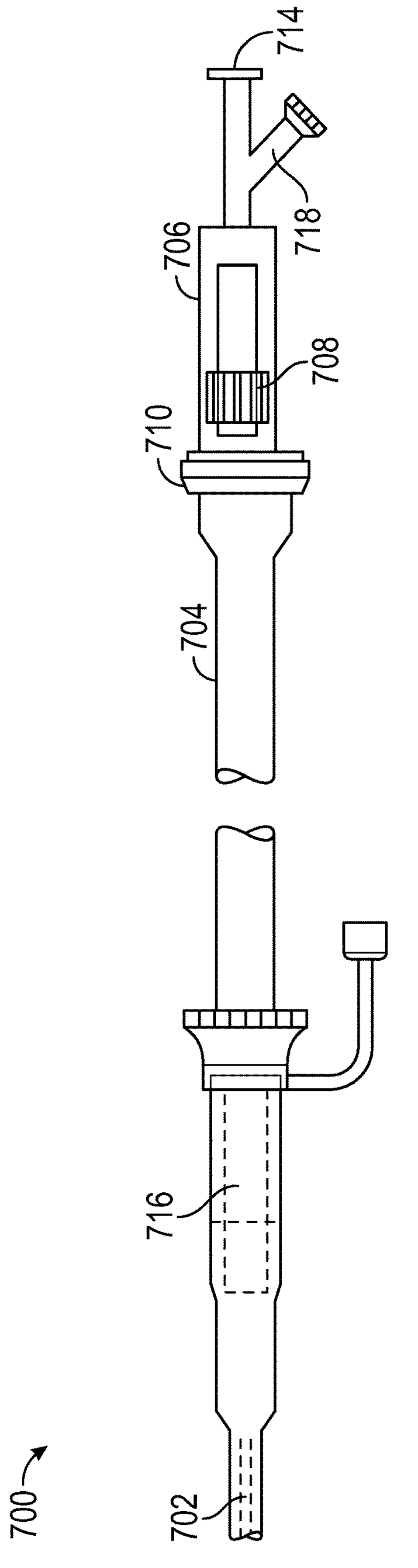
FIG. 13 illustrates a delivery system according to certain aspects of the present disclosure.

FIG. 13 illustrates a delivery system 700 for advancing any of the implantable sensor assemblies and/or systems described herein through the vasculature. The delivery system 700 may include a deflectable distal tip 702, a handle 706, and a shaft 704 therebetween. In some contexts, the delivery system 700 may be sufficiently sized to be advanced to the neuro-vasculature. For example, an outer diameter of the shaft 704 may be less than or equal to 1 mm. As used herein, the relative terms "proximal" and "distal" shall be defined from the perspective of the delivery system. Thus, proximal refers to the direction of the control end of the delivery system and distal refers to the direction of the distal tip.

The deflectable distal tip 702 may carry the sensor assembly. For example, the deflectable distal tip 702 may be pre-loaded with the sensor assembly prior to introducing the sensor assembly into the patient. The sensor assembly may be pre-loaded in a loading chamber separate from a guidewire lumen or fluid delivery lumen. The sensor assembly may be attached to the loading chamber or freely sit within the loading chamber. The sensor assembly may be sterilized prior to loading or sterilized together with the delivery system 700. In other delivery methods, the sensor assembly may be advanced to the deflectable distal tip 702 after the delivery system 700 has been advanced to the target site.

The deflectable tip 702 may be actively deflected using the handle 706 to facilitate accurate placement of the sensor assembly. For example, the deflectable tip 702 may be mechanically deflected using a user-actuatable mechanism in the handle 706. The user-actuatable mechanism may control one or more cables or wires extending through the wall of the shaft 704 or along an inner and/or outer surface of the shaft 704 to manipulate the deflectable distal tip 702. Additionally or alternatively, the deflectable distal tip 702 may be sufficiently flexible to be passively deflected. The deflectable distal tip 702 may include one or more markers to monitor a position and/or direction of the deflectable distal tip.

The deflectable distal tip 702 may be constructed of one or more polymeric materials, such as Pebax® polyethylene, polyethylene terephthalate, or other polymeric materials. The deflectable distal tip 702 may or may not be supported by a braided material.

The shaft 704 may include one or more internal lumens. For example, the shaft 704 may have a guidewire lumen for tracking the delivery system 700 to the target site. The guidewire lumen may extend from the guidewire lumen port 714 in the handle 706 and through the deflectable distal tip 702. The shaft 704 may have a fluid delivery lumen to delivery fluid to the delivery site.

The shaft 704 may be constructed of one or more polymeric materials, such as Pebax® polyethylene, tetrafluoroetheylene, polytetrafluoroethylene, or other polymeric materials. The shaft 704 may be reinforced with a braided material to enhance pushability and/or torque management. The shaft 704 may be co-extruded with a first polymeric material and a liner and/or outer layer. The liner and/or outer layer may include tetrafluoroetheylene or polytetrafluoroethylene.

The handle 706 may include one or more user-actuatable mechanisms for controlling different functions of the delivery system 700. For example, the handle 706 may include a first user-actuatable mechanism 710 capable of releasing the sensor assembly from the delivery system 700. The handle 706 may include a second user-actuatable mechanism 708 capable of steering the shaft 704 and/or the deflectable distal tip 702. As used herein, the terms "first" and "second" user-actuatable mechanism can be used interchangeably. For example, the "first" user-actuatable mechanism may refer to any control feature described herein.

The first user-actuatable mechanism 710 may push the sensor assembly out of the distal tip 702 of the delivery system 700. For example, the first user-actuatable mechanism 710 may control a pusher extending through a lumen in the shaft 704. In another configuration, the first user-actuatable mechanism 710 may withdraw the distal tip 702 relative to the sensor assembly to release the sensor assembly. As illustrated, the first user-actuatable mechanism 710 may be an axial slider, but in other configurations, the first user-actuatable mechanism 710 may be a button, switch, lever, rotatable knob, rotatable dial, or otherwise.

The second user-actuatable mechanism 708 may steer the shaft 704 and/or the deflectable distal tip 702. As illustrated, the second user-actuatable mechanism 708 may be a rotary knob capable of controlling a direction of the flexible shaft 704 and/or the distal tip 702. The rotary knob may rotate about a longitudinal axis of the handle 706. In other configurations, the second user-actuatable mechanism 710 may rotate in a different direction.

As shown in FIG. 13, the first user-actuatable mechanism 710 may be positioned proximally of the second user-actuatable mechanism 708. In other configurations, the second user-actuatable mechanism 708 may be positioned proximally or elsewhere relative to the first user-actuatable mechanism 710.

The handle 706 may also include one or more ports. For example, the handle 706 may include a flush port 712 for introducing fluid into the delivery system 700. The handle 706 may include a separate guidewire lumen port 714. As illustrated, the one or more ports are positioned proximally of the user-actuatable mechanisms, but may be positioned anywhere along the delivery system 702.

The handle 706 may be molded from a polymeric material. For example, the polymeric material may include ABS, polypropylene, Pebax®, or other materials.

Optionally, the delivery system 700 may include a delivery sheath 716 positioned over the shaft 704. The delivery sheath 716 may act as an introducer. The delivery sheath 716 may include one or more seals to prevent fluid flow out of the patient from a space between the delivery sheath 716 and the shaft 704. For example, the delivery sheath 716 may include a seal near a proximal end of the delivery sheath 716. The delivery sheath 716 may include a separate port 718 to flush the delivery sheath 716 or lubricate the interaction between the delivery sheath 716 and the shaft 704.

In some configurations, the delivery sheath 716 may enhance steerability and trackability of the delivery system 700 through the vasculature. For example, the delivery sheath 716 may be connected to the deflectable distal tip 702 to enable steering of the deflectable distal tip 702. As another example, the delivery sheath 716 may not engage the deflectable distal tip 702, but bending of the delivery sheath 716 forces deflection of the distal tip 702.

The delivery sheath 716 may be constructed of a same or different material as the deflectable distal tip 702. For example, the delivery sheath 716 may be constructed of a polymeric material, such as Pebax® polyethylene, polyethylene terephthalate, or other polymeric materials. The delivery sheath 716 may or may not be supported by a braided material.

Figure 14:
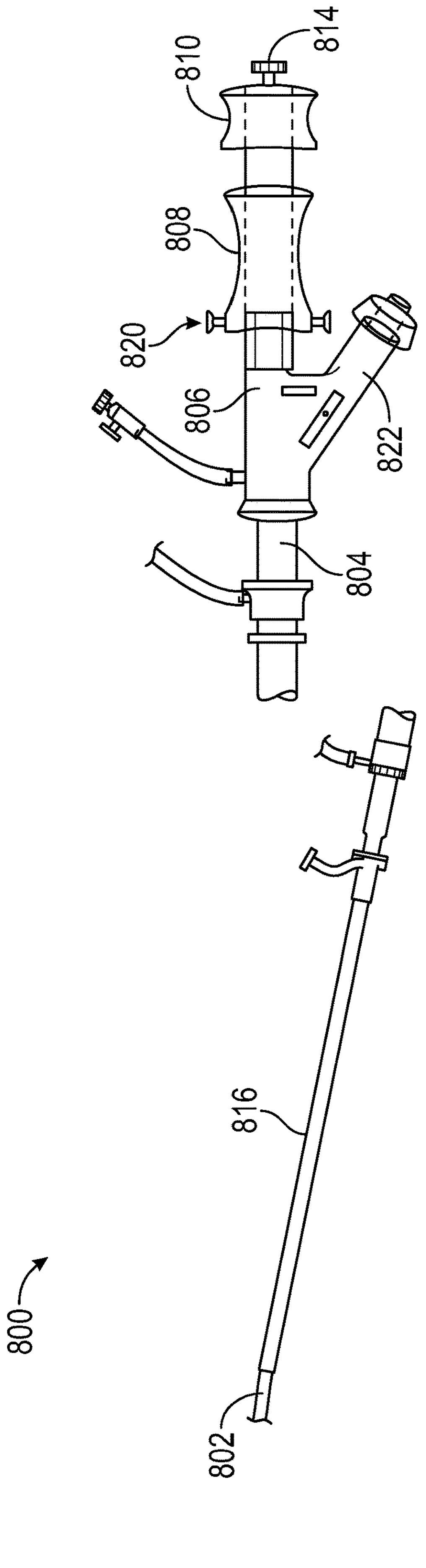
FIG. 14 illustrates another delivery system according to certain aspects of the present disclosure.

FIG. 14 illustrates another delivery system 800 for advancing any of the implantable sensor assemblies or systems described herein through the vasculature. The delivery system 800 may include any of the features described above with respect to the delivery system 700. The delivery system 800 may include a deflectable distal tip 802, a handle 806, and a shaft 804 therebetween.

The deflectable distal tip 802 may include a loading chamber for carrying the sensor assembly. The loading chamber may be separate from any guidewire, fluid delivery lumen, and/or other lumen extending through the deflectable distal tip 802.

The deflectable distal tip 802 may include a molded or thermally reshaped polymer. For example, the deflectable distal tip 802 may include one or more polymeric materials, such as Pebax® polyethylene, tetrafluoroetheylene, polytetrafluoroethylene, or other polymeric materials. The deflectable distal tip 802 may or may not be supported by a braided material. For example, the deflectable distal tip 802 may include a braided structure lined with and/or coated or over-molded with a separate polymeric layer such as tetrafluoroetheylene or polytetrafluoroethylene.

The shaft 804 may include one or more internal lumens. For example, the shaft 804 may have a guidewire lumen for tracking the delivery system 800 to the target site. The guidewire lumen may extend from the guidewire lumen port 814 in the handle 806 and through the deflectable distal tip 802. The shaft 804 may have a fluid delivery lumen to delivery fluid to the delivery site. The shaft 804 may include one or more polymeric materials, such as Pebax® polyethylene, tetrafluoroetheylene, polytetrafluoroethylene, or other polymeric materials.

The handle 806 may include one or more user-actuatable mechanisms for controlling different functions of the delivery system 800. For example, the handle 806 may include a first user-actuatable mechanism 810 capable of releasing the sensor assembly from the delivery system 800. The handle 806 may include a second user-actuatable mechanism 808 capable of steering the shaft 804 and/or the deflectable distal tip 802. The second user-actuatable mechanism 808 may be rotatable knob, but in other configurations, the second user-actuatable mechanism 808 may be a button, switch, lever, slider, rotatable dial, or otherwise. The handle 806 may include a third user actuatable mechanism 820 to stabilize the shaft 804 and/or the orientation of the deflectable distal tip 802. For example, the third user actuatable mechanism 820 may be a toggle lock. As used herein, the terms "first," "second" and "third" user-actuatable mechanism can be used interchangeably. For example, the "first" user-actuatable mechanism may refer to any control feature described herein. The user-actuatable mechanisms may be positioned in an order corresponding to their usage during a procedure.

The handle 806 may include a control 822 for steering the deflectable tip 802 and/or the shaft 804. For example, the handle 806 may include a mechanical and/or electrical control mechanism for steering the deflectable distal tip 802 and/or the shaft 804. For example, the delivery system 800 can include a slider or carriage assembly with one or more wires or cables. The delivery system 800 can include a voltage control to activate the deflection mechanism. The wires or cables can electrically transmit the energy to steer the deflectable distal tip 802 and/or shaft 804. Additionally or alternatively, this mechanical and/or electrical control mechanism may be applied to a delivery sheath positioned over the shaft 804.

Figure 16A:
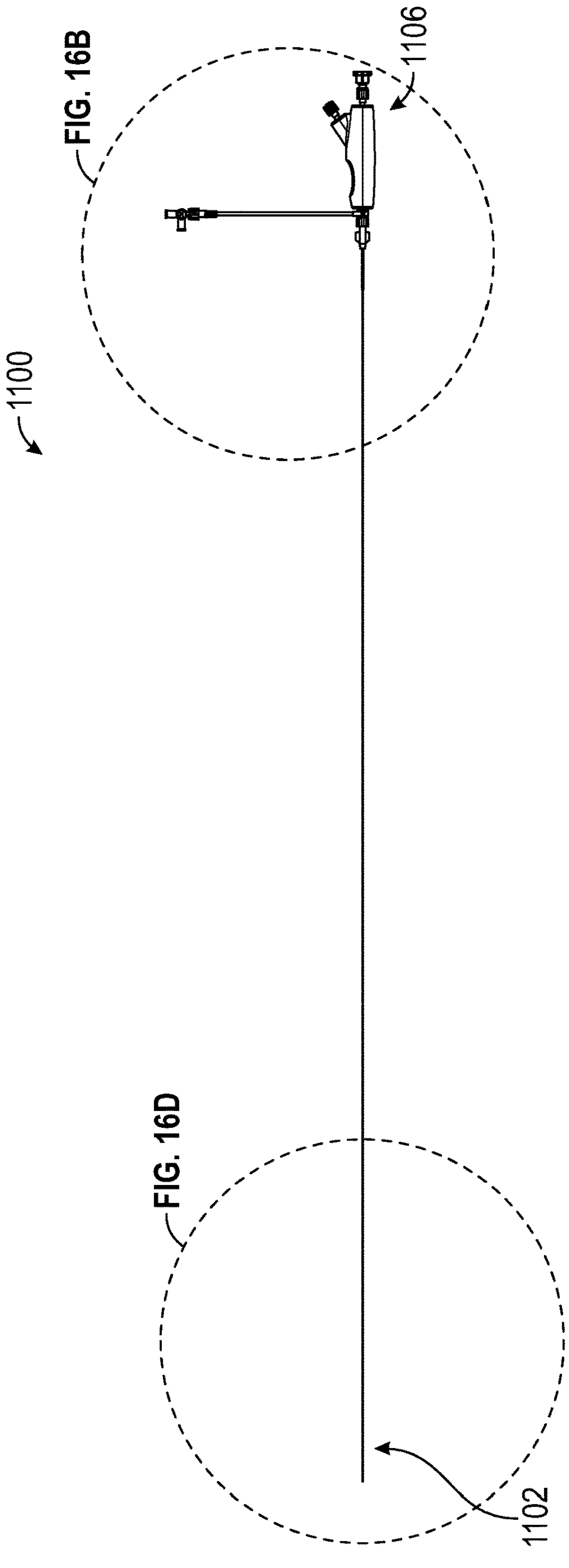
FIG. 16A illustrates another delivery system for deploying a sensor system.

FIG. 16A illustrates another delivery system 1100 that can include any of the features of delivery systems 700, 800. Accordingly, numerals used to identify features of the delivery systems 700, 800 are incremented by a factors of a hundred (100) to identify like features of the delivery system 1100. The delivery system 1100 is described below with respect to the sensor system 1050, but may be used in combination with any of the sensor systems or sensor assemblies described herein.

Figure 16B:
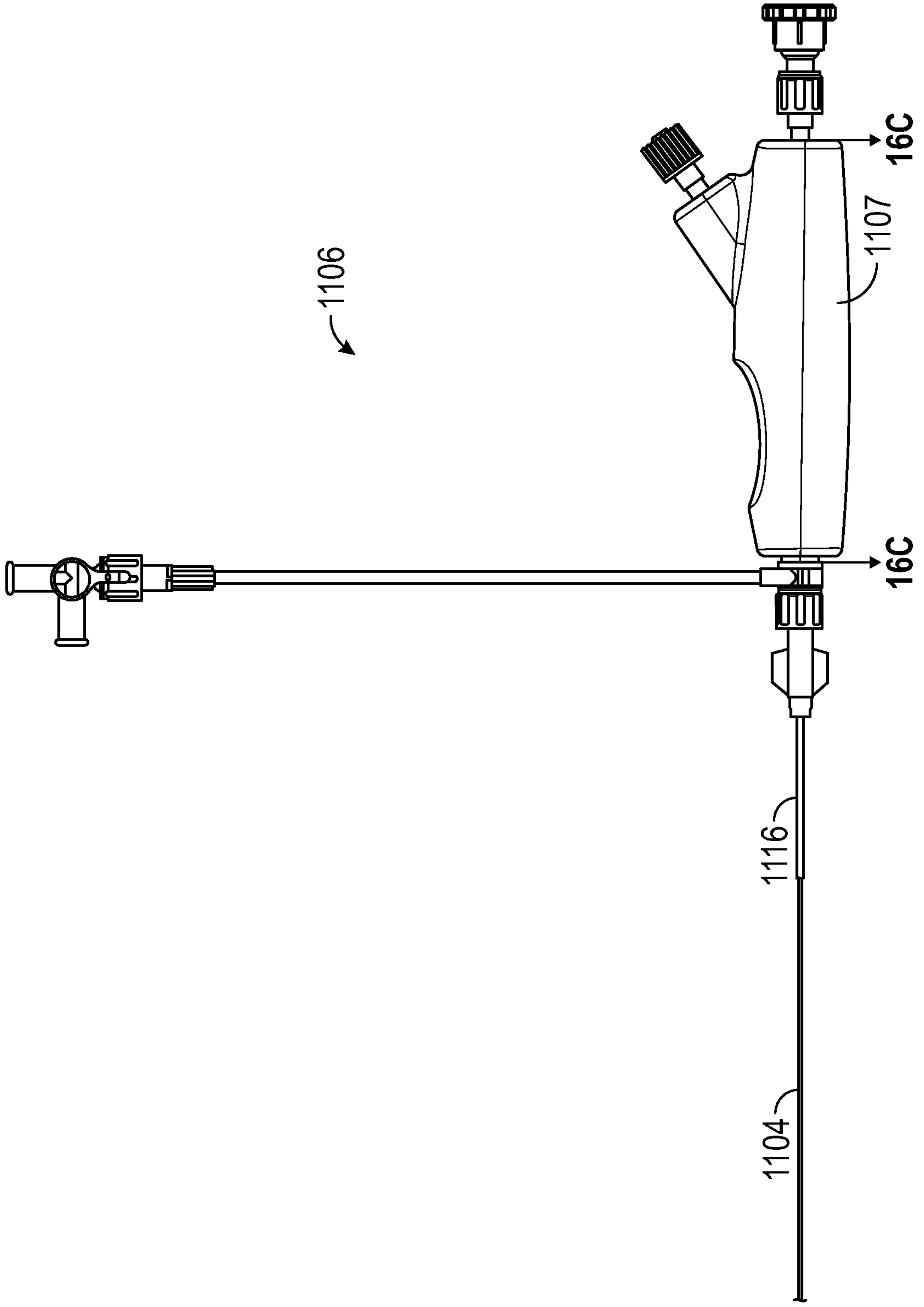
FIG. 16B illustrates a proximal portion of the delivery system shown in FIG. 16A.
Figure 16C:
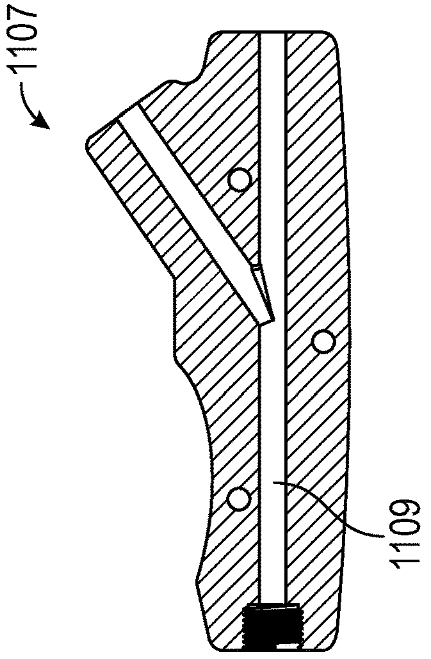
FIG. 16C illustrates a body portion of the handle shown in FIG. 16B.
Figure 16D:
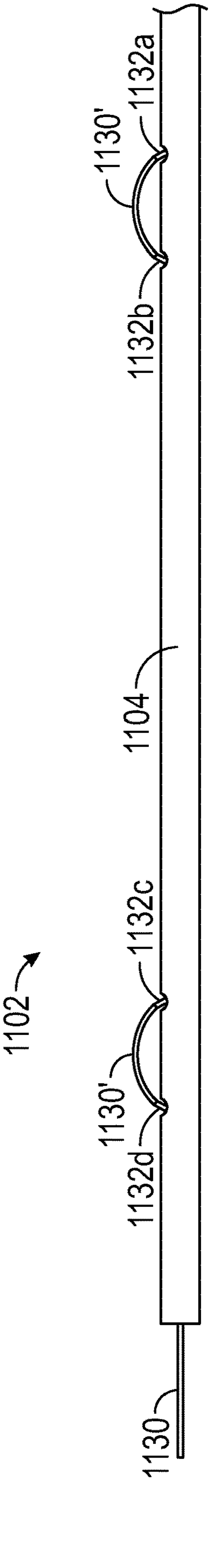
FIG. 16D illustrates a distal portion of the delivery system shown in FIG. 16A.

The delivery system 1100 may include a proximal portion 1106 (shown in FIG. 16B) and a distal portion 1102 (shown in FIG. 16D). As shown in FIG. 16B, the proximal portion 1106 includes a handle body 1107. A delivery sheath 1116 extends distally from the handle body 1107. A shaft 1104 extends through a lumen of the delivery sheath 1116. FIG. 16C illustrates a cross-section of the handle body 1107. The handle body 1107 includes a lumen 1109 through which a retention wire 1130 may extend.

As shown in FIG. 16D, the retention wire 1130 may extend through the shaft 1104. The retention wire 1130 may extend out of openings 1132*a, c* in a sidewall of the shaft 1104 and extend back through different openings 1132*b, d* in the sidewall of the shaft 1104 to form one or more loop portions 1130', for example two loop portions (see FIG. 16D) or four loop portions (see FIG. 17B). The loop portions 1130' may be located within 10 cm from a distal tip of the shaft 1104, within 5 cm from a distal tip of the shaft 1104, within 2 cm from a distal tip of the shaft 1104 or within 1 cm from a distal tip of the shaft 1104. As illustrated in FIG. 16D, the retaining wire 1130 may extend out of the shaft 1104 through a first opening 1132*a* in the sidewall of the shaft 1104 and back into the shaft 1104 through an adjacent, second opening 1132*b*. The retaining wire 1130 may extend back out of the shaft 1104 through a third opening 1132*c* closer to the distal tip of the shaft 1104 and back into through the shaft 1104 through an adjacent, fourth opening 1132*d*. A distal end of the retaining wire 1130 may extend out of a distal tip of the shaft 1104. The loop portions 1130' may be axially separated, but rotationally aligned, along the shaft 1104. In other embodiments, adjacent loop portions may be rotationally offset (see FIG. 17B).

Each loop portion 1130' is configured to retain one or more anchor portions 1006' of a sensor system 1050. The loop portions 1130' retain the sensor system 1050 external of the shaft 1104. For example, the sensor system 1050 may be retained in a space between an outer wall of the shaft 1104 and an inner wall of the delivery sheath 1116. In other embodiments, the retaining wire 1130 may extend through the space between the delivery sheath 1116 and the shaft 1104 and extend into and out of the shaft 1104 to create loop portions 1130' within the shaft 1104 such that the sensor system 1050 may be retained within the shaft 1104.

Figure 16E:
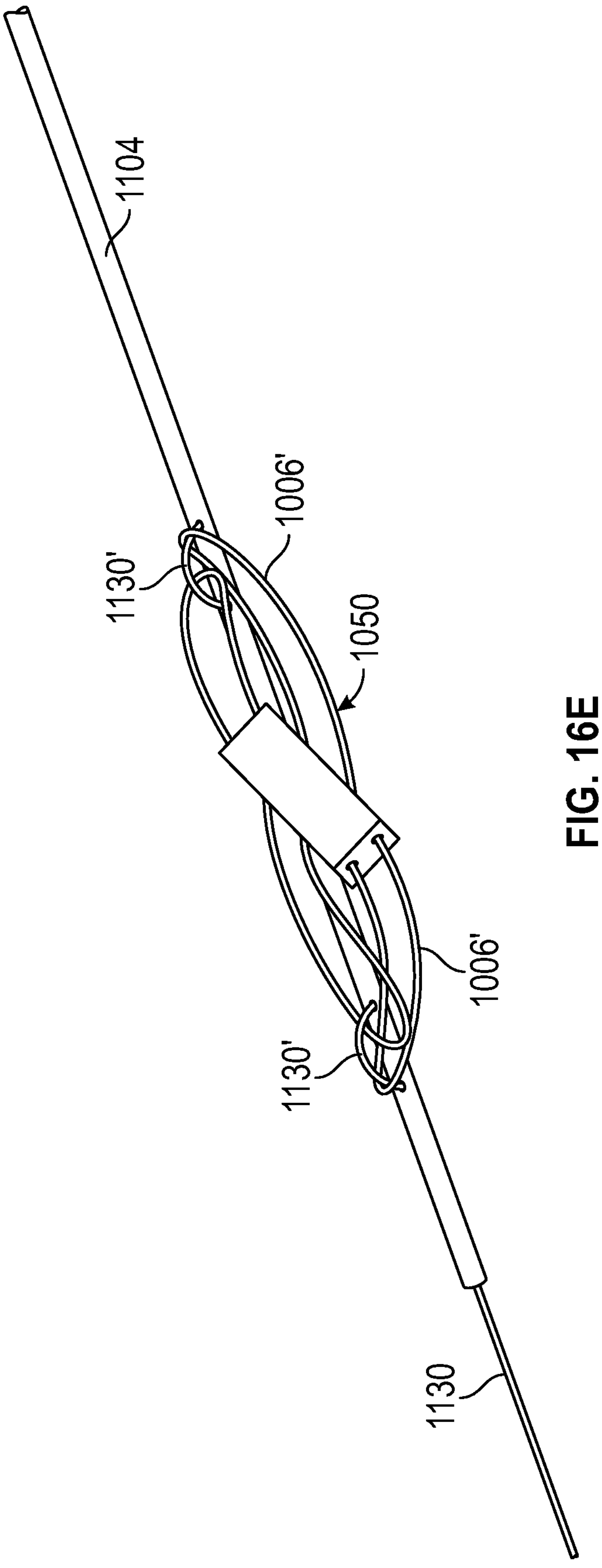
FIGS. 16E and 16F illustrate deployment of a sensor system.

As shown in FIG. 16E, each loop portion 1130' may be configured to retain two anchor portions 1006'. When the retaining wire 1130 extends out of the shaft 1104 through the first opening 1132*a*, the retaining wire 1130 may be threaded through one or more loop-shaped anchor portions 1006' before extending back into the shaft 1104 through the second adjacent opening 1132*b* to capture the anchor portion(s) 1006' within the loop portion 1130'. The retaining wire 1130 may extend back out of the shaft 1104 through the third opening 1132*c*, through one or more additional loop-shaped anchor portions 1006', and back into the shaft 1104 through the fourth adjacent opening 1132*d* to capture the additional anchor portion(s) 1006' within the loop portion 1130'. In this configuration, the anchoring structure 1006 of the sensor assembly may be retained within the delivery system 1100 and against the shaft 1104 in an elongate and compact configuration.

Figure 16F:
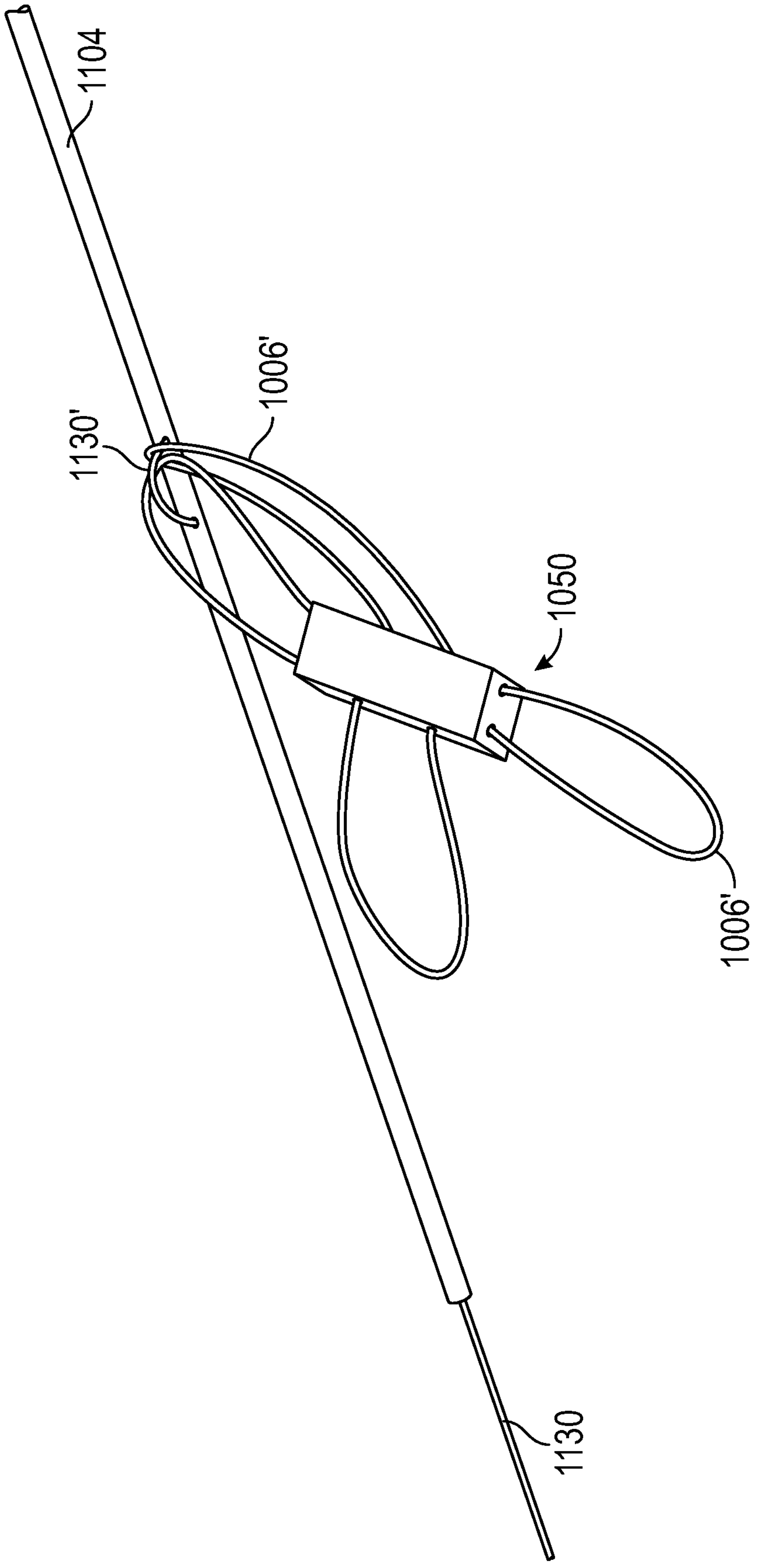

The loop portions 1130' may be sequentially released to deploy the sensor system 1050. As the retaining wire 1130 is withdrawn proximally, a distal end of the retaining wire 1130 is pulled out of the openings 1132*a-d* to release the loop portions 1130' and the corresponding anchor portion(s) 1006'. In FIG. 16F, the retaining wire 1130 has been pulled out of the third and fourth openings 1132*c, d* to release the distal-most loop portion 1130' and corresponding anchor portions 1006'. Continued withdrawal of the retaining wire 1130 releases the remaining anchor portion(s) 1006'. When released within the aneurysm, the anchor portion(s) 1006' retain the sensor system 1050 within the aneurysm as shown in FIG. 15B.

To release the sensor system 1050 within the aneurysm 20, a distal portion 1102 of the delivery system 1100 may be positioned in the parent artery and adjacent the aneurysm neck 21. The sensor assembly 1050 may be exposed to the aneurysm neck 21 by advancing the distal portion of the shaft 1104 distal of a distal end of the sheath 1116 or by proximally withdrawing the sheath 1116 to uncover the sensor assembly 1050. The openings 1132*a-d* at the distal portion of the shaft 1104 may be positioned against the aneurysm neck 21 such that, when the retaining wire 1130 is released from the openings 1132*a-d*, the sensor system 1050 is deployed within the aneurysm 20. In other methods, a distal portion of the shaft 1104 may extend into the aneurysm 20 to release the sensor system 1050 in the aneurysm 20. As mentioned in previous embodiments, the distal portion of the shaft 1104 may be steerable such that the distal end of the shaft 1104 may be guided into the aneurysm 20. Thereafter, a separate delivery system may be used to deliver the treatment device(s).

Figure 17A:
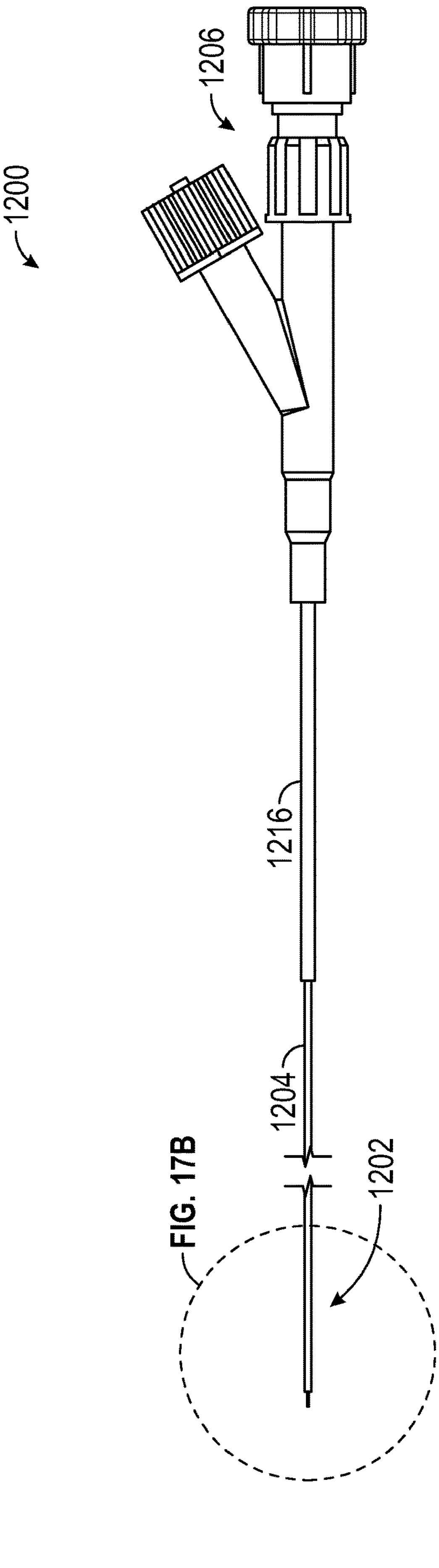
FIG. 17A illustrates another delivery system for deploying a sensor system.

FIG. 17A illustrates another delivery system 1200 that can include any of the features of delivery system 1100. The delivery system 1200 is similar to the delivery system 1100 except as described below. Features of the delivery systems 1100, 1200 are interchangeable.

Figure 17B:
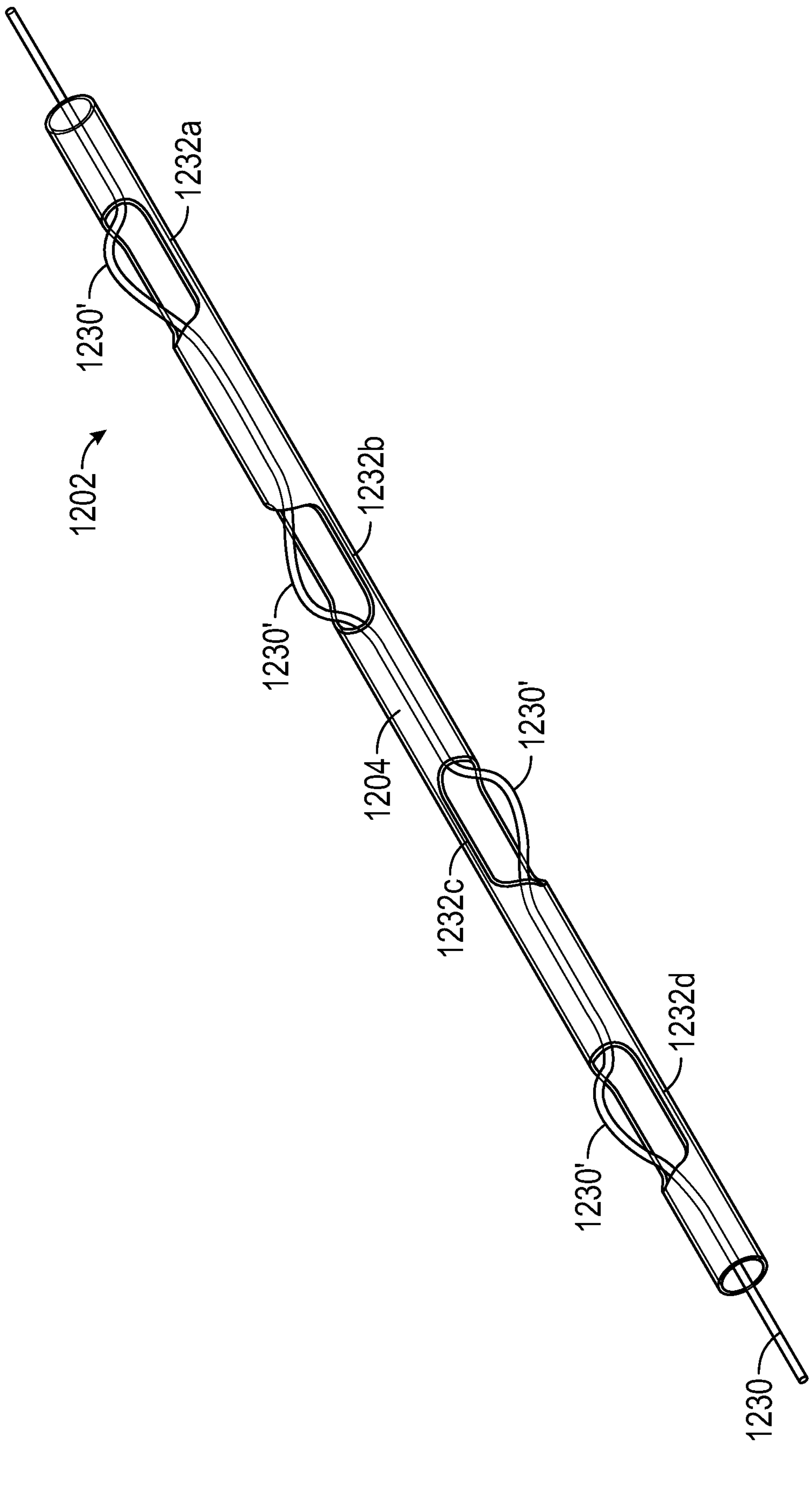
FIG. 17B illustrates an enlarged view of a distal portion of the delivery system shown in FIG. 17A.

Unlike the delivery system 1100, the delivery system 1200 includes a loop portion 1230' for each individual anchor portion 1006'. For example, for a sensor system 1050 with four anchor portions 1006', the delivery system 1200 may include four corresponding loop portions 1230'. Moreover, each loop portion 1230' may be formed by extending out of the shaft 1204 and back into the shaft 1204 through the same opening. As shown in FIG. 17B, each opening 1232*a-d* may be an elongate opening to accommodate a loop portion 1230'. The openings 1232*a-d* may be axially spaced apart. At least one of the openings 1232*c* may be rotationally offset from an adjacent opening 1232*d*, 1232*b*.

When the retaining wire 1230 extends out of the shaft 1204 through the first opening 1232*a*, the retaining wire 1230 may be threaded through a loop-shaped anchor portions 1006' before extending back into the shaft 1204 through the same first opening 1232*a* to capture the anchor portion(s) 1006' within the loop portion 1230'. The retaining wire 1230 may extend back out of the shaft 1204 through the second opening 1232*b*, through another loop-shaped anchor portion 1006', and back into the shaft 1204 through the same second opening 1232*b* to capture the additional anchor portion 1006' within the loop portion 1230'. This weaving process may be repeated for each of the anchor portions 1006'. In this configuration, the anchoring structure 1006 of the sensor assembly may be retained within the delivery system 1200 and against the shaft 1204 in an elongate and compact configuration.

Similar to the delivery system 1100, the loop portions 1230' may be sequentially released to release the sensor system 1050. As the retaining wire 1230 is withdrawn proximally, a distal end of the retaining wire 1230 is pulled out of the openings 1232*a-d* to release the loop portions 1230' and the corresponding anchor portion(s) 1006'.

VI. Additional Embodiments and Terminology

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

Although certain methods have been described herein with respect to aneurysms, the methods described herein can be applied to any vascular structure, for example a ductus arteriosus Although certain embodiments and examples have been described herein, it will be understood by those skilled in the art that many aspects of the sensor assemblies shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The methods disclosed herein may include certain actions taken by a clinician; however, the methods can also include any third-party instruction of those actions, either expressly or by implication. For example, actions such as "releasing the sensor assembly" include "instructing release of the sensor assembly."

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

VII. Example Embodiments

The following example embodiments identify some possible permutations of combinations of features disclosed herein, although other permutations of combinations of features are also possible.

1. An implantable sensor system comprising:
   a sensor capable of detecting one or more physiological parameters of a patient and generating sensor data; and
   an antenna in electrical communication with the sensor, the antenna transmits sensor data related to the one or more physiological parameters of the patient to a receiver, the antenna capable of being compressed about the sensor for loading into a delivery system and expanded upon release from the delivery system.

2. The implantable sensor system of Embodiment 1, wherein the antenna continuously transmits sensor data.

3. The implantable sensor system of Embodiment 1, wherein the antenna intermittently transmits sensor data.

4. The implantable sensor system of any one of Embodiments 1 to 3, wherein the sensor continuously detects one or more physiological parameters.

5. The implantable sensor system of any one of Embodiments 1 to 3, wherein the sensor intermittently detects one or more physiological parameters.

6. The implantable sensor system of any one of Embodiments 1 to 3, wherein the sensor is capable of being implanted in a vascular structure of the patient.

7. The implantable sensor system of Embodiment 6, wherein the vascular structure is an aneurysm.

8. The implantable sensor system of any one of Embodiments 1 to 7, wherein the antenna at least partially surrounds the sensor.

9. The implantable sensor system of Embodiment 8, wherein the antenna extends at least partially across a first surface of the sensor.

10. The implantable sensor system of Embodiment 9, wherein the antenna extends at least partially across a second surface of the sensor, the second surface opposite the first surface.

11. The implantable sensor system of any one of Embodiments 1 to 10, wherein the antenna comprises a single axis loop, a dual axis loop, or a spherical loop.

12. The implantable sensor system of any one of Embodiments 1 to 11, wherein the antenna comprises platinum metal, platinum/iridium alloy, and/or nitinol.

13. The implantable sensor system of any one of Embodiments 1 to 12, wherein the antenna is coated in a parylene film, a gold material, and/or a platinum material.

14. The implantable sensor system of any one of Embodiments 1 to 13, wherein the antenna is capable of stabilizing a position of the sensor in an aneurysm.

15. The implantable sensor system of any one of Embodiments 1 to 14, further comprising a radiopaque marker to identify a location of the implantable sensor assembly in the patient.

16. The implantable sensor system of any one of Embodiments 1 to 15, wherein the sensor generates the sensor data based on analyte materials, analyte elements, and/or byproducts caused by certain cellular interactions or exchanges or blood interactions or exchanges in blood.

17. The implantable sensor system of any one of Embodiments 1 to 16, wherein the sensor comprises a blood flow sensor, a blood pressure sensor, a metabolic sensor, a glucose sensor, an oxygen sensor, or a pressure sensor.

18. The implantable sensor system of any one of Embodiments 1 to 17, wherein the one or more physiological parameters comprises oxygen, carbon dioxide, potassium, iron, and/or glucose in the blood of the patient.

19. The implantable sensor system of any one of Embodiments 1 to 17, wherein the one or more physiological parameters comprises kinetic information.

20. The implantable sensor system of any one of Embodiments 1 to 19, wherein the antenna transmits and receives RF signals.

21. The implantable sensor system of any one of Embodiments 1 to 20, further comprising a sealing layer to hermetically seal the sensor assembly.

22. The implantable sensor system of any one of Embodiments 1 to 21, further comprising a dissolving membrane layer that dissolves when in contact with blood of the patient.

23. The implantable sensor system of Embodiment 22 wherein the dissolving membrane layer releases clot enhancers when the dissolving membrane layer dissolves.

24. The implantable sensor system of any one of Embodiments 1 to 23, further comprising a power source for providing power to the sensor.

25. The implantable sensor system of Embodiment 24, wherein the power source is rechargeable.

26. The implantable sensor system of any one of Embodiments 1 to 23, wherein the sensor is capable of being powered by a power source outside the patient.

27. The implantable sensor system of any one of Embodiments 1 to 23, wherein the sensor is an inductive sensor.

28. The implantable sensor system of any one of Embodiments 1 to 23, further comprising a supercapacitor.

29. The implantable sensor system of any one of Embodiments 1 to 28, further comprising a memory device for storing sensor data.

30. The implantable sensor system of any one of Embodiments 1 to 29, further comprising a second sensor capable of detecting a different physiological parameter than the sensor.

31. A kit comprising:

the implantable sensor system of any one of Embodiments 1 to 30; and a delivery system capable of releasing the implantable sensor assembly in a vascular structure.

32. An implantable sensor system comprising:

a sensor capable of detecting one or more physiological parameters of a patient and generating sensor data;

an antenna in electrical communication with the sensor, the antenna capable of transmitting the sensor data related to the one or more physiological parameters of the patient to a receiver;

an anchor structure for maintaining a position of the sensor in a vascular structure, the sensor disposed within an interior space defined by the anchor structure.

33. The implantable sensor system of Embodiment 32, wherein the anchor structure is separate from the sensor, and wherein the anchor structure contacts the sensor when implanted.

34. The implantable sensor system of Embodiment 32, wherein the anchor structure is directly or indirectly coupled to the sensor and/or the antenna.

35. The implantable sensor system of any one of Embodiments 32 to 34, wherein the antenna continuously transmits the sensor data.

36. The implantable sensor system of any one of Embodiments 32 to 34, wherein the antenna intermittently transmits the sensor data.

37. The implantable sensor system of any one of Embodiments 32 to 36, wherein the sensor continuously detects the one or more physiological parameters.

38. The implantable sensor system of any one of Embodiments 32 to 36, wherein the sensor intermittently detects the one or more physiological parameters.

39. The implantable sensor system of any one of Embodiments 32 to 38, wherein the sensor generates the sensor data based on analyte materials, analyte elements, and/or byproducts caused by certain cellular interactions or exchanges or blood interactions or exchanges in blood.

40. The implantable sensor system of Claim any one of Embodiments 32 to 39, wherein the sensor comprises a blood flow sensor, a blood pressure sensor, a metabolic sensor, a glucose sensor, an oxygen sensor, or a pressure sensor.

41. The implantable sensor system of any one of Embodiments 32 to 40, wherein the one or more physiological parameters comprises oxygen, carbon dioxide, potassium, iron, and/or glucose in blood of the patient.

42. The implantable sensor system of any one of Embodiments 32 to 40, wherein the one or more physiological parameters comprises kinetic information.

43. The implantable sensor system of any one of Embodiments 32 to 42, further comprising a radiopaque marker to identify a location of the implantable sensor system in the patient.

44. The implantable sensor system of any one of Embodiments 32 to 43, wherein the vascular structure is an aneurysm.

45. The implantable sensor system of Embodiment 44, wherein the one or more physiological parameters are indicative of blood flow into the aneurysm.

46. The implantable sensor system of Embodiment 44, wherein the one or more physiological parameters are indicative of blood flow out of the aneurysm.

47. The implantable sensor system of any one of Embodiments 32 to 46, wherein the antenna transmits and receives RF signals.

48. The implantable sensor system of any one of Embodiments 32 to 47, wherein the anchor structure comprises one or more coils.

49. The implantable sensor system of any one of Embodiments 32 to 47, wherein the anchor structure comprises a mesh or woven structure.

50. The implantable sensor system of any one of Embodiments 32 to 47, wherein the anchor structure comprises a basket.

51. The implantable sensor system of any one of Embodiments 32 to 50, wherein the anchor structure is capable of occluding blood flow through the vascular structure.

52. The implantable sensor system of any one of Embodiments 32 to 51, further comprising a drug 53. The implantable sensor system of Embodiment 52, wherein the anchor structure carries the drug.

54. The implantable sensor system of Embodiment 52 or 53, wherein the drug is a coagulant.

55. The implantable sensor system of any one of Embodiments 32 to 54, further comprising a power source for providing power to the sensor.

56. The implantable sensor system of Embodiment 55, wherein the power source is rechargeable.

57. The implantable sensor system of any one of Embodiments 32 to 54, wherein the sensor is capable of being powered by a power source outside the patient.

58. The implantable sensor system of any one of Embodiments 32 to 54, wherein the sensor is an inductive sensor.

59. The implantable sensor system of any one of Embodiments 32 to 54, further comprising a supercapacitor.

60. The implantable sensor system of any one of Embodiments 32 to 59, further comprising a memory device for storing sensor data.

61. The implantable sensor system of any one of Embodiments 32 to 60, further comprising a second sensor capable of detecting a different physiological parameter than the sensor.

62. A kit comprising:

the implantable sensor system of any one of Embodiments 32 to 61; and one or more delivery systems capable of releasing the implantable sensor system in the vascular structure.

63. An implantable sensor assembly comprising:

a conductivity switch responsive to blood flow, the conductivity switch capable of providing a first output indicative of a first level of blood flow and a second output indicative of a second level of blood flow; and an antenna in electrical communication with the conductive switch, the antenna capable of transmitting the first output and the second output to a receiver.

64. The implantable sensor system of Embodiment 63, wherein the second output is indicative of substantially no blood flow.

65. An implantable sensor system comprising:

a drug capable for treating a vascular structure in a patient;

a memory device configured to store a computer-executable instruction;

a processor in communication with the memory device, wherein the computer-executable instruction when executed by the processor causes the processor to cause release the drug from the implantable sensor system.

66. The implantable sensor system of Embodiment 65, further comprising a switch, wherein the computer-executable instruction when executed by the processor to activate the switch to release the drug carried by the implantable sensor system.

67. The implantable sensor system of Embodiment 65 or 66, further comprising a wireless receiver capable of receiving a transmission from outside the patient, wherein receipt of the transmission causes the processor to execute the computer-executable instruction.

68. The implantable sensor system of Embodiment 65 or 66, wherein the processor executes the computer-executable instruction after a pre-determined time following implantation of the implantable sensor system.

69. The implantable sensor system of any one of Embodiments 65 to 68, wherein the drug is a coagulant.

70. An electronic device for monitoring blood flow through a vascular structure, the electronic device comprising:

a memory device configured to store an application; and processor configured to execute the application to:

wirelessly communicate with a sensor assembly implanted in the vascular structure, the sensor assembly capable of monitoring one or more physiological parameters indicative of blood flow through the vascular structure;

determine a value of the one or more physiological parameters indicative of blood flow; and output for presentation on a display the value for presentation to a user.

71. The electronic device of Embodiment 70, wherein the value provides a metric indicative of a degree to which the vascular structure is occluding.

72. The electronic device of Embodiment 70 or 71, wherein the processor is configured to execute the application to communicate the value via a communication network to a computing system.

73. The electronic device of any one of Embodiments 70 to 72, wherein the processor is configured to execute the application to transmit a setting adjustment command to the sensor assembly to adjust a setting for monitoring the one or more physiological parameters.

74. The electronic device of any one of Embodiments 70 to 73, wherein the processor is configured to wirelessly communicate with the sensor assembly via a Bluetooth™ protocol, WiFi, ZigBee, medical implant communication service ("MICS"), the medical device radio communications service ("MedRadio"), or cellular telephony.

75. The electronic device of any one of Embodiments 70 to 74, in combination with the sensor assembly.

76. A method of monitoring a vascular structure of a patient, the method comprising:

detecting one or more physiological parameters in the vascular structure using an implantable sensor assembly; and transmitting sensor data related to the one or more physiological parameters to a remote location.

77. The method of Embodiment 76, further comprising occluding the vascular structure with an anchor structure.

78. The method of Embodiment 77, further comprising releasing a drug from the anchor structure to treat the vascular structure.

79. The method of any one of Embodiments 76 to 78, further comprising releasing a drug from the implantable sensor assembly to treat the vascular structure.

80. The method of any one of Embodiments 76 to 79, wherein the one or more physiological parameters comprises oxygen, carbon dioxide, potassium, iron, and/or glucose in the blood of the patient.

81. The method of any one of Embodiments 76 to 79, wherein the one or more physiological parameters comprises kinetic information.

82. The method of any one of Embodiments 76 to 81, wherein the implantable sensor assembly comprises a blood flow sensor, a blood pressure sensor, a metabolic sensor, a glucose sensor, or an oxygen sensor.

83. The method any one of Embodiments 76 to 82, wherein detecting one or more physiological parameters comprises intermittently detecting the one or more physiological parameters.

84. The method of any one of Embodiments 76 to 82, wherein detecting one or more physiological parameters comprises continuously detecting the one or more physiological parameters.

85. The method of any one of Embodiments 76 to 84, further comprising recharging a power source of the sensor assembly.

86. The method of any one of Embodiments 76 to 85, wherein the vascular structure comprises a neurovascular structure.

87. The method of any one of Embodiments 76 to 85, wherein the vascular structure comprises a cardiovascular structure.

88. The method of any one of Embodiments 76 to 85, wherein the vascular structure comprises an aneurysm of an artery in a posterior circulation of the patient.

89. The method of any one of Embodiments 76 to 85, wherein the vascular structure comprises a basilar aneurysm.

90. The method of any one of Embodiments 76 to 85, wherein the vascular structure comprises a bifurcation aneurysm.

91. The method of any one of Embodiments 76 to 85, wherein the vascular structure comprises a sidewall aneurysm.

92. The method of any one of Embodiments 76 to 85, wherein the vascular structure comprises a ductus arteriosus.

93. The method of any one of Embodiments 76 to 85, wherein the vascular structure comprises a carotid artery.

94. The method of any one of Embodiments 76 to 85, wherein the vascular structure comprises a venous structure.

95. The method of any one of Embodiments 76 to 94, further comprising delivering a flow diverter based on the sensor data.

96. The method of Embodiments 76 to 95, further comprising delivering a coagulant based on the sensor data 97. A method of implanting a sensor system into a vascular structure of a patient, the method comprising:

advancing a delivery system carrying a sensor system to a vascular structure, the sensor system comprising a sensor assembly and an anchor structure;

releasing the sensor assembly in the vascular structure; and releasing the anchor structure in the vascular structure.

98. The method of Embodiment 97, further comprising occluding the vascular structure with the anchor structure.

99. The method of Embodiment 97 or 98, further comprising introducing the delivery system percutaneously.

100. The method of any one of Embodiments 97 to 99, further comprising advancing the delivery system over a guidewire.

101. The method of any one of Embodiments 97 to 99, further comprising advancing the delivery system through a guide catheter.

102. The method of any one of Embodiments 97 to 101, further comprising positioning the anchor structure around the sensor.

103. The method of any one of Embodiments 97 to 101, further comprising positioning the sensor within the anchor structure.

104. The method of any one of Embodiments 97 to 101, further comprising simultaneously releasing the sensor and the anchor structure.

105. The method of any one of Embodiments 97 to 104, further comprising detecting one or more physiological parameters within the vascular structure.

106. The method of Embodiment 105, further comprising transmitting sensor data related to the one or more physiological parameters to a remote location.

107. The method of any one of Embodiments 97 to 106, further comprising recharging a power source of the sensor assembly.

108. The method of any one of Embodiments 97 to 107, wherein the vascular structure comprises an aneurysm of an artery in a posterior circulation of the patient.

109. The method of any one of Embodiments 97 to 107, wherein the vascular structure comprises a neurovascular structure.

110. The method of any one of Embodiments 97 to 107, wherein the vascular structure comprises a cardiovascular structure.

111. The method of any one of Embodiments 97 to 107, wherein the vascular structure comprises a basilar aneurysm.

112. The method of any one of Embodiments 97 to 107, wherein the vascular structure comprises a bifurcation aneurysm.

113. The method of any one of Embodiments 97 to 107, wherein the vascular structure comprises a sidewall aneurysm.

114. The method of any one of Embodiments 97 to 107, wherein the vascular structure comprises a ductus arteriosus.

115. A delivery system capable of delivering a sensor assembly into a vascular structure of a patient, the delivery system comprising:

a shaft comprising a lumen;

a deflectable distal tip capable of carrying the sensor assembly, the lumen extending through the deflectable distal tip; and a handle comprising:

a first user-actuatable mechanism to release the sensor assembly from the deflectable distal tip; and a second user-actuatable system to steer the deflectable distal tip.

116. The delivery system of Embodiment 115, wherein the shaft comprises a guidewire lumen.

117. The delivery system of Embodiment 115 or 116, wherein the second user-actuatable mechanically controls steering of the deflectable distal tip.

118. The delivery system of Embodiment 117, wherein the second user-actuatable mechanism electrically controls steering of the deflectable distal tip.

119. The delivery system of any one of Embodiments 115 to 118, further comprising a delivery sleeve positioned over the shaft.

120. The delivery system of Embodiment 119, wherein the delivery sleeve enables steering of the deflectable distal tip.

121. The delivery system of any one of Embodiments 115 to 120, further comprising a fluid port to flush the delivery system.

122. The delivery system of one of Embodiments 115 to 121, wherein the flexible shaft comprises a second lumen configured to enable steering of the deflectable distal tip.

123. The delivery system of one of Embodiments 115 to 122, wherein the deflectable distal tip comprises a loading chamber separate from the lumen, the loading chamber carrying the sensor assembly.

124. The delivery system of one of Embodiments 115 to 123, wherein the shaft comprises a polymeric material.

125. The delivery system of one of Embodiments 115 to 124, wherein the handle further comprises a third user-actuatable mechanism to stabilize a position of the deflectable distal tip.

126. An implantable sensor system comprising:

a sensor assembly capable of being implanted within an aneurysm and measuring a physiological parameter;

an anchor structure for maintaining a position of the sensor assembly in the aneurysm, the anchor structure joined to the sensor assembly; and an antenna in electrical communication with the sensor assembly.

127. The implantable sensor system of embodiment 126, wherein the sensor assembly comprises a glucose sensor.

128. The implantable sensor system of embodiment 126 or 127, wherein the sensor assembly comprises a conductivity switch.

129. The implantable sensor system of any one of embodiments 126 to 128, wherein the sensor assembly comprises a processor for at least partially processing data collected by the sensor.

130. The implantable sensor system of embodiment 129, wherein the processor is hermetically sealed.

131. The implantable sensor system of any one of embodiments 126 to 130, wherein an outer surface of the sensor assembly comprises peaks and valleys.

132. The implantable sensor system of any one of embodiments 126 to 131, further comprising a supercapacitor to power the sensor assembly.

133. The implantable sensor system of embodiment 132, wherein the supercapacitor is joined to the anchor structure.

134. The implantable sensor system of embodiment 133, wherein the anchor structure is positioned between the sensor assembly and the supercapacitor.

135. The implantable sensor system of any one of embodiments 126 to 134, wherein the sensor assembly is positioned between the antenna and the anchor structure.

136. The implantable sensor system of any one of embodiments 126 to 135, wherein the anchor structure extends radially outward from the sensor assembly to contact a wall of the aneurysm.

137. The implantable sensor system of any one of embodiments 126 to 136, wherein the anchor structure comprises a plurality of loop-shaped anchor portions.

138. The implantable sensor system of embodiment 137, wherein the plurality of anchor portions are positioned circumferentially around the sensor assembly.

139. The implantable sensor system of embodiment 137 or 138, wherein each of the plurality of anchor portions comprises an atraumatic end portion to contact a wall of the aneurysm.

140. The implantable sensor system of any one of embodiments 126 to 139, wherein the anchor structure is drug coated.

141. The implantable sensor system of any one of embodiments 126 to 141, wherein the sensor assembly comprises a memory device for storing the sensor data.

142. A delivery system for deploying a sensor system in a vascular structure, the delivery system comprising:

a handle portion;

a delivery sheath extending distally from the handle portion;

an inner shaft extending through the delivery sheath, the inner shaft comprising a shaft wall defining a lumen;

a retaining wire extending through the inner shaft, the retaining wire configured to retain a sensor system in a space between an outer wall of the inner shaft and an inner wall of the delivery sheath.

143. The delivery system of embodiment 142, wherein the inner shaft comprises a plurality of openings in the shaft wall.

144. The delivery system of embodiment 143, wherein the plurality of openings are axially spaced apart along the shaft wall.

145. The delivery system of embodiment 143 or 144, wherein each of the plurality of openings is rotationally aligned.

146. The delivery system of embodiment 143 or 144, wherein at least one of the plurality of openings is rotationally offset from another one of the plurality of openings.

147. The delivery system of any one of embodiments 142 to 146, wherein the retaining wire forms one or more loop portions to retain the sensor system against the inner shaft.

148. The delivery system of embodiment 147, wherein the retaining wire extends out of a first opening in the shaft wall and into the space between the inner shaft and the delivery sheath, and back through a second opening in the shaft wall and into the lumen of the inner shaft to form one of the one or more loop portions.

149. The delivery system of embodiment 147, wherein the retaining wire extends out of a first opening in the shaft wall and into the space between the inner shaft and the delivery sheath, and back through the first opening in the shaft wall and into the lumen of the inner shaft to form one of the one or more loop portions.

150. The delivery system of any one of embodiments 142 to 149, wherein a distal portion of the inner shaft is deflectable.

151. The delivery system of any one of embodiments 142 to 150, wherein a distal portion of the inner shaft is steerable to deflect the distal portion of the inner shaft into the vascular structure.

152. A method of deploying a sensor system in an aneurysm, the method comprising:

advancing a delivery system carrying a sensor system to a parent artery, the sensor system carried by an inner shaft of the delivery system;

unsheathing the sensor system; and deploying the sensor system in the aneurysm.

153. The method of embodiment 152, wherein deploying the sensor system comprises withdrawing a retaining wire to release the sensor system in the aneurysm.

154. The method of embodiment 153, wherein withdrawing the retaining wire releases the retaining wire from an anchor structure of the sensor system.

155. The method of any one of embodiments 152 to 154, wherein deploying the sensor system causes an anchor structure of the sensor system to expand and stabilize a position of the sensor system in the aneurysm 156. The method of any one of embodiments 152 to 155, wherein deploying the sensor system in the aneurysm positions a sensor of the sensor system away from a wall of the aneurysm.

157. The method of any one of embodiments 152 to 156, further comprising, after deploying the sensor system in the aneurysm, deploying a treatment device in the aneurysm.

158. The method of any one of embodiments 152 to 157, wherein deploying the treatment device comprises deploying the treatment device around the sensor.

159. The method of any one of embodiments 152 to 158, wherein deploying the sensor system comprises releasing communication circuitry of the sensor system in the aneurysm prior to releasing an anchor structure of the sensor system.

160. The method of any one of embodiments 152 to 159, further comprising steering a distal tip of the inner shaft into the aneurysm prior to deploying the sensor system in the aneurysm.

161. The method of any one of embodiments 152 to 159, further comprising positioning the sensor system against a neck of the aneurysm prior to deploying the sensor system in the aneurysm.

All references disclosed herein, including patent references and non-patent references, are hereby incorporated by reference in their entirety as if each was incorporated individually.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to “one embodiment” or “an embodiment” and variations thereof means that a particular feature, structure, or characteristic described in connection with the embodiment is included in at least one embodiment. Thus, the appearances of the phrases “in one embodiment” or “in an embodiment” in various places throughout this specification are not necessarily all referring to the same embodiment. Furthermore, the particular features, structures, or characteristics may be combined in any suitable manner in one or more embodiments.

As used in this specification and the appended claims, the singular forms “a,” “an,” and “the” include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art. Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. An implantable sensor system capable of being implanted within an intracranial saccular aneurysm of a patient, the sensor system comprising:

a sensor capable of detecting one or more physiological parameters of the patient and generating sensor data, wherein the sensor comprises a glucose sensor and the one or more physiological parameters comprises glucose in the blood of the patient; and an antenna assembly in electrical communication with the sensor, the antenna assembly comprising a plurality of at least five antennae wrapped around the sensor and forming a spherical structure that encloses the sensor, the spherical structure configured to fit within the intracranial aneurysm and to anchor the system within the intracranial aneurysm, the antenna assembly configured to transmit sensor data related to the one or more physiological parameters of the patient to a receiver, the antenna assembly capable of being compressed for loading into a delivery system and expanded upon release from the delivery system.

2. The implantable sensor system of claim 1, further comprising a sealing layer to hermetically seal the sensor.

3. The implantable sensor system of claim 1, further comprising a dissolving membrane layer that dissolves when in contact with blood of the patient.

4. The implantable sensor system of claim 1, further comprising a power source for providing power to the sensor.

5. The implantable sensor system of claim 1, further comprising a supercapacitor to provide power to the sensor.

6. The implantable sensor system of claim 1, further comprising a memory device for storing sensor data.

7. The implantable sensor system of claim 1, further comprising a second sensor capable of detecting a different physiological parameter than glucose.

8. The implantable sensor system of claim 1, wherein the sensor further comprises a conductivity switch configured to detect a presence of fluid above a threshold amount.

9. The implantable sensor system of claim 8, wherein the conductivity switch comprises two spaced apart conductive pads.

10. The implantable sensor system of claim 8, wherein the glucose sensor is configured to operate only when fluid above the threshold amount is detected.

11. A kit comprising:

the implantable sensor system of claim 1; and a delivery system capable of releasing the implantable sensor assembly into an aneurysm of a patient in a vascular structure.

12. A method of monitoring an aneurysm of a patient, the method comprising:

detecting one or more physiological parameters of the aneurysm using an implantable sensor system of claim 1; and transmitting sensor data related to the one or more physiological parameters to a remote location.

13. The method of claim 12, further comprising occluding the aneurysm with an anchor structure.

14. A method of implanting a sensor system into an aneurysm of a patient, the method comprising:

advancing a delivery system carrying the sensor system of claim 1 to an intracranial aneurysm of the patient; and releasing the sensor system inside the intracranial aneurysm; whereupon the antenna assembly adopts a spherical structure configured to fit within the intracranial aneurysm and to anchor the sensor system within the intracranial aneurysm.

15. An implantable sensor system capable of being implanted within an intracranial saccular aneurysm of a patient, the sensor system comprising:

a sensor capable of detecting one or more physiological parameters of a patient and generating sensor data, wherein the sensor comprises a glucose sensor and the one or more physiological parameters comprises glucose in the blood of the patient and a conductivity switch configured to detect a presence of fluid above a threshold amount;

an antenna assembly in electrical communication with the sensor, the antenna assembly comprising a plurality of at least five antennae wrapped around the sensor and forming a spherical structure that encloses the sensor, the spherical structure configured to fit within the intracranial aneurysm and to anchor the system within the intracranial aneurysm, the antenna assembly configured to transmit sensor data related to the one or more physiological parameters of the patient to a receiver, the antenna assembly capable of being compressed for loading into a delivery system and expanded upon release from the delivery system; and wherein the implantable sensor system is configured to fit within an intracranial aneurysm of the patient, and the system comprises a radiopaque marker selected to allow identification of the location of the system within the intracranial space of the patient.

16. A kit comprising:

the implantable sensor system of claim 15; and a delivery system comprising a shaft having a shaft wall defining a lumen, and a retention wire extending along the shaft partially within the lumen and partially outside the lumen, wherein portions of the retention wire outside the lumen retain the anchor structure in place relative to the shaft, the retention wire capable of being moved relative to the shaft to thereby release the implantable sensor system from the shaft into the aneurysm.

* * * * *